United States Patent
Shiina et al.

[11] Patent Number: 5,849,115
[45] Date of Patent: Dec. 15, 1998

[54] ALLOY MATERIAL FOR THIXOCASTING, PROCESS FOR PREPARING SEMI-MOLTEN ALLOY MATERIAL FOR THIXOCASTING AND THIXOCASTING PROCESS

[75] Inventors: Haruo Shiina; Nobuhiro Saito; Takeyoshi Nakamura; Takeshi Sugawara, all of Saitama, Japan

[73] Assignee: Honda Giken Kogyo Kabushiki Kaisha, Tokyo, Japan

[21] Appl. No.: 861,265

[22] Filed: May 21, 1997

Related U.S. Application Data

[63] Continuation of Ser. No. 441,158, May 15, 1995, abandoned.

[30] Foreign Application Priority Data

| May 17, 1994 | [JP] | Japan | 6-128290 |
| Oct. 12, 1994 | [JP] | Japan | 6-272897 |
| Nov. 22, 1994 | [JP] | Japan | 6-311292 |
| Jan. 12, 1995 | [JP] | Japan | 7-019738 |
| Jan. 30, 1995 | [JP] | Japan | 7-033125 |
| Jan. 30, 1995 | [JP] | Japan | 7-033126 |
| Jan. 31, 1995 | [JP] | Japan | 7-034665 |

[51] Int. Cl.⁶ .................................................. B22D 21/00
[52] U.S. Cl. ............................ 148/549; 148/437; 164/900
[58] Field of Search ............................ 148/95, 549, 415, 148/437; 164/900

[56] References Cited

U.S. PATENT DOCUMENTS

| 1,947,121 | 2/1934 | Bonsack | 420/544 |
| 4,694,882 | 9/1987 | Busk | 164/113 |
| 5,133,811 | 7/1992 | Kirkwood et al. | 148/95 |
| 5,701,942 | 12/1997 | Adachi et al. | 148/549 |

FOREIGN PATENT DOCUMENTS

| 0 392 998 A1 | 10/1990 | European Pat. Off. . |
| 476843 | 3/1992 | European Pat. Off. . |
| 0 554 808 A1 | 8/1993 | European Pat. Off. . |
| 618303 | 10/1994 | European Pat. Off. . |
| 2139494 | 1/1973 | France . |
| 2250437 | 5/1975 | France . |
| 2514355 | 10/1975 | Germany . |
| 22 29 453 B2 | 9/1976 | Germany . |
| 25 14355 C3 | 10/1984 | Germany . |
| 28 53 202 A1 | 6/1997 | Germany . |
| 06297097 A | 10/1994 | Japan . |
| 06297098 A | 10/1994 | Japan . |
| 1391121 | 4/1975 | United Kingdom . |
| 1499934 | 2/1978 | United Kingdom . |
| 1502114 | 2/1978 | United Kingdom . |
| 2176011 | 12/1986 | United Kingdom . |

OTHER PUBLICATIONS

Article entitled "Thixocasting—ein GieBverfahren zur Near–net–shape–Produktion," by H.P. Erz, Giesserei 77, 1990, Nr. 19–17, Sep., pp. 613–617—German (no translation).

Scripta Metallurgica, vol. 18, No. 1, 1984, pp. 301–304, XP000568503; Balmuth: "Particle Size Determination in An AL–3LI Allp:oy Using DSC".

*Primary Examiner*—George Wyszomierski
*Attorney, Agent, or Firm*—Lyon & Lyon LLP

[57] ABSTRACT

A differential thermal analysis thermograph for a thixocasting aluminum alloy material is such that, a relationship, $E_1 > E_2$, is established between a peak value $E_1$ of a first angled endothermic section generated by eutectic melting and a peak value $E_2$ of a second angled endothermic section generated by melting of an element having a melting point higher than the eutectic point. Thus, a liquid phase produced by the eutectic melting has a large latent heat due to the fact that the peak value $E_1$ of the first angled endothermic section is larger than the peak value $E_2$ of the second angled endothermic section in a semi-molten eutectic aluminum alloy material derived from the thixocasting aluminum alloy material. As a result, in a solidification step of the thixocasting process, a liquid phase produced by the eutectic melting is sufficiently fed around a solid phase in response to the solidification and shrinkage of the solid phase, and then solidified. Thus, it is possible to produce a casting free from defects such as voids on the order of a micron.

14 Claims, 61 Drawing Sheets

Example A

Al alloy casting A

Comparative example a₂

Al alloy casting a₂

Example $A_2$

Al alloy casting $A_2$

100μm

Comparative example a

Al alloy casting a

25μm

Al alloy casting $A_1$

Example A₂

Al alloy casting A₂

Example A₃

Al alloy casting A₃

Example A₄

Al alloy casting A₄

Comparative example $a_1$

Al alloy casting $a_1$

Comparative example $a_2$

Al alloy casting $a_2$

FIG. 19A
Comparative example $a_3$
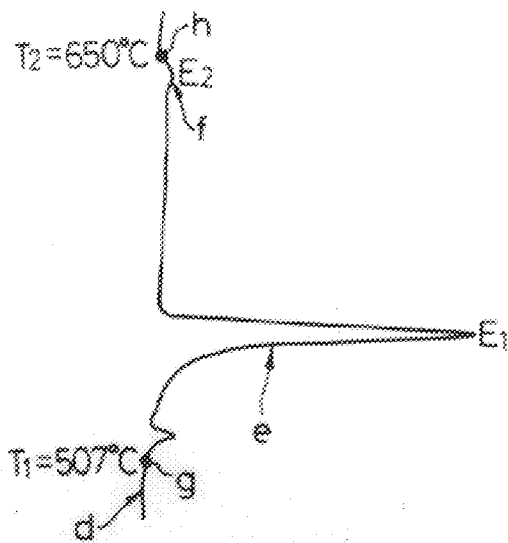
FIG. 19C
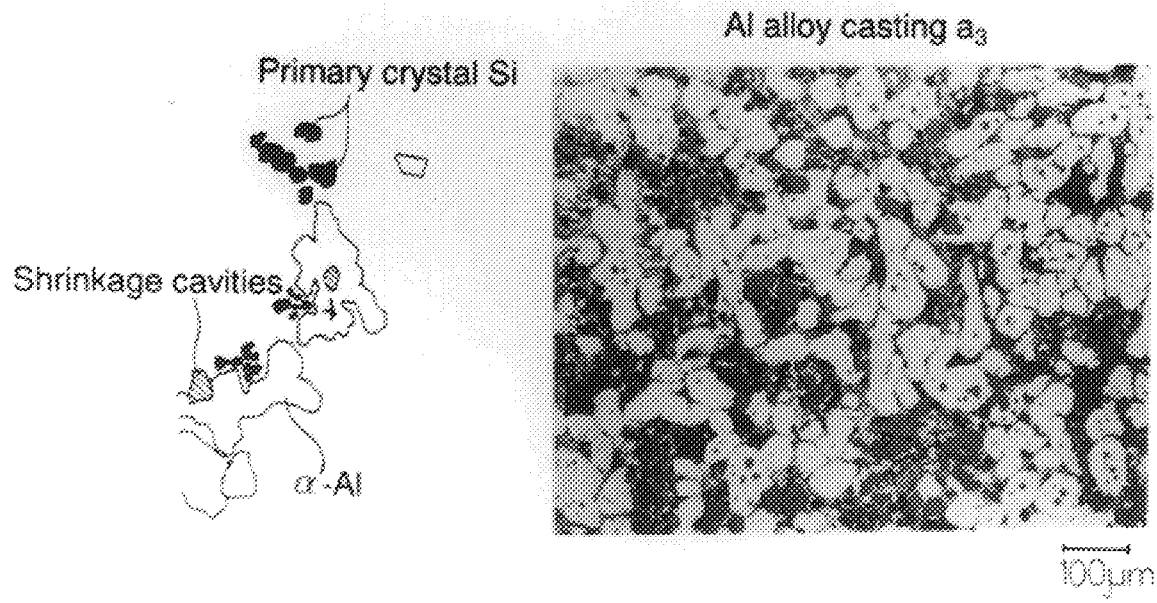
FIG. 19B
Al alloy casting $a_3$ Comparative example a₄

Al alloy casting a₄

Comparative example $a_5$

Al alloy casting $a_5$

Example $A_1$

Al alloy casting (example A₁)

Al alloy casting (example $A_2$)

Al alloy casting (comparative example a₁)

Example A_7

Comparative example a_1

Al alloy casting A₇

100μm

Al alloy casting $a_1$

Al alloy casting a₃

Al alloy casting $a_2$

Comparative example $a_2$

Comparative example $a_3$

Al alloy casting A₁

Al alloy casting a₁

Al alloy casting A₁₁

Al alloy casting A₁

ALLOY MATERIAL FOR THIXOCASTING, PROCESS FOR PREPARING SEMI-MOLTEN ALLOY MATERIAL FOR THIXOCASTING AND THIXOCASTING PROCESS

This is a continuation of application Ser. No. 08/441,158 filed May 15, 1995, now abandoned.

BACKGROUND OF THE INVENTION

1. Field of the Invention

The present invention relates to an alloy material for thixocasting, a process for preparing a semi-molten alloy material for thixocasting, and a thixocasting process.

2. Description of the Prior Art

Conventionally known alloy materials for thixocasting such as aluminum alloys include AA specification 2000-series alloys used to provide an enhancement in heat resistance of a casting, and AA specification 6000-series alloys used to provide increases in strength and toughness of a casting.

In carrying out the thixocasting process, a procedure is employed which involves subjecting an aluminum alloy material to a heating treatment to prepare a semi-molten aluminum alloy material having a solid phase (which hereinafter indicates a substantially solid phase) and a liquid phase coexisting therein, pouring the semi-molten aluminum alloy material under pressure into a cavity in a casting mold, and solidifying the semi-molten aluminum alloy material under the pressure.

In carrying out the thixocasting process, however, the following problem is encountered: when a conventional aluminum alloy material is used, defects such as voids on the order of a micron are liable to be generated at the boundary between the granular solid phases of the casting.

The generation of such defects is particularly prominent at thick portions of the casting and where casting has complicated shapes and the like, and causes a reduction in the fatigue strength of the casting.

The known materials of this type include alloy materials, that have, in a differential thermal analysis thermograph both a first angled endothermic section generated by eutectic melting and a second angled endothermic section generated by the melting of a segment having a melting point higher than the eutectic point, and a difference $T_5-T_4$ between a peak temperature $T_4$ of the first angled endothermic section and a peak temperature $T_5$ of the second angled endothermic section in a range represented by $T_5-T_4<20°$ C.

The reason why the difference $T_5-T_4$ between the temperatures $T_4$ and $T_5$ is set at such a small value as described above is that the range of solid-liquid coexistence temperature of the alloy material is narrowed to inhibit the generation of a shrinkage cavity during solidification.

However, in the alloy material having a temperature difference $T_5-T_4$ set at such a small value, the solid phase proportion is varied in accordance with a variation in heating temperature. For this reason, in order to uniformly heat such an alloy material, the temperature rising rate must be reduced, namely, the heating time must be set at a large value. As a result, there is a disadvantage of including a coalescence of primary crystals which are main segments for the solid phase. On the other hand, if the temperature rising rate is increased, i.e., if the heating time is set short, the distribution of solid proportion in the semi-molten alloy material is not uniform, resulting in a disadvantage that the semi-molten alloy material is charged in a sprayed state into the cavity in the casting course and as a result, air is included into the semi-molten alloy material to generate relatively large voids.

In this type of alloy material, the range of temperature permitting the liquid phase due to the eutectic melting to exist in the course of solidification, is set at a relatively narrow range in order to avoid the generation of shrinkage cavities.

In the heating treatment of the alloy material, it is necessary to increase the temperature rising rate for the alloy material to rapidly heat the alloy material within a short time up to a casting temperature in order to provide an increase in efficiency.

However, if the conventional alloy material is rapidly heated, the following problem is encountered: it is impossible to flow the liquid phase to uniformize the distribution of the liquid phase in the course of solidification, because the range of temperature permitting the liquid phase to exist is relatively narrow. As a result, the metallographic structure of the produced casting is not uniform and hence, the casting has a low fatigue strength.

There is a conventionally known process for preparing a semi-molten alloy material for thixocasting by heating an alloy material having a first angled endothermic section generated by eutectic melting and a second angled endothermic section generated by melting of an element having a melting point higher than the eutectic point in a differential thermal analysis thermograph, to a casting temperature between a dropping end point in the first angled endothermic section and a peak of the second angled endothermic section, so that solid and liquid phases coexist in the semi-molten alloy material. In this case, the average temperature rising rate for the alloy material is set to be substantially constant and considerably high. The reason why the average temperature rising rate is set in this manner is that the coalescence of the metallographic structure due to the growth of a primary crystal or the like is prevented to enhance the heating performance.

However, the known process suffers from a problem that the profile of the temperature of the liquid phase in the semi-molten alloy material is liable to become non-uniform, and due to this, voids on the order of a micron are generated and for this reason, it is difficult to produce a casting having a high grade of mechanical properties such as an excellent fatigue strength.

In carrying out the thixocasting process, it is a conventional practice to set the temperature of a semi-molten alloy material during casting, i.e., the casting temperature at a level between a rising start point in the first angled endothermic section and a dropping end point in the first angled endothermic section to maintain the semi-molten alloy material at a high solid phase proportion in order to improve the handling ability of the semi-molten alloy material.

However, if the thixocasting process is carried out under a high solid phase proportion as in the known process, the following problem is encountered: despite the use of, for example, a hypoeutectic alloy material, a primary crystal of alloy elements is precipitated with an eutectic reaction of the semi-molten alloy material, and due to this, a casting having a reduced ductility and toughness is produced. This phenomenon is generated in an Al-Si alloy, an Al-CuAl$_2$ alloy, an Al-Mg$_2$Si alloy and the like.

SUMMARY OF THE INVENTION

The present inventors have made studies to solve the above problems and as a result, they have found that the defects of the casting is due to the liquid phase being insufficiently fed around the solid phase in response to the solidification and shrinkage of the solid phase, because of the small latent heat of the liquid phase in the semi-molten aluminum alloy material.

The present invention has been accomplished with the result of the studies taken into account, and it is an object of the present invention to provide an alloy material of the above-described type, from which a casting free from defects and having a sound quality can be produced in a thixocasting process.

To achieve the above object, according to the present invention, there is provided an alloy material for thixocasting, wherein in a differential thermal analysis thermograph, a peak value $E_1$ of a first angled endothermic section generated by eutectic melting is larger than a peak value $E_2$ of a second angled endothermic section generated by melting of an element having a melting point higher than the eutectic point.

A semi-molten alloy material having solid and liquid phases coexisting therein is prepared by subjecting the alloy material to a heating treatment. In this semi-molten alloy material, the liquid phase produced by the eutectic melting has a large latent heat due to the fact that the peak value $E_1$ of the first angled endothermic section is larger than the peak value $E_2$ of the second angled endothermic section. As a result, the liquid phase is sufficiently fed around the solid phase and then solidified in response to the solidification and shrinkage of the solid phase in the course of solidification of the thixocasting process. Thus, it is possible to produce a casting free from defects, such as voids on the order of a micron, and having a sound casting quality.

The present inventors have made studies to solve the above-described problems and consequently have found that the defects of the casting is also due to a degraded compatibility between the solid and liquid phases because the latent heat of the liquid phase in the semi-molten alloy material is small and hence, the liquid phase is insufficiently fed around the solid phase in response to the solidification and shrinkage of the solid phase. Furthermore, an outer periphery of the solid phase is substantially in the solid state.

The present invention has been accomplished with the result of the studies taken into account, and it is an object of the present invention to provide an alloy material of the above-described type, which exhibits a good feedability of a liquid phase to a solid phase and a good compatibility between solid and liquid phases in a thixocasting process, and from which a casting free from defects and having a sound casting quality and a high fatigue strength can be produced in the thixocasting process.

To achieve the above object, according to the present invention, there is provided an alloy material for thixocasting, wherein in a differential thermal analysis thermograph, a ratio $E_1/E_2$ of a peak value $E_1$ of a first angled endothermic section generated by eutectic melting to a peak value $E_2$ of a second angled endothermic section generated by melting of an element having a melting point higher than an eutectic point is in a range of $1<E_1/E_2<2.5$, and a difference $T_2-T_1$ between a temperature $T_1$ at a rising start point in the first angled endothermic section and a temperature $T_2$ at a dropping end point in the second angled endothermic section is in a range of $10°\,C.<T_2-T_1<120°\,C.$ A semi-molten alloy material including liquid and solid phases coexisting and having a eutectic composition is prepared by subjecting the above described alloy material to a heating treatment. In this semi-molten alloy material, the liquid phase has a large latent heat due to the fact that the ratio $E_1/E_2$ of the peak values $E_1$ and $E_2$ is as specified above. As a result, the liquid phase is sufficiently fed around the solid phase and then solidified in response to the solidification and shrinkage of the solid phase in the course of solidification of the thixocasting process. The outer periphery of the solid phase is in a gelled state due to the fact that the difference $T_2-T_1$ between the temperatures is specified. As a result, the compatibility between the gelled outer periphery of the solid phase and the liquid phase is improved. Thus, it is possible to prevent the generation of voids on the order of a micron in the casting.

The quantity balance between the solid and liquid phases is excellent due to the ratio $E_1/E_2$ specified in the above manner and hence, the semi-molten alloy material becomes a homogeneous fluid in the course of casting. Thus, it is possible to prevent the generation of a segregation in the casting. Such a casting has a sound casting quality and a high fatigue strength.

However, if the ratio $E_1/E_2$ of the peak value $E_1$ to the peak value $E_2$ is equal to or smaller than 1 ($E_1/E_2 \leq 1$), the latent heat of the liquid phase is decreased and for this reason, the feeding of the liquid phase around the solid phase is insufficient in the course of the solidification and shrinkage. As a result, voids on the order of a micron are liable to be produced in the casting. On the other hand, if $E_1/E_2 \geq 2.5$, a primary crystal is segregated and coalesced and hence, voids are likewise liable to be generated. The segregation of the primary crystal is due to the fact that the semi-molten alloy material becomes an inhomogeneous fluid in the course of casting (e.g., during passing of the alloy material through a gate of a mold), because of a large amount of the liquid phase. On the other hand, the coalescence of the primary crystal is due to the fact that the cooling of the primary crystal is delayed, when an excessive amount of the liquid phase is solidified, because of a large latent heat of the liquid phase.

If the difference $T_2-T_1$ between the temperatures is equal to or lower than 10° C., a solid-liquid coexisting state having a predetermined solid proportion cannot be maintained stably, and the gelling of the outer periphery of the solid phase is sufficient. As a result, voids are likewise liable to be produced. On the other hand, if $T_2-T_1 \geq 120°$ C., shrinkage cavities are liable to be generated in the casting, because of a prolonged time of course of solidification of the liquid phase in the solidification.

It is a further object of the present invention to provide an alloy material of the above-described type, which exhibits a good feedability of a liquid phase to a solid phase, and from which a casting free from defects and having a sound casting quality and a high fatigue strength can be produced in the thixocasting process.

To achieve the above object, according to the present invention, there is provided an alloy material for thixocasting, wherein in a differential thermal analysis thermograph, a relationship of $E_1>E_2$ is established between a peak value $E_1$ of a first angled endothermic section generated by an eutectic melting and a peak value $E_2$ of a second angled endothermic section generated by melting of an element having a melting point higher than an eutectic point. Further, when a temperature straight line interconnecting a peak of the first angled endothermic section and a temperature graduation of the peak on an axis of heating temperature intersects a basic line which interconnects a rising start point in the first angled endothermic section and a dropping end point in the second angled endothermic section, and when a dividing line bisecting one segment of the temperature straight line lying between the peak and a first intersection of the temperature straight line with the basic line intersects a rising line segment of the first angled endothermic section lying between the rising start point and the peak, a relationship of $\Delta Tb/\Delta Ta \leq 0.68$ is established between $\Delta Ta$ $(=T_4-T_1)$ and $\Delta Tb$ $(=T_3-T_1)$, wherein $T_1$ represents a temperature at the rising start point, $T_3$ represents a temperature at a second intersection between the rising line segment and the dividing line, and $T_4$ represents the peak temperature.

According to the present invention, there is also provided an alloy material for thixocasting, wherein a relationship of $E_1 > E_2$ is established between a peak value $E_1$ of a first angled endothermic section generated by eutectic melting and a peak value $E_2$ of a second angled endothermic section generated by melting of a segment having a melting point higher than the eutectic point in a differential thermal analysis thermograph. Further, a relationship of $Sm/St \leq 0.365$ is established between (1) an area $St$ of a region surrounded by (i) a basic line which interconnects a rising start point of the first angled endothermic section and a dropping end point in the second angled endothermic section, (ii) a first temperature straight line which interconnects a peak of the first angled endothermic section and a temperature graduation of the peak on an axis of heating temperature, and (iii) a rising line segment of the first angled endothermic section lying between the rising start point and said peak, and (2) an area $Sm$ of a region surrounded by (i) a second temperature straight line which interconnects (a) a second intersection of the rising line segment with a dividing line which bisects a segment of the first temperature straight line lying between a first intersection of the first temperature straight line with the basic line and the peak, and (b) a temperature graduation of the second intersection on the axis of heating temperature, (ii) a portion of the rising line segment lying between the rising start point of said first angled endothermic section and the second intersection, and (iii) the basic line.

A semi-molten alloy material having solid and liquid phases coexisting therein is prepared by subjecting the alloy material to a heating treatment. In this semi-molten alloy material, the liquid phase produced by eutectic melting has a large latent heat due to the fact that the peak value $E_1$ of the first angled endothermic section is larger than the peak value $E_2$ of the second endothermic section. As a result, in the course of solidification in the thixocasting process, the liquid phase is sufficiently fed around the solid phase and then solidified. Thus, it is possible to prevent the generation of voids on the order of a micron in a relatively thin portion, a portion of a simple shape or the like of a casting.

If the latent heat of the liquid phase is reduced to ½ of the maximum released latent heat, namely to $E_1/2$ in the course of solidification of the semi-molten alloy material, the liquid phase is thereafter gelled, so that the viscosity is gradually increased. Due to this, the feedability of the liquid phase around the solid phase, particularly in a thicker portion, a portion of a complicated shape or the like of a casting is degraded and hence, voids on the order of a micron are liable to be generated in the thicker portion or the like.

The value $\Delta Ta$ represents a temperature drop range required for the liquid phase to be solidified, and the value $\Delta Tb$ represents a temperature drop range required for the gelled phase produced from the liquid phase to be solidified. Therefore, if $\Delta Tb/\Delta Ta$ is set in a range of $\Delta Tb/\Delta Ta \leq 0.68$, the temperature range required for the gelled phase to be solidified is narrowed, and on the other hand, the temperature range permitting the gelled phase to be produced from the liquid phase is relatively widened. Thus, it is possible to improve the feedability of the liquid phase around the solid phase in the thicker portion of the casting or the like to prevent the generation of voids on the order of a micron.

The area $St$ indicates a released latent heat amount required for the liquid phase to be solidified, and the area $Sm$ indicates a released latent heat amount required for the gelled phase produced from the liquid phase to be solidified. Therefore, if $Sm/St$ is set in a range of $Sm/St \leq 0.365$, the released latent heat amount required for the gelled phase to be solidified is decreased, and on the other hand, the released latent heat amount permitting the gelled phase to be produced from the liquid phase is relatively increased. Thus, it is possible to improve the feedability of the liquid phase around the solid phase in the thicker portion of the casting or the like to prevent the generation of voids on the order of a micron. Such a casting has a sound casting quality.

Further, it is another object of the present invention to provide an alloy material for thixocasting of the above-described type, from which a casting having a sound casting quality and higher mechanical properties such as an excellent fatigue strength can be produced by specifying the difference $T_5-T_4$ between the peak temperatures $T_4$ and $T_5$ of the first and second angle endothermic sections.

To achieve the above object, according to the present invention, there is provided an alloy material for thixocasting, wherein in a differential thermal analysis thermograph, there exist a first angled endothermic section generated by eutectic melting and a second angled endothermic section generated by melting of a segment having a melting point higher than the eutectic point, and wherein a difference $T_5-T_4$ between a peak temperature $T_4$ of the first angled endothermic section and a peak temperature $T_5$ of the second angled endothermic section is in a range of $20°\text{C}. \leq T_5-T_4 \leq 80°\text{C}$.

In the alloy material having the characteristic that the difference $T_5-T_4$ between the temperatures $T_4$ and $T_5$ is specified in the above range, the variation in solid phase proportion relative to the variation in heating temperature is blunted. Therefore, it is possible to increase the temperature rising rate to heat the alloy material up to a casting temperature (which hereinafter indicates a temperature of the material during casting) within a short time, thereby preventing the coalescence of the primary crystal.

In addition, the diffusion of the primary crystal is actively effected as a result of widening of the temperature range permitting the solid and liquid phases to coexist, and therefore, the fine spheroidization and the uniform dispersion of the primary crystal are promoted. This brings about the uniformization of the metallographic structure in the semi-molten alloy material, so that the uniform solidification of the material is achieved, thereby avoiding the generation of shrinkage cavities in a casting. Such a casting has a sound casting quality and high mechanical properties such as an excellent fatigue strength.

However, if the difference $T_5-T_4$ between the temperatures is lower than $20°$ C., the above-described disadvantage arises. On the other hand, if $T_5-T_4>80°$ C., the solid/liquid phase coexisting temperature range of the alloy material is too wide, and hence, shrinkage cavities are liable to be generated during solidification.

It is a further object of the present invention to provide an alloy material of the above-described type, from which a casting having a uniform metallographic structure can be produced, even when the alloy material is rapidly heated.

To achieve the above object, according to the present invention, there is provided an alloy material for thixocasting, wherein in a differential thermal analysis thermograph, there exist a first angled endothermic section generated by eutectic melting and a second angled endothermic section generated by melting of a segment having a melting point higher than the eutectic point, the second angled endothermic section having a sloping portion between a peak of the second angled endothermic section and a dropping end point in the second angled endothermic section, the sloping portion extending along a straight line interconnecting a rising start point in the first angled endothermic section and the dropping end point in the second angled endothermic section. Further, a proportion Rt (Td/Tc×100) of a temperature range Td between the peaks of the first and second angled endothermic sections and in a solid-liquid phase-coexisting temperature range Tc between the rising start point in the first angled endothermic section and the dropping end point in the second angled endothermic section is in a range of RT≧69%.

If the second angled endothermic section has the gentle-sloping portion in the differential thermal analysis thermograph, and the proportion Rt (Td/Tc×100) of a peak-peak temperature range Td between the peaks of the first and second angled endothermic sections in the solid-liquid phase coexisting temperature range Tc is set in the above-described range, the temperature range permitting a liquid phase due to the eutectic melting to exist in the course of solidification is widened. Therefore, even when the alloy material is rapidly heated, it is possible to sufficiently flow the liquid phase between the solid phases, thereby uniformizing the distribution of the liquid phase.

Thus, even when the uniformization of heat in the semi-molten alloy material is not achieved due to the rapid heating, the fluidity of the material can be improved to enhance the moldability, and a casting having a uniform metallographic structure and a high fatigue strength can be produced. In this case, because the distribution of the liquid phase is uniformized, the solidification of the semi-molten alloy material is effected substantially over the whole thereof and therefore, the generation of shrinkage cavities is avoided.

However, if a gentle-sloping portion as described above does not exist in the differential thermal analysis thermograph, and Rt<69%, a casting produced through the rapid heating has a non-uniform metallographic structure.

Further, it is an object of the present invention to provide a producing process of the above-described type, wherein in subjecting the alloy material to a heating treatment, the average temperature rising rate can be controlled in correspondence to the thermal characteristic of the alloy material, thereby enabling the preparation of a semi-molten alloy material from which a casting having a sound casting quality can be obtained.

To achieve the above object, according to the present invention, there is provided a process for preparing a semi-molten alloy material for thixocasting having solid and liquid phases coexisting therein, comprising the step of heating an alloy material having such a characteristic that a first angled endothermic section generated by eutectic melting and a second angled endothermic section generated by melting of a segment having a melting point higher than the eutectic point exist in a differential thermal analysis thermograph, to a casting temperature laying between a dropping end point in the first angled endothermic section and a peak of the second angled endothermic section, wherein a ratio α/β between the following two average temperature rising rates α and β is set in a range of α/β1: (1) the average temperature rising rate α for the alloy material between a rising start point and the dropping end point in the first angled endothermic section, and (2) the average temperature rising rate β for the alloy material between the dropping end point and the casting temperature.

If the ratio α/β between the average temperature rising rates α and β is set in the range of α/β>1, the eutectic melting is performed at the relatively high average temperature rising rate α and therefore, the coalescence of the metallographic structure due to the growth and/or the coalescence of a primary crystal is suppressed. On the other hand, after the eutectic melting, the heating treatment advances at the relatively low average temperature rising rate β and therefore, the formation of a liquid phase of an eutectic segment is promoted, and the profile of temperature of the liquid phase is uniformized. Thus, it is possible to produce a casting having a sound casting quality.

However, if α/β≦1, the metallographic structure is liable to be coalesced due to the growth of the primary crystal or the like, and the profile of temperature of the liquid phase is liable to become non-uniform.

Further, the present inventors have made studies in order to solve the above-described problems in the thixocasting process, and as a result, they have found that the precipitation of a primary crystal of the alloy elements is caused by a high cooling rate during an eutectic reaction of the semi-molten alloy material.

The present invention has been accomplished with the result of the studies taken into account, and it is an object of the present invention to provide a thixocasting process of the above-described type, wherein the cooling rate during the eutectic reaction of the semi-molten alloy material can be reduced to avoid the precipitation of the primary crystal of the alloy elements, thereby producing a casting having a high ductility and a high toughness.

To achieve the above object, according to the present invention, there is provided a thixocasting process, using an alloy material in which in a differential thermal analysis thermograph, there exist a first angled endothermic section generated by eutectic melting and a second angled endothermic section generated by melting of a segment having a melting point higher than the eutectic point, wherein a casting temperature $T_6$ of the alloy material is set in a range of $T_7 \leq T_6 \leq T_5$, wherein $T_7$ represents a temperature at a dropping end point in the first angled endothermic section, and $T_5$ represents a peak temperature of the second angled endothermic section.

If the casting temperature $T_6$ of the alloy material is set in the above range, the alloy material is brought into a semi-molten state and moreover, the semi-molten alloy material has a lowered solid phase proportion. Namely, the liquid phase amount is relatively increased.

As a result, the cooling rate is lowered in the eutectic reaction of the semi-molten alloy material, because the relatively large amount of the liquid phase has a relatively large latent heat. This makes it possible to avoid the precipitation of a primary crystal of alloy elements.

A casting produced in this manner has a high ductility and a high toughness.

However, if the casting temperature $T_6$ is lower than $T_7$, the precipitation of the primary crystal of the alloy elements to occurs. On the other hand, if $T_6$->$T_5$, the shape retention of the semi-molten alloy material is reduced, resulting in a degraded handling ability thereof.

The above and other objects, features and advantages of the invention will become apparent from the following description of the preferred embodiments taken in conjunction with the accompanying drawings.

BRIEF DESCRIPTION OF THE DRAWINGS

FIG. 11A illustrates an essential portion of a differential thermal analysis thermograph for a comparative example a;

FIG. 11B is a photomicrograph showing the metallographic structure of an aluminum alloy casting a;

FIG. 19A illustrates an essential portion of a differential thermal analysis thermograph for a comparative example $a_3$;

FIG. 19B is a photomicrograph showing the metallographic structure of an aluminum alloy casting $a_3$;

FIG. 19C schematically illustrates a portion of the photomicrograph shown in FIG. 19B.

DESCRIPTION OF THE PREFERRED EMBODIMENTS

Figure 1:
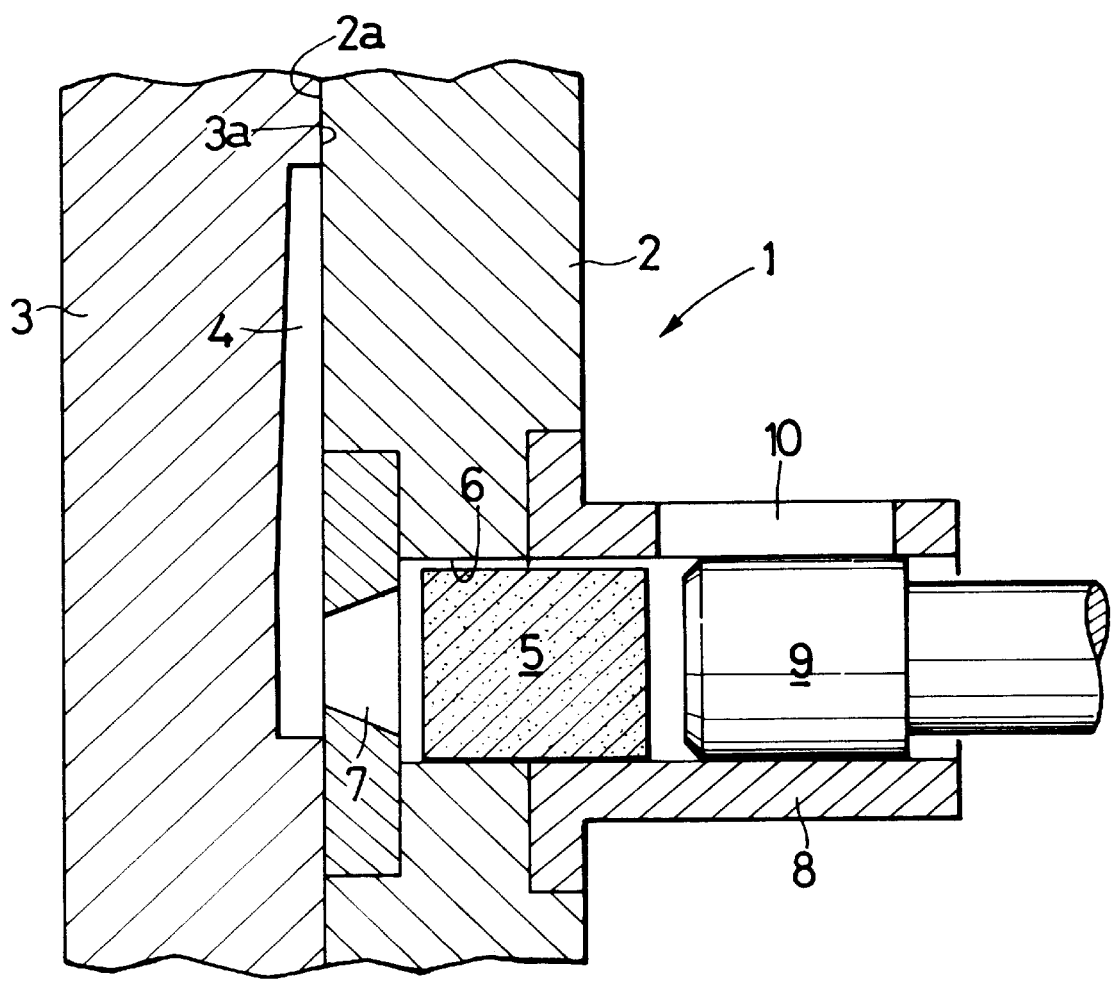
FIG. 1 is a vertical sectional view of a pressure casting apparatus.

Referring to FIG. 1, there is shown a pressure casting apparatus 1 used for producing an aluminum alloy casting in a thixocasting process using an aluminum alloy material. The pressure casting apparatus 1 includes a stationary die 2 and a movable die 3 having vertical matched faces 2a and 3a. A casting forming cavity 4 is defined between the matched faces 2a and 3a. A chamber 6 for placement of an aluminum alloy material 5 is defined in the stationary die 2 and communicates with a lower portion of the cavity 4 through a gate 7. A sleeve 8 is horizontally mounted on the stationary die 2 to communicate with the chamber 6, and a pressurizing plunger 9 is slidably received in the sleeve 8 and insertable into and removable from the chamber 6. The sleeve 8 has a material charging port 10 in an upper portion of a peripheral wall thereof.

Embodiment I

Example 1

In the example 1, a hypoeutectic Al-Cu based alloy material will be mainly described.

Figure 2:
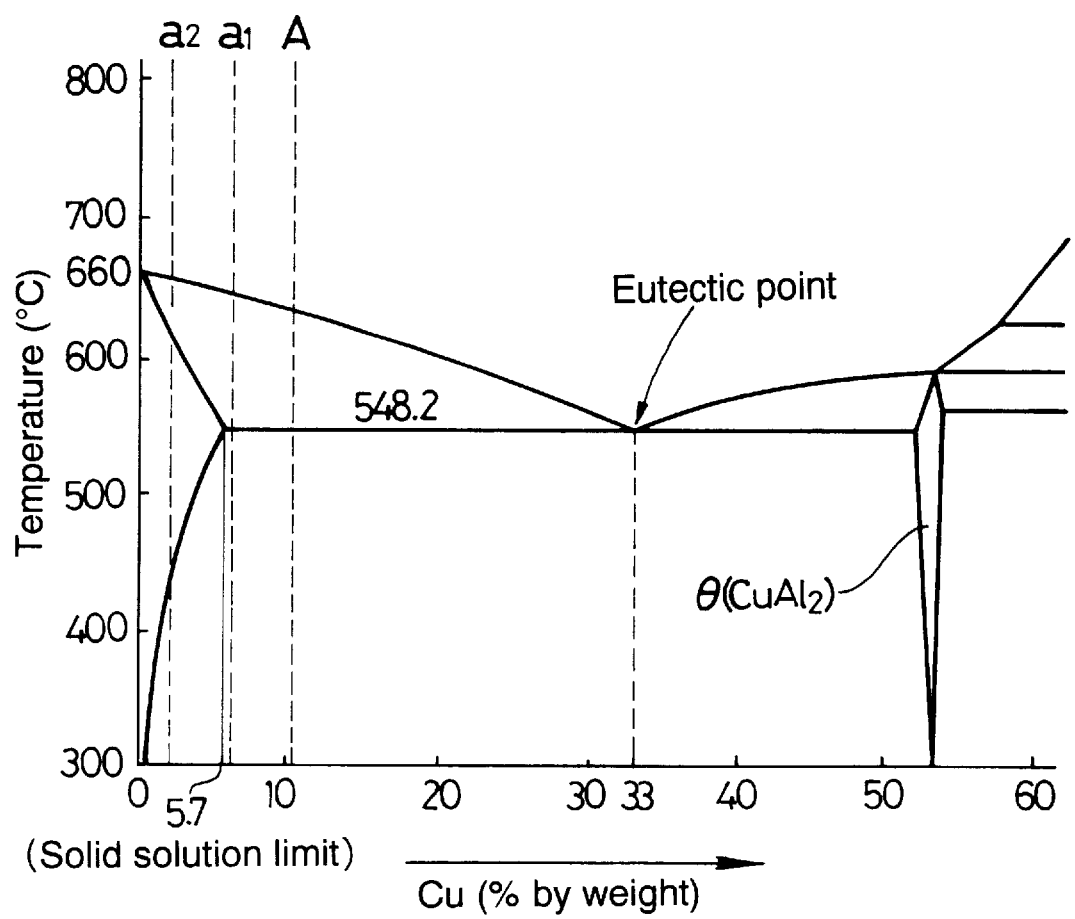
FIG. 2 is a phase diagram of an Al-Cu based alloy.

(A) FIG. 2 shows a phase diagram of an Al-Cu based alloy, and Table 1 shows compositions of an example A and comparative examples $a_1$ and $a_2$ of Al-Cu based alloy materials. In FIG. 2, A, $a_1$ and $a_2$ correspond to the example A and the comparative examples $a_1$ and $a_2$, respectively. Each of the example A and the comparative examples $a_1$ and $a_2$ was cut off from a high quality continuous casting produced in a continuous casting process. In producing the casting, a spheroidizing treatment of a primary crystal $\alpha$-Al was performed. Each of the example A and the comparative examples $a_1$ and $a_2$ has a diameter of 76 mm and a length of 85 mm.

TABLE 1

| | Chemical constituents (% by weight) | | | | | | | | | | |
|---|---|---|---|---|---|---|---|---|---|---|---|
| | Si | Cu | Mg | Fe | Zr | Zn | Mn | V | Ni | Ti | balance |
| Example A | 0.17 | 10.3 | — | 0.18 | 0.18 | — | 0.27 | 0.1 | — | 0.05 | Al |
| Comparative example $a_1$ | 0.17 | 6.3 | — | 0.19 | 0.08 | — | 0.28 | 0.11 | — | 0.05 | Al |
| Comparative example $a_2$ (2618 alloy) | 0.1~0.25 | 1.9~2.7 | 1.3~1.8 | 0.9~1.3 | — | <0.1 | — | — | 0.9~1.2 | 0.04~0.1 | Al |

Figure 3:
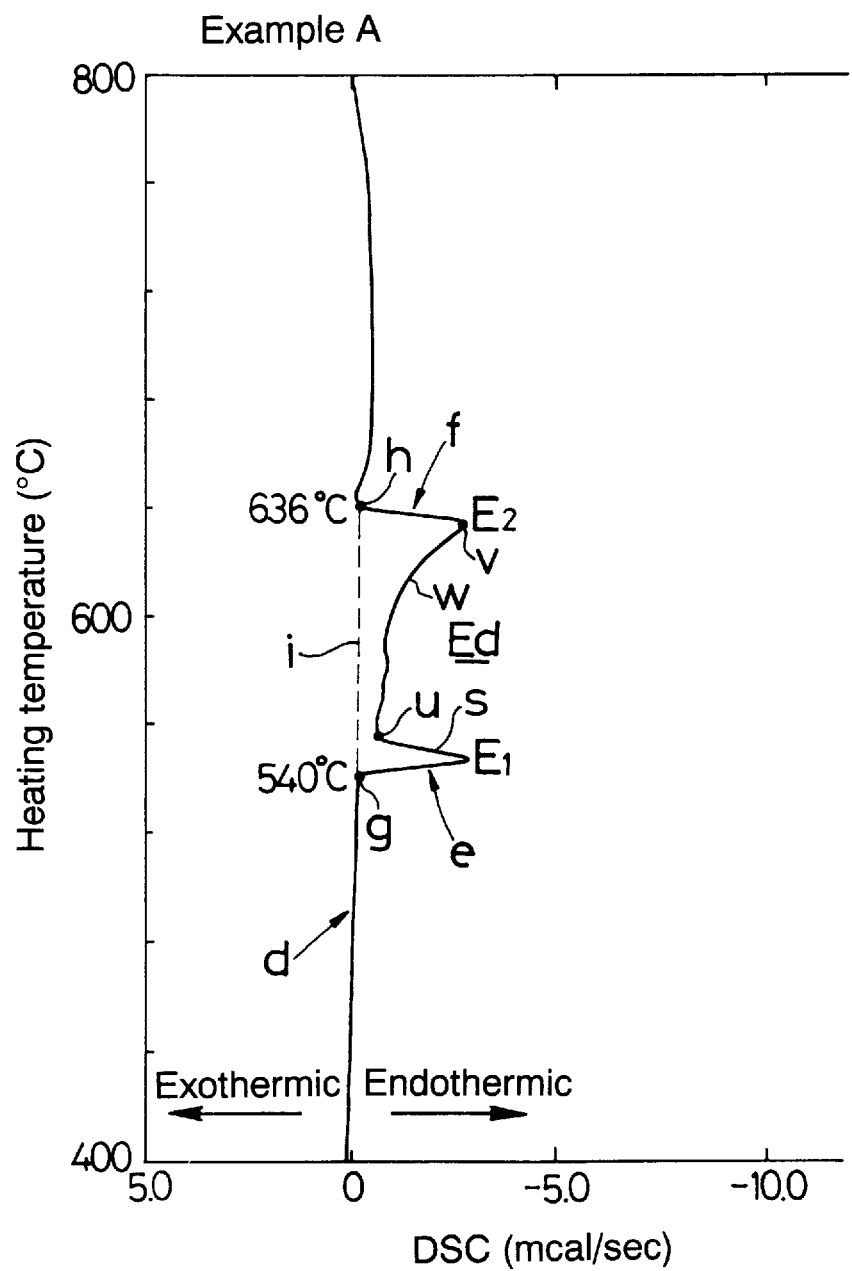
FIG. 3 is a differential thermal analysis thermograph for an example A.

The example A was subjected to a differential scanning calorimetry (DSC) to provide the result shown in FIG. 3. In the differential thermal analysis thermograph of FIG. 3, a peak value $E_1$ of a first angled endothermic section e due to an eutectic melting is equal to 2.7 mcal/sec, and a peak value $E_2$ of a second angled endothermic section f due to a melting of a segment having a melting point higher than an eutectic point is equal to 2.6 mcal/sec. It was confirmed from the above that $E_1 > E_2$. Likewise, the comparative examples $a_1$ and $a_2$ were subjected to the differential scanning calorimetry (DSC) to provide results which will be described hereinafter.

Then, the example A was placed into a heating coil in an induction heating device and then heated under conditions of a frequency of 1 kHz and a maximum output power of 37 kW to prepare a semi-molten example A having solid and liquid phases coexisting therein. In this case, the solid phase proportion was set in a range of 50% (inclusive) to 60% (inclusive).

Thereafter, the semi-molten example A (indicated by character 5 in FIG. 1) was placed into the chamber 6 and passed through the gate 7 and charged into the cavity 4, while being pressurized under conditions of a moving velocity of the pressurizing plunger 9 of 0.07 m/sec and a mold temperature of 250° C. A pressurizing force is applied to the example A fill in the cavity 4 by retaining the pressurizing plunger 9 at the terminate end of the stroke, and the example A was solidified under the pressurization to provide an aluminum alloy casting A. Aluminum alloy castings $a_1$ and $a_2$ were also produced in a similar casting manner using the comparative examples $a_1$ and $a_2$. FIGS. 4A and 4b to 6A and 6B show essential portions of differential thermal analysis thermographs for the example A and the comparative examples $a_1$ and $a_2$ and photomicrographs of the metallographic structures of the aluminum alloy castings A, $a_1$ and $a_2$.

Figure 4A:
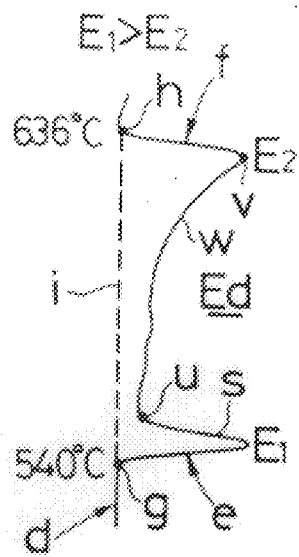
FIG. 4A illustrates an essential portion of the differential thermal analysis thermograph for the example A.
Figure 4B:
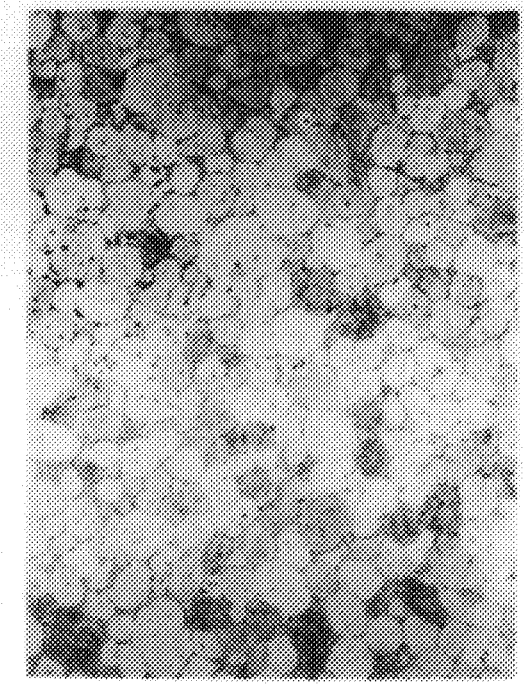
FIG. 4B is a photomicrograph showing the metallographic structure of an aluminum alloy casting A.

In the case of the example A, a relationship, $E_1 > E_2$ as described above was established between the peak values $E_1$ and $E_2$, as shown in FIG. 4A, and from this fact, no defect such as voids on the order of a micron was produced in the aluminum alloy casting A, as shown in FIG. 4B.

Figure 5A:
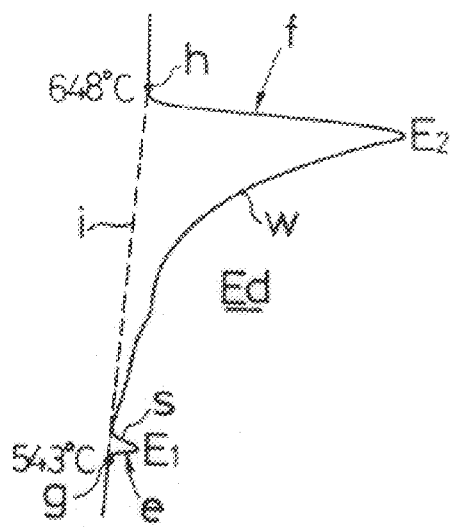
FIG. 5A illustrates an essential portion of a differential thermal analysis thermograph for a comparative example $a_1$.
Figure 5B:
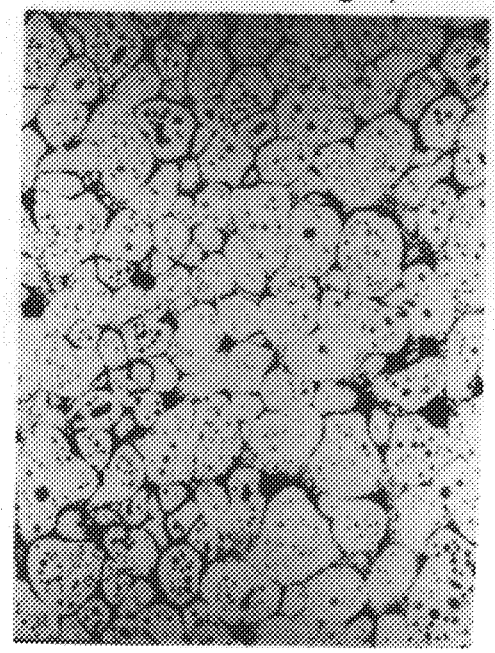
FIG. 5B is a photomicrograph showing the metallographic structure of an aluminum alloy casting $a_1$.

In the case of the comparative example $a_1$, the peak value $E_1$ of the first angle endothermic section e is equal to 0.61 mcal/sec, and the peak value $E_2$ of the second angle endothermic section f is equal to 5.6 mcal/sec, as shown in FIG. 5A, and hence, $E_1 < E_2$. Due to this, the latent heat of the liquid phase is lower than that of the example A. As a result, a large number of voids on the order of a micron were generated at boundaries between the granular solid phases in the aluminum alloy casting $a_1$, as shown in FIG. 5B.

Figure 6A:
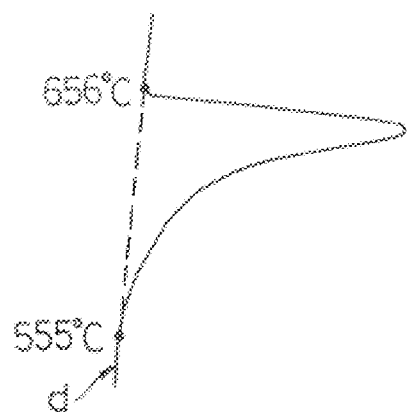
FIG. 6A illustrates an essential portion of a differential thermal analysis thermograph for a comparative example $a_2$.
Figure 6B:
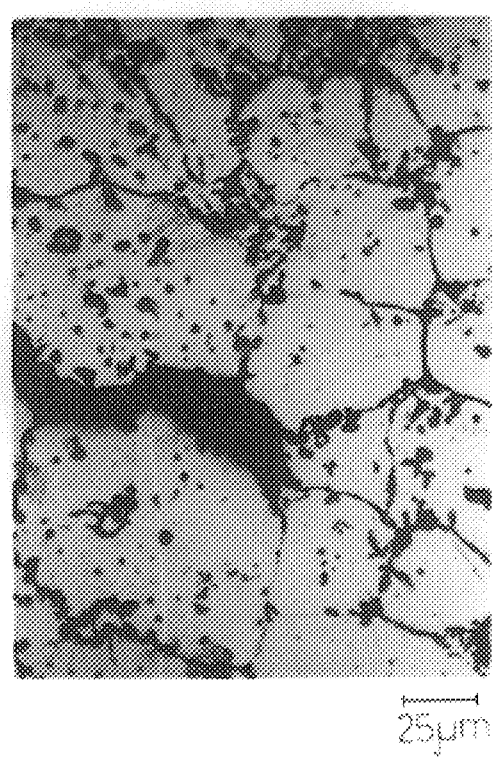
FIG. 6B is a photomicrograph showing the metallographic structure of an aluminum alloy casting $a_2$.

In the case of the comparative example $a_2$, an eutectic melting did not occur (see FIG. 2), as shown in FIG. 6A and hence, only one angled endothermic section was generated. Due to this, the latent heat of the liquid phase is low, as compared with the comparative example $a_1$ and as a result, relatively large voids were generated at boundaries between the granular solid phases in the aluminum alloy casting $a_2$, as shown in FIG. 6B.

(B) In a differential thermal analysis thermograph d shown in FIG. 3, a dropping line segment s of the first angled endothermic section e and a rising line segment w of the second angled endothermic section f are connected to each other in a region Ed of an endotherm higher than a basic line i which interconnects a rising start point g in the first angled endothermic section e and a dropping end point h in the second angled endothermic section f.

Figure 7:
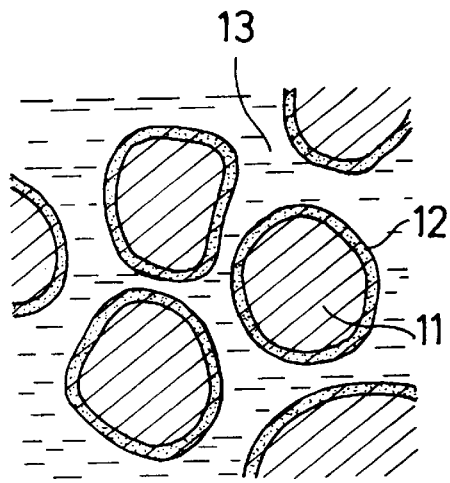
FIG. 7 is a diagram illustrating a semi-molten state of an example.

In the case of the example A such that a differential thermal analysis thermograph d is as described above, an outer periphery 12 of a solid phase 11 is gelled in the semi-molten state of the example A, as shown in FIG. 7, so that the compatibility between the gelled outer periphery 12 and a liquid phase 13 is improved. As a result, the strength of bonding between the granular solid phase which is a solidified phase derived from the solid phase 11 and a matrix which is a solidified phase derived from the solid phase 13, is increased in the aluminum alloy casting A, and thus, an increase in strength of the aluminum alloy casting A is achieved.

In the comparative example $a_1$, the dropping line segment s of the first angled endothermic section e and the rising line segment w of the second angled endothermic section f are connected to each other on the basic line i, as shown in FIG. 5A. In this case, the outer periphery of the solid phase is little gelled.

Then, using the example A and the comparative example $a_1$, five aluminum alloy castings A and $a_1$ were produced by a casting process similar to that described above and then subjected to a tensile test to provide results given in Table 2.

TABLE 2

| | Tensile strength (MPa) |
|---|---|
| Al alloy casting A | |
| No. 1 | 307 |
| No. 2 | 357 |
| No. 3 | 359 |
| No. 4 | 337 |
| No. 5 | 343 |
| Average tensile strength | 341 |
| Al alloy casting $a_1$ | |
| No. 1 | 289 |
| No. 2 | 251 |
| No. 3 | 301 |
| No. 4 | 274 |
| No. 5 | 212 |
| Average tensile strength | 265 |

It can be seen from Table 2 that the aluminum alloy casting A produced using the example A has a high strength, as compared with the aluminum alloy casting $a_1$ produced using the comparative example $a_1$. In place of the gelling of the outer periphery 12 of the solid phase 11, a segment, which can be deposited on the solid phase and gelled in the above-described situation, may be contained in a material.
(C) In the differential thermal analysis thermograph d as shown in FIG. 3, the gradient of the rising line segment of the second angled endothermic section f is gentler than the second angled endothermic section f is gentler than that of the dropping line segment s of the first angled endothermic section e.

In the case of the example A such that a differential thermal analysis thermograph d is as described above, the acceptable range of the casting temperature is widened, because the range of the casting temperature is set from a dropping end point u of the first angled endothermic section e to a peak v of the second angled endothermic section f. Thus, it is possible to stabilize the casting quality of an aluminum alloy casting.

Example 2

In this example 2, a hypoeutectic Al-Si based alloy material will be mainly described.

Figure 8:
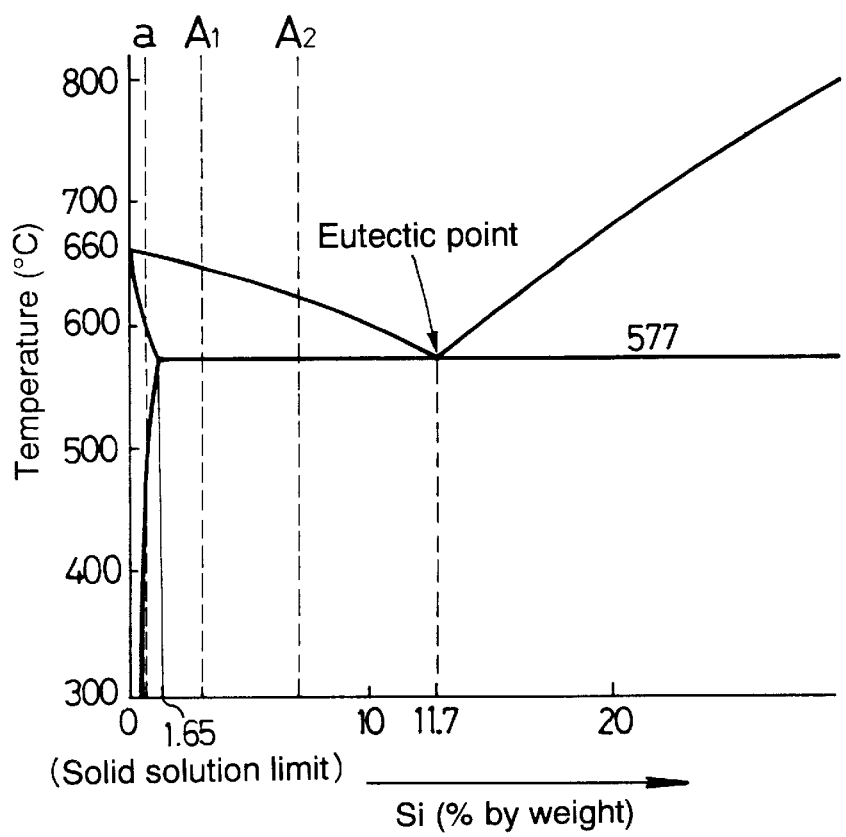
FIG. 8 is a phase diagram of an Al-Si based alloy.

FIG. 8 shows a phase diagram of an Al-Si base alloy, and Table 3 shows compositions of examples $A_1$ and $A_2$ and a comparative example a of Al-Si based alloy materials. In FIG. 8, reference characters $A_1$, $A_2$ and a correspond to the examples $A_1$ and $A_2$ and the comparative example a, respectively. Each of the examples $A_1$ and $A_2$ and the comparative example a was cut off from a high quality long continuous casting produced in a continuous casting process. In producing the casting, a spheroidizing treatment of a primary crystal α-Al was performed. Each of the examples $A_1$ and $A_2$ and the comparative example a has a diameter of 76 mm and a length of 85 mm.

Thereafter, the semi-molten example $A_1$ (indicated by character 5 in FIG. 1) was placed into the chamber 6 and passed through the gate 7 and charged into the cavity 4, while being pressurized under conditions of a moving velocity of the pressurizing plunger 9 of 0.07 m/sec and a mold temperature of 250° C. A pressurizing force is applied to the example $A_1$ fill in the cavity 4 by retaining the pressurizing plunger 9 at the terminate end of the stroke, and the example $A_1$ was solidified under the pressurization to provide an aluminum alloy casting $A_1$. Aluminum alloy castings $A_2$ and a were also produced in a similar casting manner using the example $A_2$ and the comparative example a.

Figure 9A:
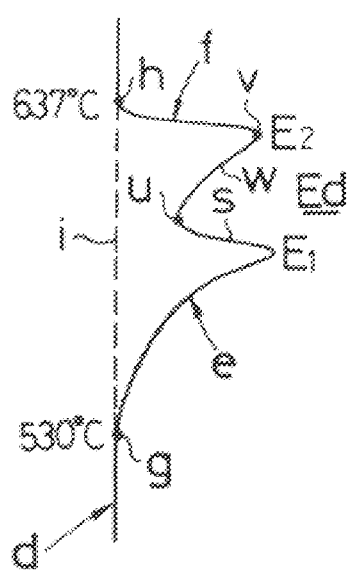
FIG. 9A illustrates an essential portion of the differential thermal analysis thermograph for the example $A_1$.
Figure 9B:
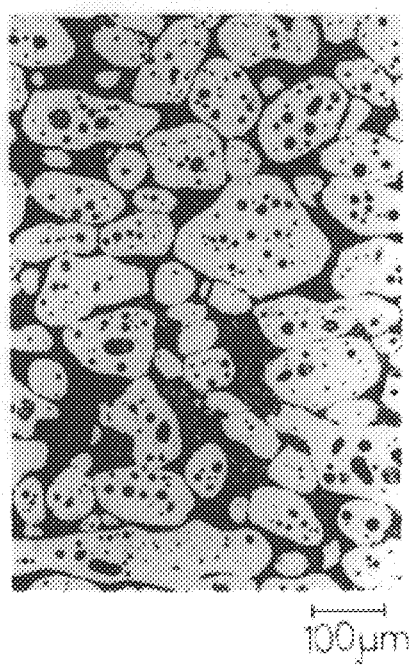
FIG. 9B is a photomicrograph showing the metallographic structure of an aluminum alloy casting $A_1$.
Figure 10A:
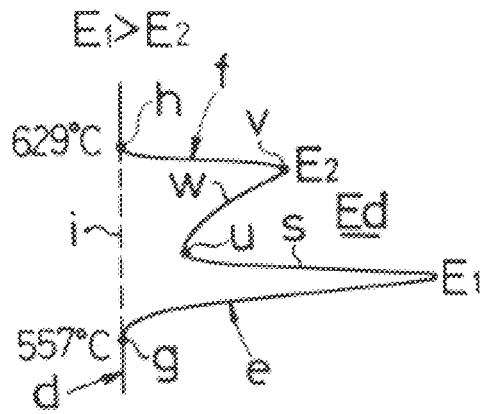
FIG. 10A illustrates an essential portion of the differential thermal analysis thermograph for the example $A_2$.
Figure 10B:
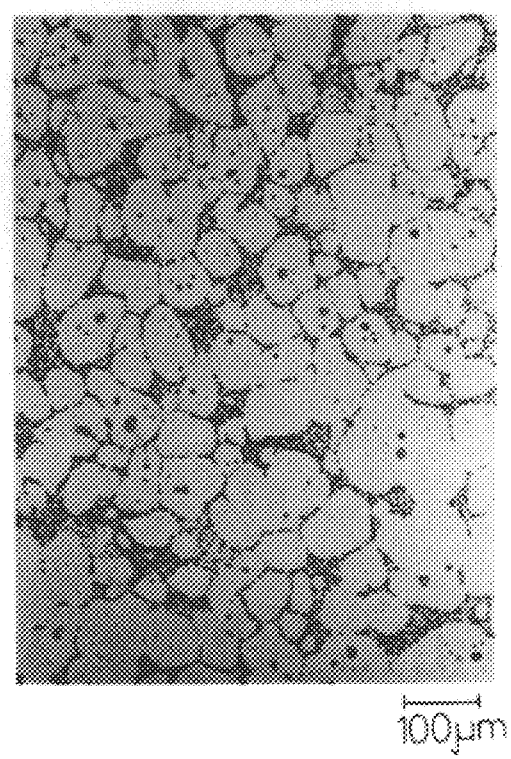
FIG. 10B is a photomicrograph showing the metallographic structure of an aluminum alloy casting $A_2$.
Figure 11A:
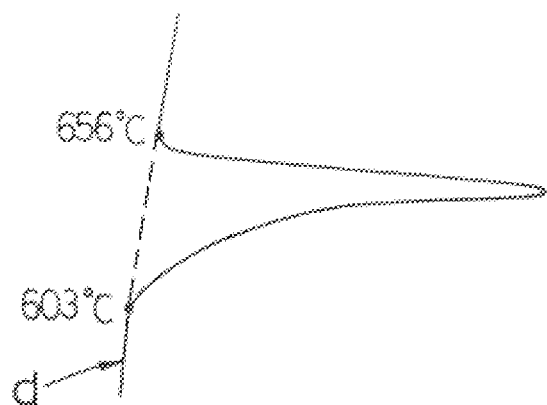

FIGS. 10A and 11A show essential portions of differential thermal analysis thermographs d for the example $A_2$ and the comparative example a, and FIGS. 9B to 11B show photomicrographs of the metallographic structures of the aluminum alloy castings $A_1$, $A_2$ and a.

In the case of the example $A_1$, a relationship $E_1 > E_2$ as described above was established between the peak values $E_1$ and $E_2$, as shown in FIG. 9A, and from this fact, no defect such as voids on the order of a micron was produced in the aluminum alloy casting $A_1$, as shown in FIG. 9B.

In the case of the example $A_1$, the peak value $E_1$ of the first angled endothermic section e is equal to 9.1 mcal/sec, and the peak value $E_2$ of the second angled endothermic section f is equal to 4.5 mcal/sec, as shown in FIG. 10A, and hence, $E_1 > E_2$. Thus, the aluminum alloy casting $A_2$ is sound, as shown in FIG. 10B.

Figure 11B:
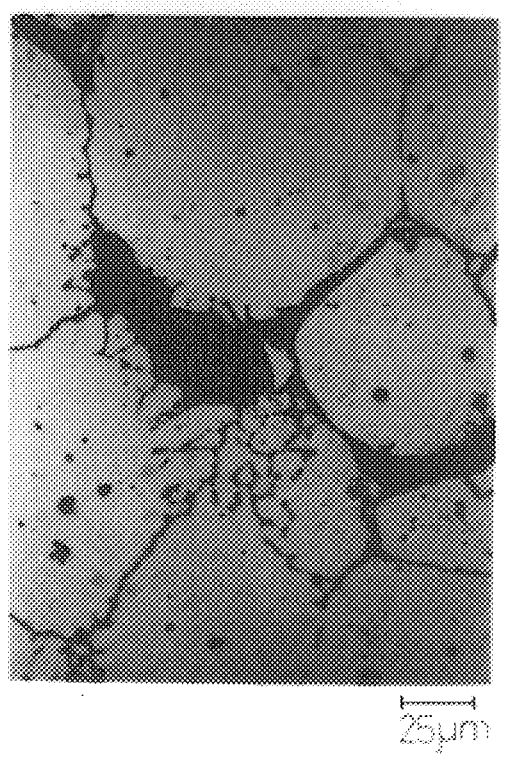

In the case of the comparative example a, an eutectic melting did not occur (see FIG. 8), as shown in FIG. 6A and hence, only one angled endothermic section was generated. Due to this, the latent heat of the liquid phase is extremely low and as a result, relatively large voids were generated at boundaries between the granular solid phases in the aluminum alloy casting a, as shown in FIG. 11B.

TABLE 3

| | Chemical constituents (% by weight) | | | | | | | | | |
|---|---|---|---|---|---|---|---|---|---|---|
| | Si | Cu | Mg | Fe | Zr | Zn | Mn | V | Ni | Ti | balance |
| Example $A_1$ | 2.58 | 2.0 | 4.0 | 0.13 | 0.02 | — | 0.01 | — | — | 0.03 | Al |
| Example $A_2$ | 6.5~7.5 | <0.2 | 0.4~0.7 | <0.2 | — | — | — | — | — | 0.04~0.20 | Al |
| Comparative example a (6061 alloy) | 0.4~0.8 | 0.15~0.4 | 0.8~1.2 | <0.7 | — | <0.25 | <0.15 | — | — | <0.15 | Al |

The example $A_1$ was subjected to a differential scanning calorimetry (DSC) to provide the result shown in FIG. 9A. In the differential thermal analysis thermograph of FIG. 9A, a peak value $E_1$ of a first angled endothermic section e due to an eutectic melting is equal to 3.2 mcal/sec, and a peak value $E_2$ of a second angled endothermic section f due to a melting of a segment having a melting point higher than an eutectic point is equal to 2.9 mcal/sec. It was confirmed from the above that $E_1 > E_2$. Likewise, the example $A_2$ and the comparative example a were subjected to a similar differential scanning calorimetry (DSC) to provide results which will be described hereinafter.

Then, the example $A_1$ was placed into the heating coil in the induction heating device and then heated under conditions of a frequency of 1 kHz and a maximum output power of 37 kW to prepare a semi-molten example $A_1$ having solid and liquid phases coexisting therein. In this case, the solid phase proportion was set in a range of 50% (inclusive) to 60% (inclusive).

The same description as in the items (B) and (C) in Example 1 is true of the Al-Si based alloy of this example.

Embodiment II

Table 4 shows compositions of examples $A_1$ to $A_4$ and comparative examples $a_1$ to $a_5$. Each of these examples and comparative examples was cut off from a high quality long continuous casting produced in a continuous casting process. In producing the casting, a spheroidizing treatment of a primary crystal α-Al was performed. Each of the examples and the comparative examples has a diameter of 50 mm and a length of 65 mm.

TABLE 4

| Al alloy material | Chemical constituents (% by weight) | | | | | | | | | | |
|---|---|---|---|---|---|---|---|---|---|---|---|
| | Si | Cu | Mg | Fe | Zr | Zn | Mn | V | Ni | Ti | balance |
| Example $A_1$ | 0.17 | 10.3 | — | 0.18 | 0.18 | — | 0.27 | 0.1 | — | 0.05 | Al |
| Example $A_2$ | 5 | 3 | 0.32 | 0.19 | — | 0.19 | 0.09 | — | 0.09 | 0.12 | Al |
| Example $A_3$ | 7 | 0.19 | 0.55 | 0.19 | — | 0.09 | 0.09 | — | — | 0.12 | Al |
| Example $A_4$ | 7 | 0.19 | 0.35 | 0.19 | — | 0.09 | 0.09 | — | — | 0.19 | Al |
| Comparative example $a_1$ (A204 material) | 0.18 | 4.6 | 0.25 | 0.34 | — | 0.09 | 0.09 | — | 0.04 | 0.22 | Al |
| Comparative example $a_2$ | 0.17 | 6.3 | — | 0.19 | 0.08 | — | 0.28 | 0.11 | — | 0.05 | Al |
| Comparative example $a_3$ (A390 material) | 16.5 | 4.5 | 0.55 | 0.4 | — | 0.09 | 0.09 | — | — | 0.19 | Al |
| Comparative example $a_4$ (2618 material) | 0.17 | 2.3 | 1.55 | 1.1 | — | 0.09 | — | — | 1.05 | 0.07 | Al |
| Comparative example $a_5$ (6061 material) | 0.6 | 0.27 | 1.1 | 0.6 | — | 0.24 | 0.14 | — | — | 0.14 | Al |

Figure 12:
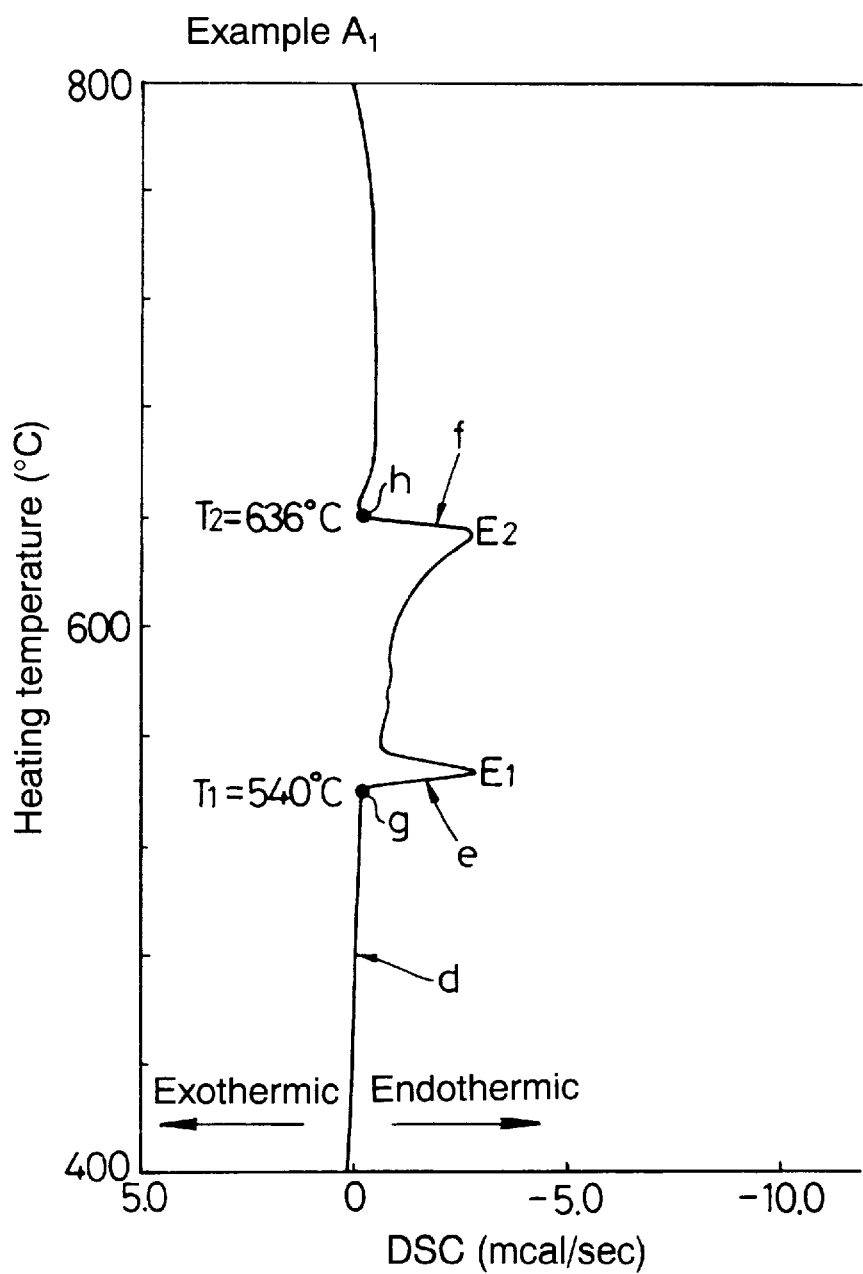
FIG. 12 is a differential thermal analysis thermograph for an example $A_1$.

The example $A_1$ was subjected to a differential scanning calorimetry (DSC) to provide the result shown in FIG. 12. In the differential thermal analysis thermograph d of FIG. 12, a peak value $E_1$ of a first angled endothermic section e due to an eutectic melting is equal to 2.7 mcal/sec, and a peak value $E_2$ of a second angled endothermic section f due to a melting of a segment having a melting point higher than an eutectic point is equal to 2.6 mcal/sec. It was confirmed from the above that the ratio $E_1/E_2$ of the peak values $E_1$ and $E_2$ is equal to 1.04.

On the other hand, in the differential thermal analysis thermograph d, a temperature $T_1$ of a rising start point g of the first angled endothermic section e is equal to 540° C., and a temperature $T_2$ of a dropping end point h of the second angled endothermic section f is equal to 636° C. From this, it was confirmed that a difference $T_2-T_1$ between the temperatures $T_1$ and $T_2$ was equal to 96° C.

Then, the example $A_1$ was placed into the heating coil in the induction heating device and then heated under conditions of a frequency of 1 kHz and a maximum output power of 37 kW to prepare a semi-molten example $A_1$ having solid and liquid phases coexisting therein. In this case, the solid phase proportion was set in a range of 50% (inclusive) to 60% (inclusive).

Thereafter, the semi-molten example $A_1$ (indicated by character 5 in FIG. 1) was placed into the chamber 6 and passed through the gate 7 and charged into the cavity 4, while being pressurized under conditions of a moving velocity of the pressurizing plunger 9 of 0.07 m/sec and a mold temperature of 250° C. A pressurizing force is applied to the example $A_1$ fill in the cavity 4 by retaining the pressurizing plunger 9 at the terminate end of the stroke, and the example $A_1$ was solidified under the pressurization to provide an aluminum alloy casting $A_1$.

Each of the examples $A_2$ to $A_4$ and the comparative examples $a_1$ to $a_5$ was subjected to the DSC, and using them, eight aluminum alloy castings $A_2$ to $A_4$ and $a_1$ to $a_5$ were produced in the same casting process.

Table 5 shows the peak values $E_1$ and $E_2$, the ratio $E_1/E_2$, the temperature $T_1$ at the rising start point g, the temperature $T_2$ at the dropping end point h, the difference $T_2-T_1$ between the temperatures $T_1$ and $T_2$, the casting temperature for the examples $A_1$ to $A_4$ and the comparative examples $a_1$ to $a_5$, and the presence or absence of defects in the produced aluminum alloy castings.

TABLE 5

| Al alloy material | Peak value (mcal/sec) | | Ratio | Temperature $T_1$ at rising starting point (°C.) | Temperature $T_2$ at dropping end point (°C.) | Difference $T_2-T_1$ (°C.) | Casting temperature (°C.) | Presence of absence of defects | |
|---|---|---|---|---|---|---|---|---|---|
| | $E_1$ | $E_2$ | $E_1/E_2$ | | | | | Voids | Segregation |
| Example $A_1$ | 2.7 | 2.6 | 1.04 | 540 | 636 | 96 | 615 | absence | absence |
| Example $A_2$ | 4.2 | 3.5 | 1.2 | 535 | 630 | 95 | 594 | absence | absence |
| Example $A_3$ | 10.4 | 5.2 | 2 | 557 | 629 | 72 | 588 | absence | absence |
| Example $A_4$ | 7.3 | 2.9 | 2.5 | 566 | 627 | 61 | 590 | absence | absence |
| Comparative example $a_1$ | 1.8 | 9.2 | 0.2 | 572 | 657 | 85 | 638 | presence | absence |
| Comparative example $a_2$ | 0.6 | 5.6 | 0.1 | 543 | 648 | 105 | 620 | presence | absence |
| Comparative example $a_3$ | 5.9 | 0.25 | 24 | 507 | 650 | 143 | 560 | presence | presence |

TABLE 5-continued

| Al alloy material | Peak value (mcal/sec) $E_1$ | $E_2$ | Ratio $E_1/E_2$ | Temperature $T_1$ at rising starting point (°C.) | Temperature $T_2$ at dropping end point (°C.) | Difference $T_2-T_1$ (°C.) | Casting temperature (°C.) | Presence of absence of defects Voids | Segregation |
|---|---|---|---|---|---|---|---|---|---|
| Comparative example $a_4$ | 0 | 10.0 | 0 | — | — | — | 628 | presence | absence |
| Comparative example $a_5$ | 0 | 12.1 | 0 | — | — | — | 639 | presence | absence |

Figure 13:
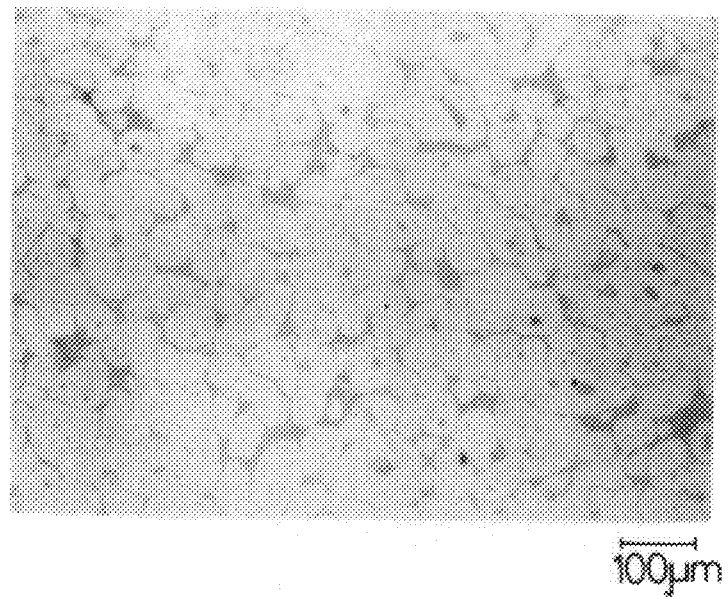
FIG. 13 is a photomicrograph showing the metallographic structure of an aluminum alloy casting $A_1$.
Figure 14A:
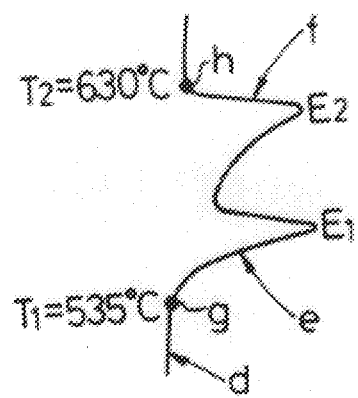
FIG. 14A illustrates an essential portion of a differential thermal analysis thermograph for an example $A_2$.
Figure 14B:
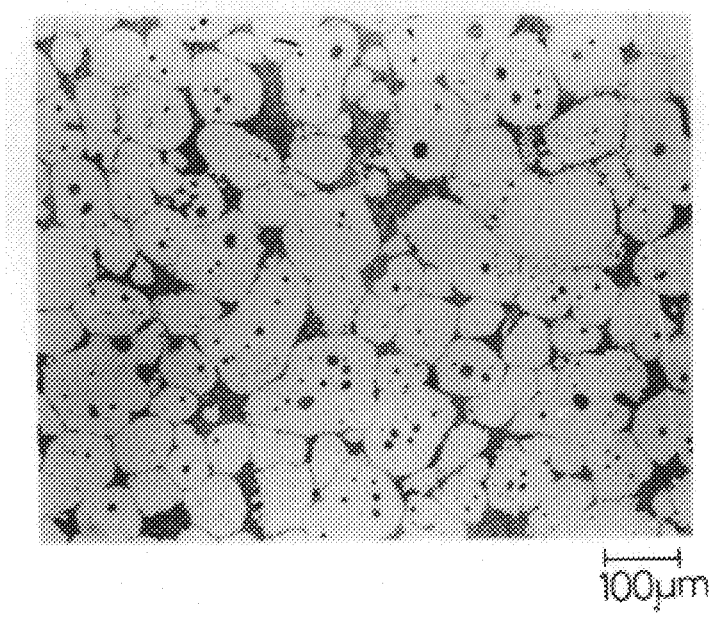
FIG. 14B is a photomicrograph showing the metallographic structure of an aluminum alloy casting $A_2$.
Figure 15A:
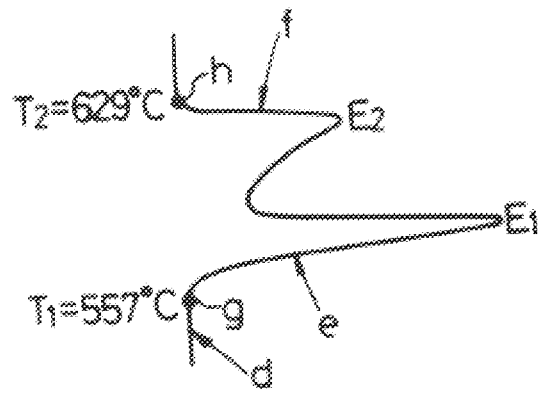
FIG. 15A illustrates an essential portion of a differential thermal analysis thermograph for an example $A_3$.
Figure 15B:
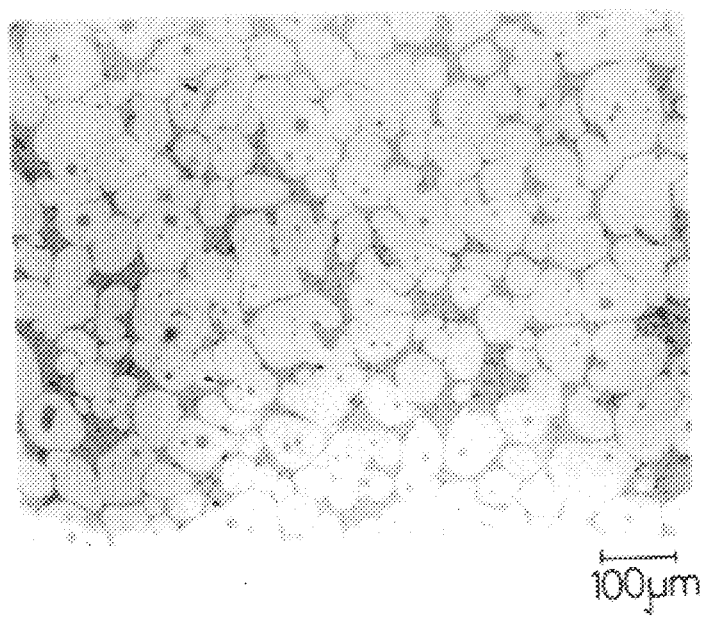
FIG. 15B is a photomicrograph showing the metallographic structure of an aluminum alloy casting $A_3$.
Figure 16A:
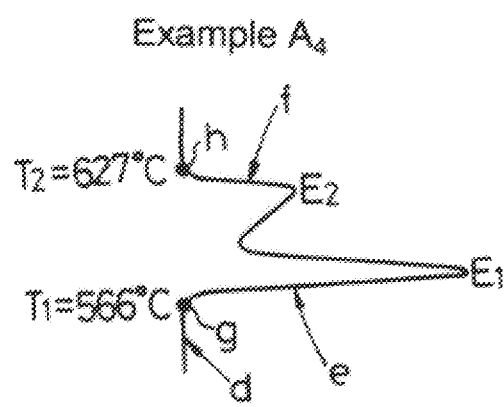
FIG. 16A illustrates an essential portion of a differential thermal analysis thermograph for an example $A_4$.
Figure 16B:
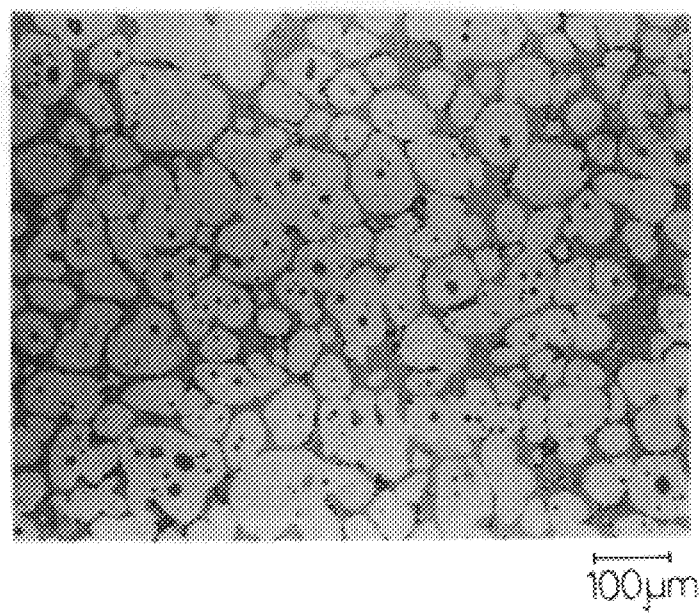
FIG. 16B is a photomicrograph showing the metallographic structure of an aluminum alloy casting $A_4$.
Figure 17A:
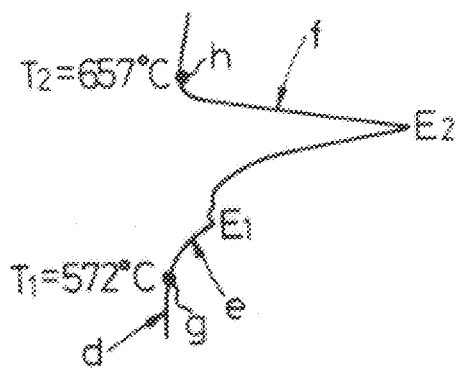
FIG. 17A illustrates an essential portion of a differential thermal analysis thermograph for a comparative example $a_1$.
Figure 17B:
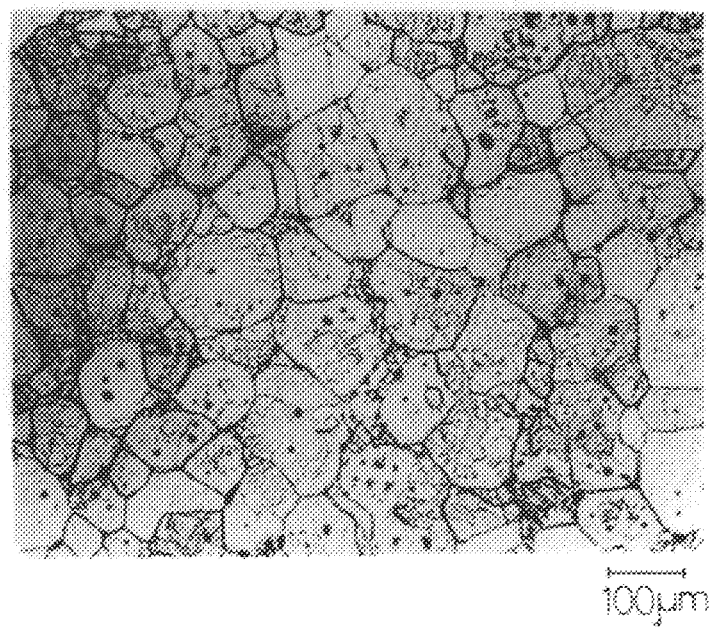
FIG. 17B is a photomicrograph showing the metallographic structure of an aluminum alloy casting $a_1$.

FIG. 13 is a photomicrograph showing the metallographic structure of the aluminum alloy casting $A_1$. FIGS. 14A to 16A show essential portions of differential thermal analysis thermographs d for the examples $A_2$ to $A_4$, and FIGS. 14B to 16B are photomicrographs showing the metallographic structures of the aluminum alloy castings $A_2$ to $A_4$ produced using the examples $A_2$ to $A_4$.

As can be seen from Table 5 and FIGS. 14A to 16B, the ratio $E_1/E_2$ is in a range of $1<E_1/E_2<2.5$, and the temperature difference $T_2-T_1$ is in a range of $10°$ C.$<T_2-T_1<120°$ C., in each of the examples $A_1$ to $A_4$. Therefore, because the liquid phase had a large latent heat, the liquid phase was sufficiently fed around the solid phase in response to the solidification and shrinkage of the solid phase, and the outer periphery 12 of the solid phase was gelled, so that the compatibility between the gelled outer periphery 12 and the liquid phase 13 was improved. Thus, no defects such as voids on the order of a micron were produced in each of these aluminum alloy castings $A_l$ to $A_4$.

FIGS. 17A to 21A show essential portions of differential thermal analysis thermographs d for the examples $A_2$ to $A_4$, and FIGS. 17B to 21B are photomicrographs showing the metallographic structures of the aluminum alloy castings $a_1$ to $a_5$ produced using the comparative examples $a_1$ to $a_5$.

Figure 18:
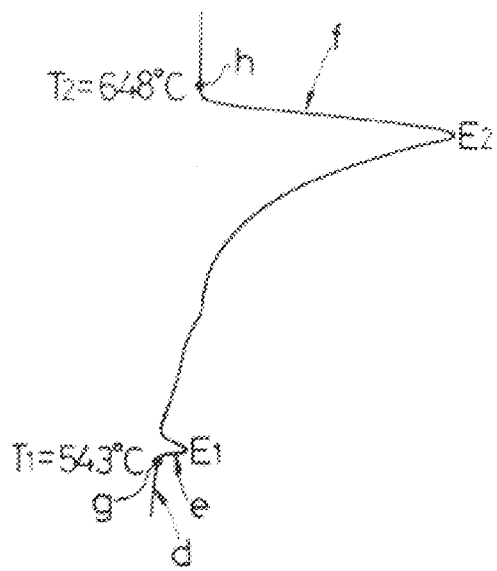
FIG. 18A illustrates an essential portion of a differential thermal analysis thermograph for a comparative example $a_2$.
FIG. 18B is a photomicrograph showing the metallographic structure of an aluminum alloy casting $a_2$.
Figure 18B:
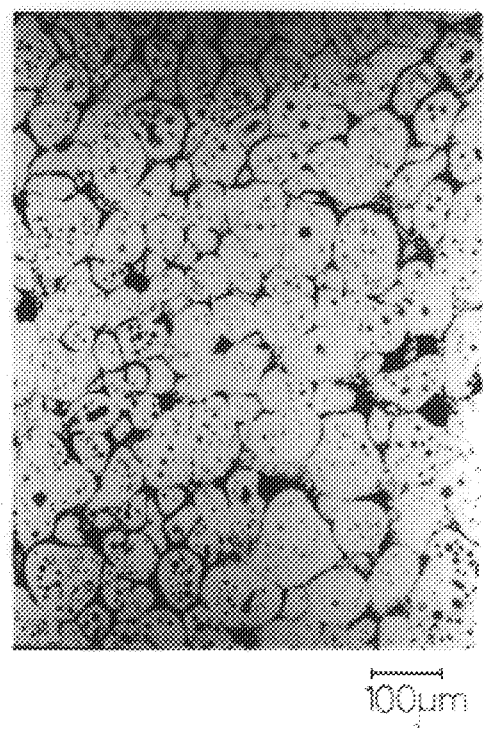
Figure 20A:
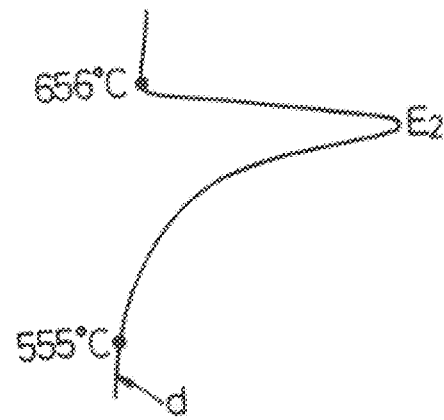
FIG. 20A illustrates an essential portion of a differential thermal analysis thermograph for a comparative example $a_4$.
Figure 20B:
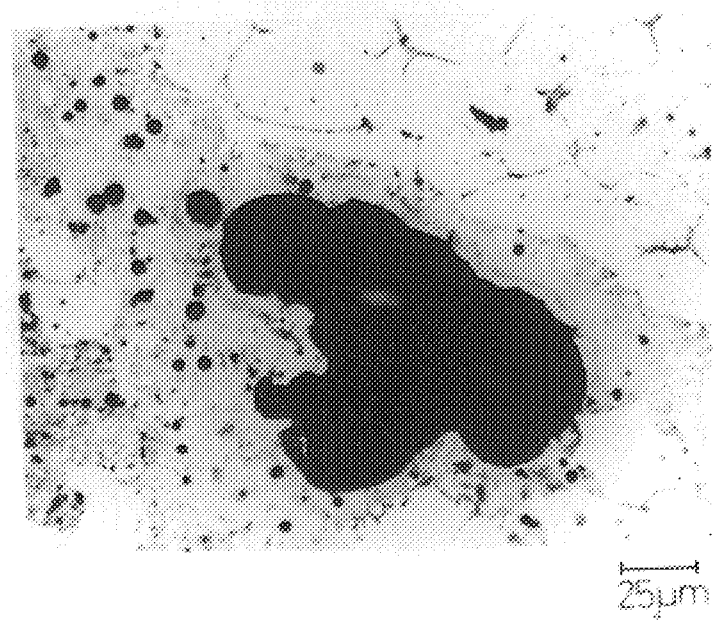
FIG. 20B is a photomicrograph showing the metallographic structure of an aluminum alloy casting $a_4$.
Figure 21A:
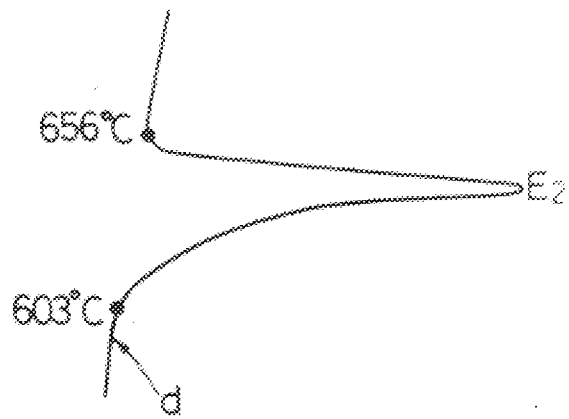
FIG. 21A illustrates an essential portion of a differential thermal analysis thermograph for a comparative example $a_5$.
Figure 21B:
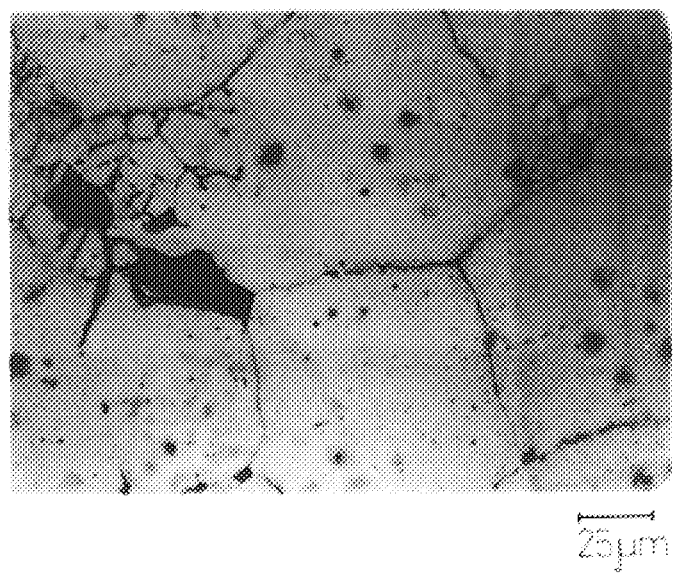
FIG. 21B is a photomicrograph showing the metallographic structure of an aluminum alloy casting $a_5$.

As can be seen from Table 5, both required conditions for the ratio $E_1/E_2$ and the temperature difference $T_2-T_1$ were not satisfied. Due to this, voids on the order of a micron (black portions) were generated at boundaries in each of the aluminum alloy castings $a_1$, $a_2$, $a_4$ and $a_5$, as shown in FIGS. 18B, 20B and 21B. In the aluminum alloy casting $a_3$, the segregation and coalescence of a fine piece-like deep gray primary crystal Si were generated, as shown in FIG. 19B, because the ratio $E_1/E_2$ was equal to or greater than 2.5 and moreover, black shrinkage cavities were produced, as shown in FIG. 19B, because the temperature difference $T_2-T_1$ was too high. This is also apparent from FIG. 19C.

Then, each of the aluminum alloy castings $A_1$ to $A_4$ and $a_1$ to $a_5$ was subjected to a T6 treatment under conditions shown in Table 6.

TABLE 6

| | T6 treatment | | | | |
|---|---|---|---|---|---|
| | Solution treatment | | | Aging treatment | |
| Al alloy casting | Temperature (°C.) | Time (hr) | Cooling type | Temperature (°C.) | Time (hr) |
| $A_1$ | 525 | 5 | water cooling | 190 | 18 |
| $A_2$ | 515 | 5 | | 170 | 10 |
| $A_3$ | 540 | 5 | | 170 | 5 |
| $A_4$ | 540 | 5 | | 170 | 5 |
| $a_1$ | 525 | 6 | water | 190 | 5 |

TABLE 6-continued

| | T6 treatment | | | | |
|---|---|---|---|---|---|
| | Solution treatment | | | Aging treatment | |
| Al alloy casting | Temperature (°C.) | Time (hr) | Cooling type | Temperature (°C.) | Time (hr) |
| $a_2$ | 525 | 5 | cooling | 190 | 18 |
| $a_3$ | 490 | 5 | | 175 | 8 |
| $a_4$ | 520 | 6 | | 185 | 10 |
| $a_5$ | 530 | 5 | | 175 | 8 |

For the purpose of carrying out a fatigue test, six test pieces each including a parallel portion having a diameter of 4 mm and a length of 20 mm were fabricated from each of the aluminum alloy castings $A_1$ to $A_4$ and $a_1$ to $a_5$ resulting from the T6 treatment. These test pieces were subjected to a test with different stress amplitudes using an electric hydraulic fatigue tester to determine the number of repetitions up to the fracture. From this data, the fatigue strength at $10^7$ repetitions was determined. Table 7 shows the results.

TABLE 7

| | | Fatigue strength (MPa) |
|---|---|---|
| Al alloy casting | $A_1$ | 120 |
| | $A_2$ | 140 |
| | $A_3$ | 120 |
| | $A_4$ | 120 |
| Al alloy casting | $a_1$ | 90 |
| | $a_2$ | 95 |
| | $a_3$ | 80 |
| | $a_4$ | 80 |
| | $a_5$ | 70 |

Figure 22:
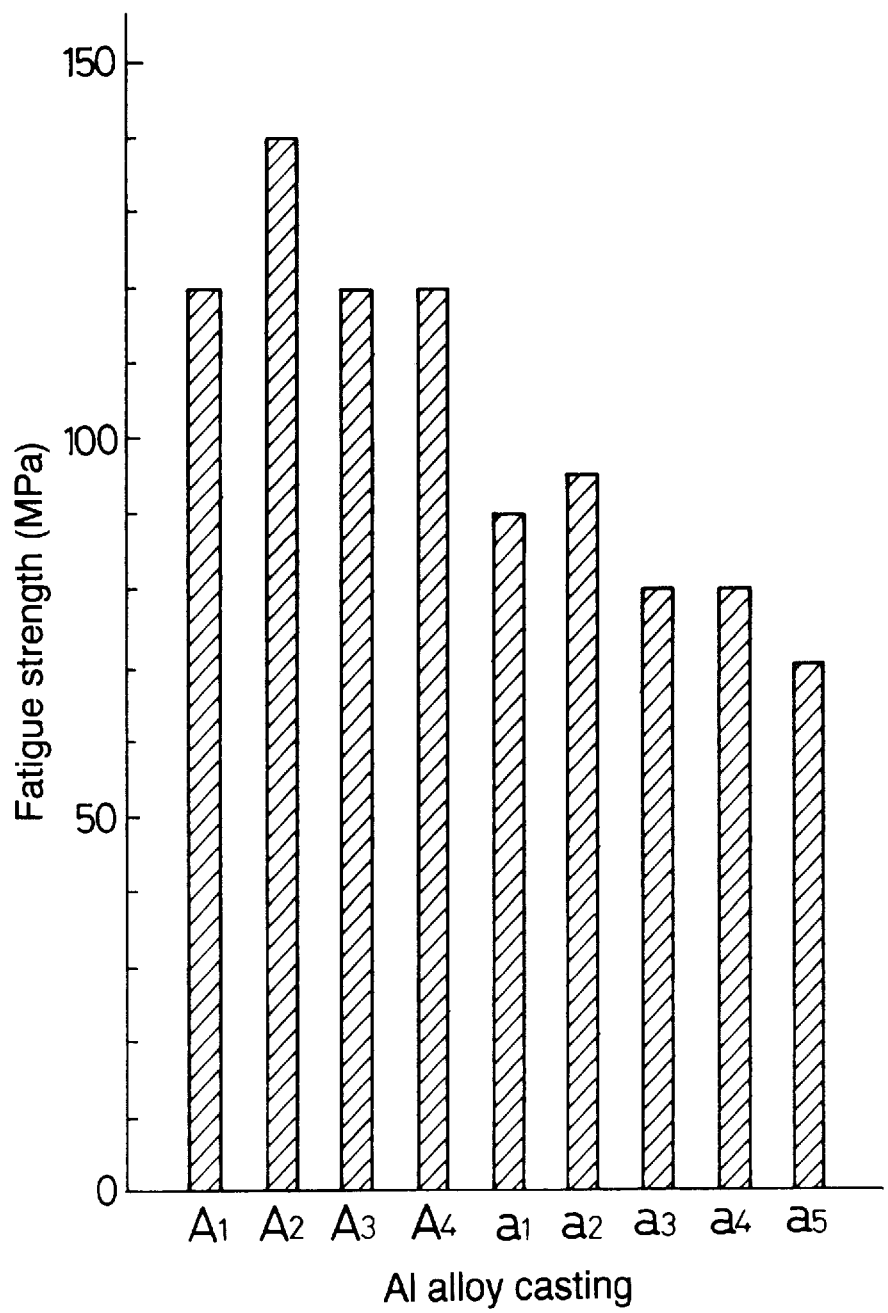
FIG. 22 is a graph illustrating fatigue strengths of various aluminum alloy castings.

FIG. 22 is a graph illustrating the fatigue strengths of the aluminum alloy castings $A_1$ to $A_4$ and $a_1$ to $a_5$ shown in Table 7.

As can be seen from Table 7 and FIG. 22, each of the aluminum alloy castings $A_1$ to $A_4$ produced in the thixocasting process using the examples $A_1$ to $A_4$ of the aluminum alloy materials has a fatigue strength higher than those of the aluminum alloy castings $a_1$ to $a_5$ produced using the comparative examples $a_1$ to $a_5$ of the aluminum alloy materials. Form this fact, it was found that the examples $A_1$ to $A_4$ are suitable as thixocasting aluminum alloy materials.

Embodiment III

Figure 23:
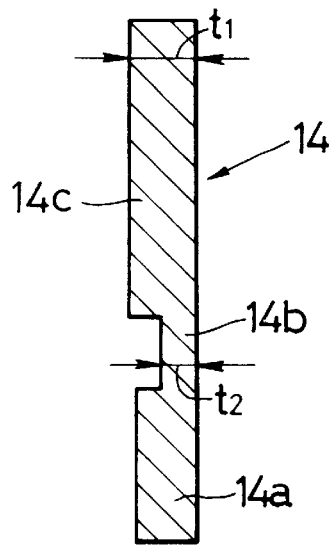
FIG. 23 is a sectional view of an aluminum alloy casting.

An aluminum alloy casting 14 shown in FIG. 23 is produced in a thixocasting process using an aluminum alloy material. The aluminum alloy casting 14 includes a medium-thickness portion 14a which is to be connected to a gate 7 of a pressure casting apparatus 1, a thinner portion 14b connected to the medium-thickness portion 14a and having a relatively small volume, and a thicker portion 14c connected to the thinner portion 14b and having a relatively large volume. If the thickness of the thicker portion 14c is represented by $t_1$, and the thickness of the thinner portion 14b is represented by $t_2$, a relationship, $t_1=2\ t_2$ is established.

Figure 24:
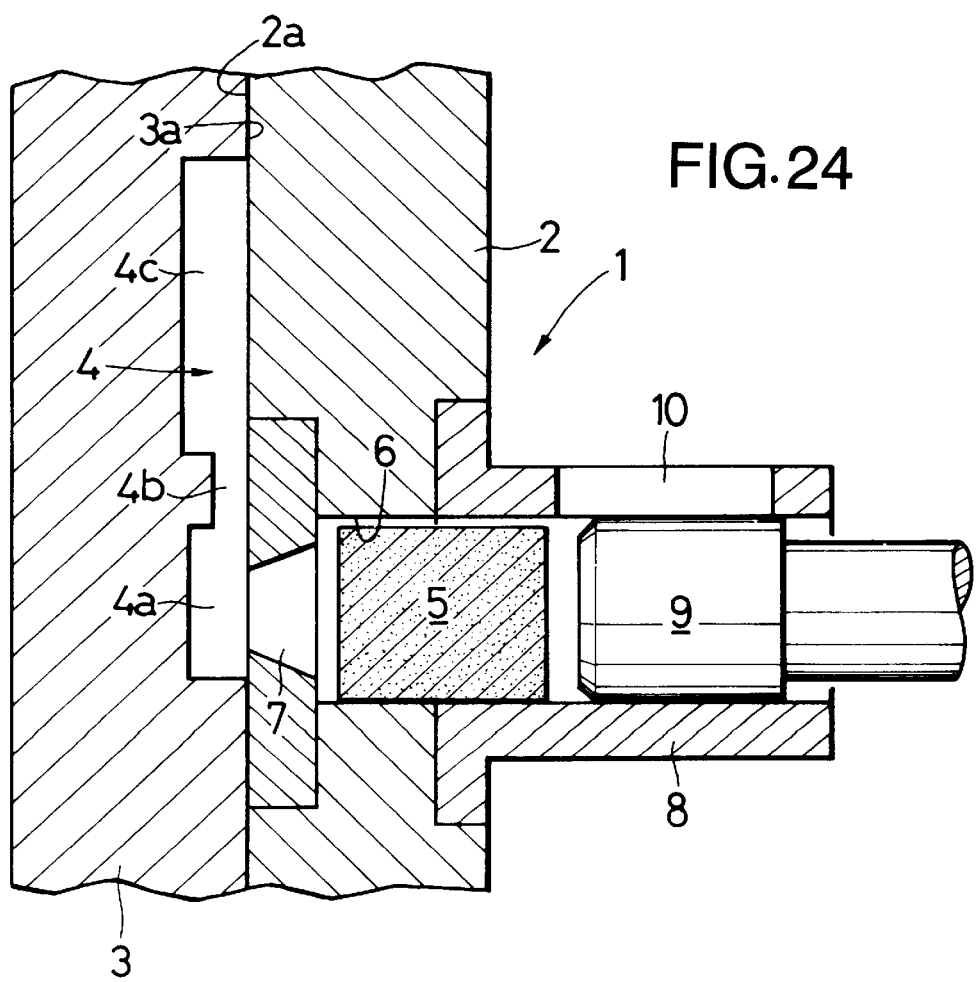
FIG. 24 is a vertical sectional view of a pressure casting device.

In the apparatus 1 shown in FIG. 24, a casting forming cavity 4 includes a medium-thickness portion forming zone 4a at a lower portion, a thinner-portion forming zone 4b at a middle portion, and a thick-portion forming zone 4c at an upper portion. The other construction is the same as in the pressure casting apparatus shown in FIG. 1. Therefore, portions or segments corresponding to those in the apparatus shown in FIG. 1 are designated by like reference characters, and the detailed description of them is omitted.

Table 8 shows compositions of examples $A_1$ to $A_3$ and comparative examples $a_1$ and $a_2$ of aluminum alloy materials. Each of these materials was cut off from a high quality long continuous casting produced in a continuous casting process. In producing the casting, a spheroidizing treatment of a primary crystal α-Al was performed. Each of the example $A_1$ and the like has a diameter of 76 mm and a length of 85 mm.

relationship, $\Delta Tb/\Delta Ta=0.55$, namely, $\Delta Tb/\Delta Ta \leq 0.68$, is established between temperature drop degrees $\Delta Ta$ and $\Delta Tb$.

Figure 26:
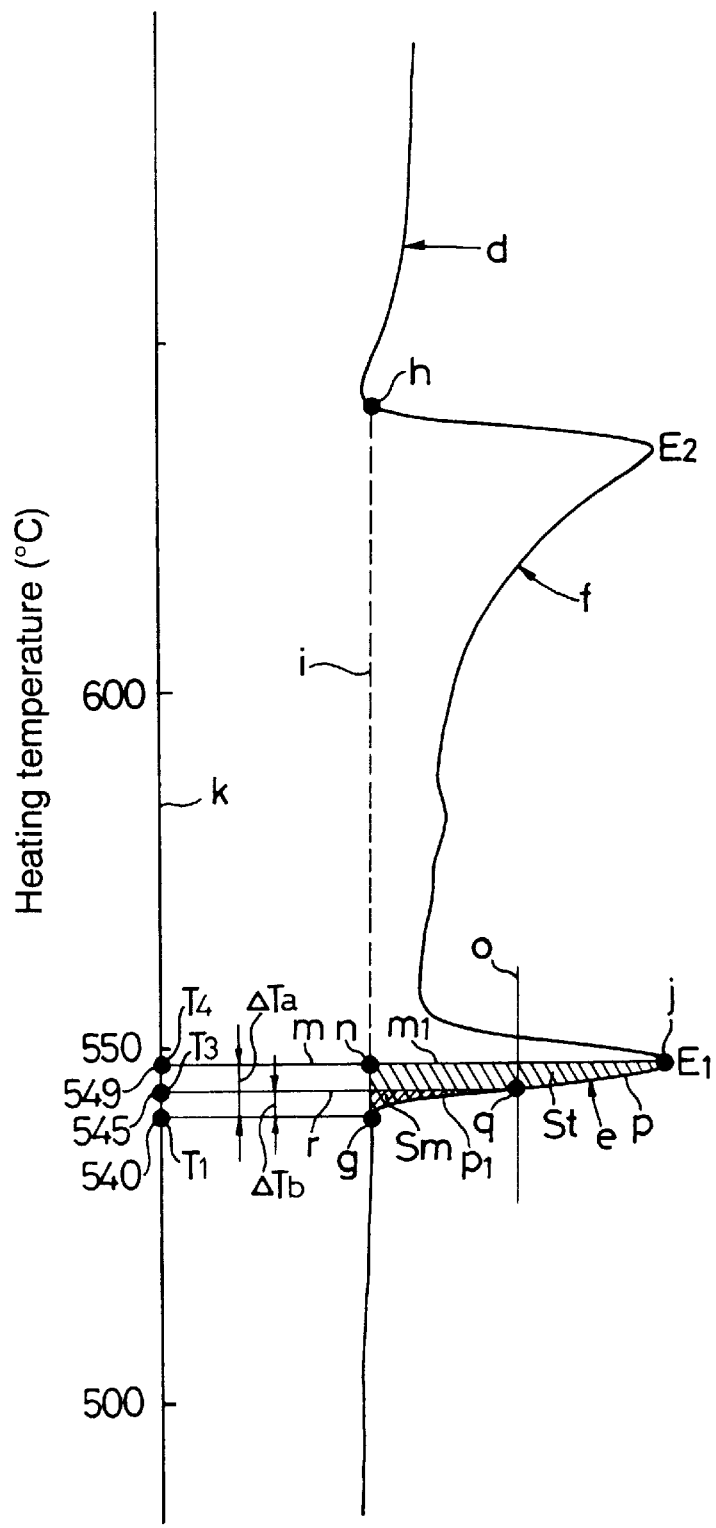
FIG. 26 is an enlarged diagram of an essential portion shown in FIG. 25.
Figure 27:
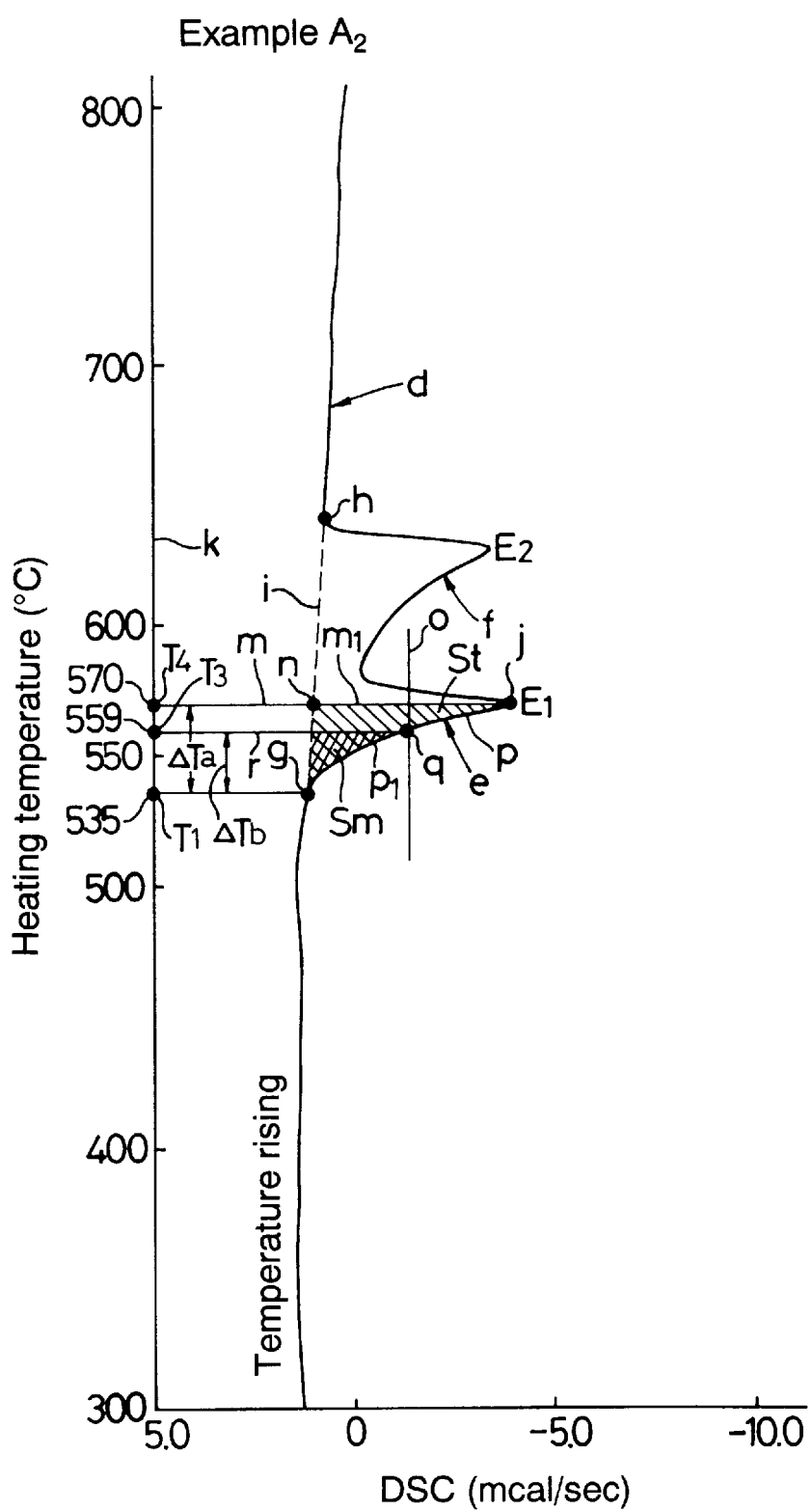
FIG. 27 is a differential thermal analysis thermograph for an example $A_2$.

The area of the following region FIG. 26 is represented by St: a region which is surrounded by (1) the basic line i which interconnects the rising start point g in the first angled endothermic section e and the dropping end point h in the second angled endothermic section f, (2) a first temperature straight line m corresponding to the above-described temperature straight line which interconnects the peak j of the first angled endothermic section e and the temperature graduation of the peak j on the axis k of heating temperature, and (3) the rising line segment p of the first angled endothermic section lying between the rising start point g and the peak j.

The dividing line o bisecting the segment $m_1$ of the temperature straight line m lying between the first intersection n of the first temperature straight line m with the basic line i and the peak i also intersects the rising line segment p. Thereupon, the area of the following region is represented by Sm: a region which is surrounded by (1) a second temperature straight line r which interconnects the second intersection q of the dividing line o with the rising line segment p and the temperature graduation of the second

TABLE 8

| Al alloy material | Chemical constituents (% by weight) | | | | | | | | |
|---|---|---|---|---|---|---|---|---|---|
| | Si | Cu | Mg | Fe | Zr | Mn | V | Ti | balance |
| Example $A_1$ | 0.17 | 10.3 | — | 0.18 | 0.18 | 0.27 | 0.1 | 0.05 | Al |
| Example $A_2$ | 5.3 | 2.9 | 0.3 | 0.12 | — | — | — | 0.01 | Al |
| Example $A_3$ | 2.1 | 9.8 | — | 0.15 | 0.15 | 0.3 | 0.12 | — | Al |
| Comparative example $a_1$ | 6.2 | 3.1 | 0.2 | 0.72 | — | — | — | 0.02 | Al |
| Comparative example $a_2$ | 2.6 | 2 | 4 | 0.13 | — | — | — | 0.03 | Al |

Figure 25:
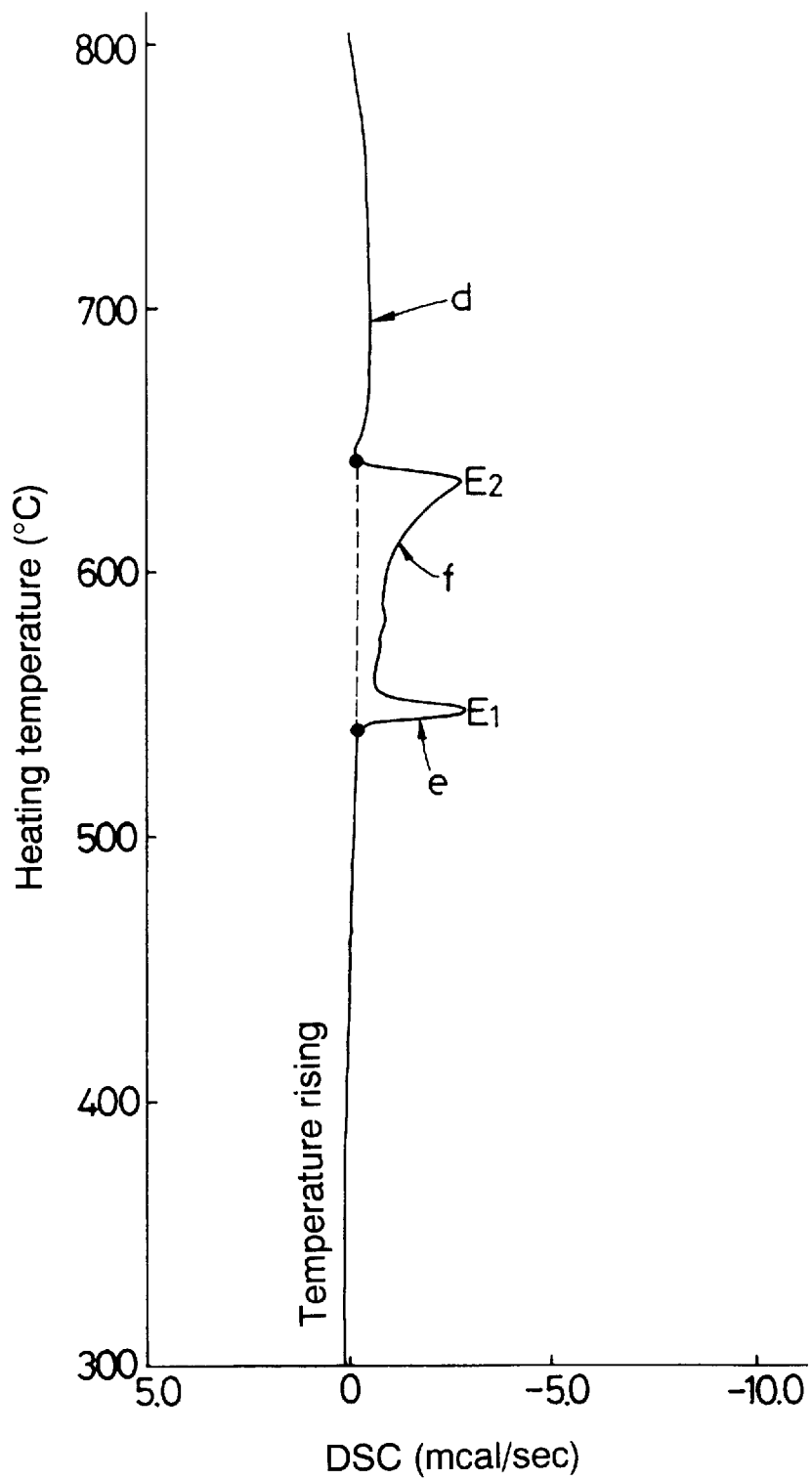
FIG. 25 is a differential thermal analysis thermograph for an example $A_1$.

The example $A_1$ was subjected to a differential scanning calorimetry (DSC) to provide results shown in FIGS. 25 and 26. In a differential thermal analysis thermograph d shown in each of FIGS. 25 and 26, a peak value $E_1$ of a first angled endothermic section e due to an eutectic melting is equal to 2.7 mcal/sec, and a peak value $E_2$ of a second angled endothermic section f due to a melting of a segment having a melting point higher than an eutectic point is equal to 2.6 mcal/sec. From this fact, it was confirmed that $E_1 > E_2$.

On the other hand, in the differential thermal analysis thermograph d of FIG. 26, a temperature straight line m interconnecting a peak j of the first angled endothermic section e and a temperature graduation of the peak j on an axis k of heating temperature intersects a basic line i which interconnects a rising start point g in the first angled endothermic section e and a dropping end point h in the second angled endothermic section f. A dividing line o bisecting a segment $m_1$ of the temperature straight line m lying between a first intersection n of the temperature straight line m with the basic line i and the peak j intersects a rising line segment p of the first angled endothermic section e lying between the rising start point g and the peak j. In this condition, the temperature $T_3$ at a second intersection q of the rising line segment p with the dividing line o is equal to 545° C.

Further, the temperature $T_1$ at the rising start point g is equal to 540° C., and the temperature $T_4$ at the peak j is equal to 549° C.

If $T_4-T_1=\Delta Ta$, $\Delta Ta$ is equal to 9° C., and if $T_3-T_1=\Delta Tb$, $\Delta Tb$ is equal to 5° C. Therefore, in the example $S_1$, a intersection q on the heating temperature axis k, (2) a portion P, of the rising line segment p lying between the rising start point g and the second intersection q, and (3) the basic line i.

In the example $A_1$, a relationship, Sm/St=0.138, namely, Sm/St$\leq$0.365, is established between the areas St and Sm. In measuring the areas St and Sm, a planimeter was used.

In order to establish the relationship, $\Delta Tb/\Delta Ta \leq 0.68$ and/or the relationship, Sm/St$\leq$0.365, it is necessary to decrease the amount of Mg and the like which are additional constituents having a low melting point rather than decreasing the amount of Cu, Si and the like which are eutectic constituents, thereby displacing the solid phase line toward the higher temperature side.

Then, the example $A_1$ was placed into the heating coil in the induction heating device and then heated under conditions of a frequency of 1 kHz and a maximum output power of 37 kW to prepare a semi-molten example $A_1$ having solid and liquid phases coexisting therein. In this case, the solid phase proportion was set in a range of 50% (inclusive) to 60% (inclusive).

Thereafter, the semi-molten example $A_1$ (indicated by character 5) was placed into the chamber 6 and passed through the gate 7 and charged into the cavity 4, while being pressurized under conditions of a moving velocity of the pressurizing plunger 9 of 0.07 m/sec and a mold temperature of 250° C. A pressurizing force is applied to the example $A_1$ fill in the cavity 4 by retaining the pressurizing plunger 9 at the terminate end of the stroke, and the example $A_1$ was solidified under the pressurization to provide an aluminum alloy casting 14.

Figure 28:
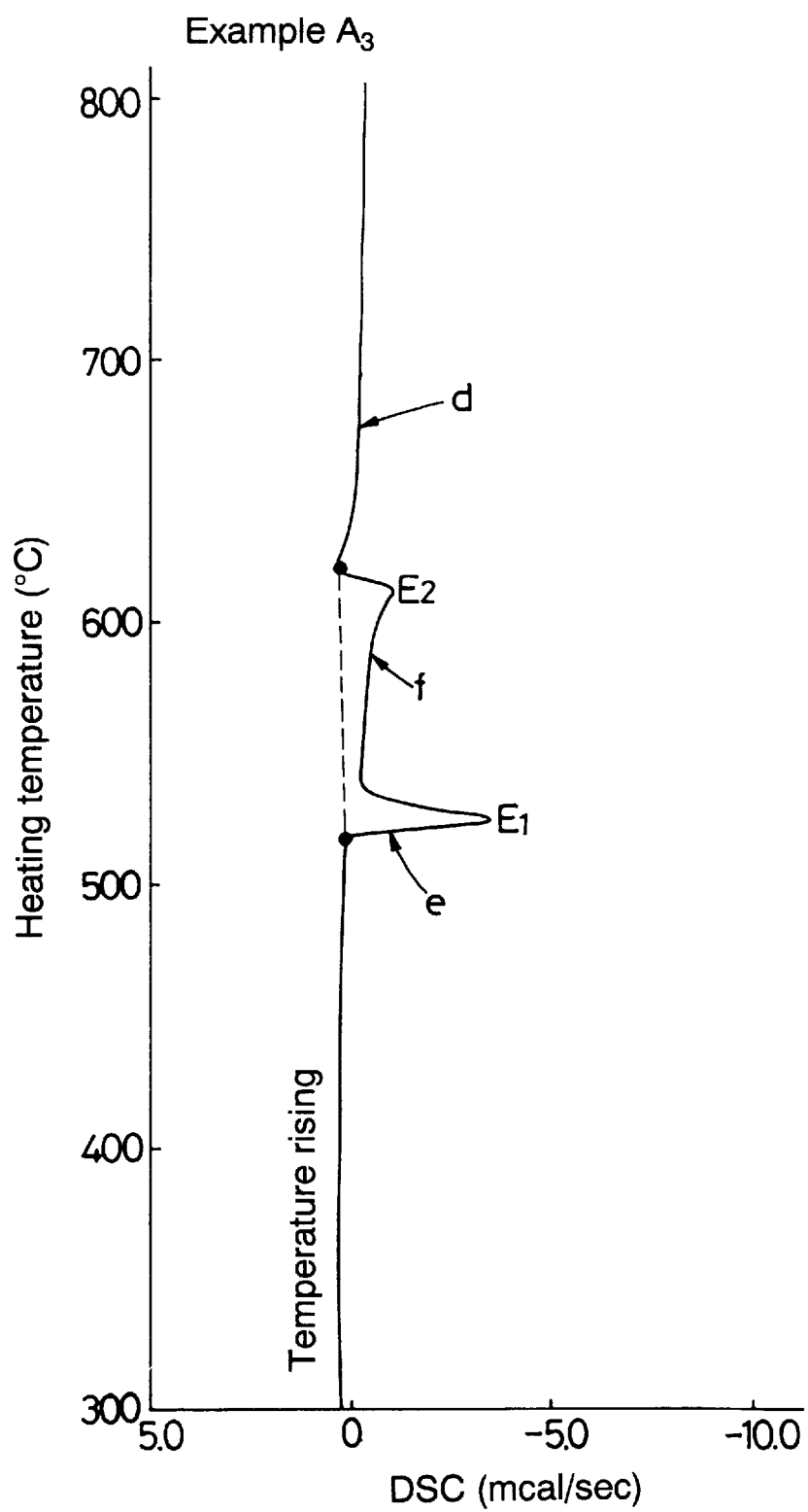
FIG. 28 is a differential thermal analysis thermograph for an example $A_3$.
Figure 29:
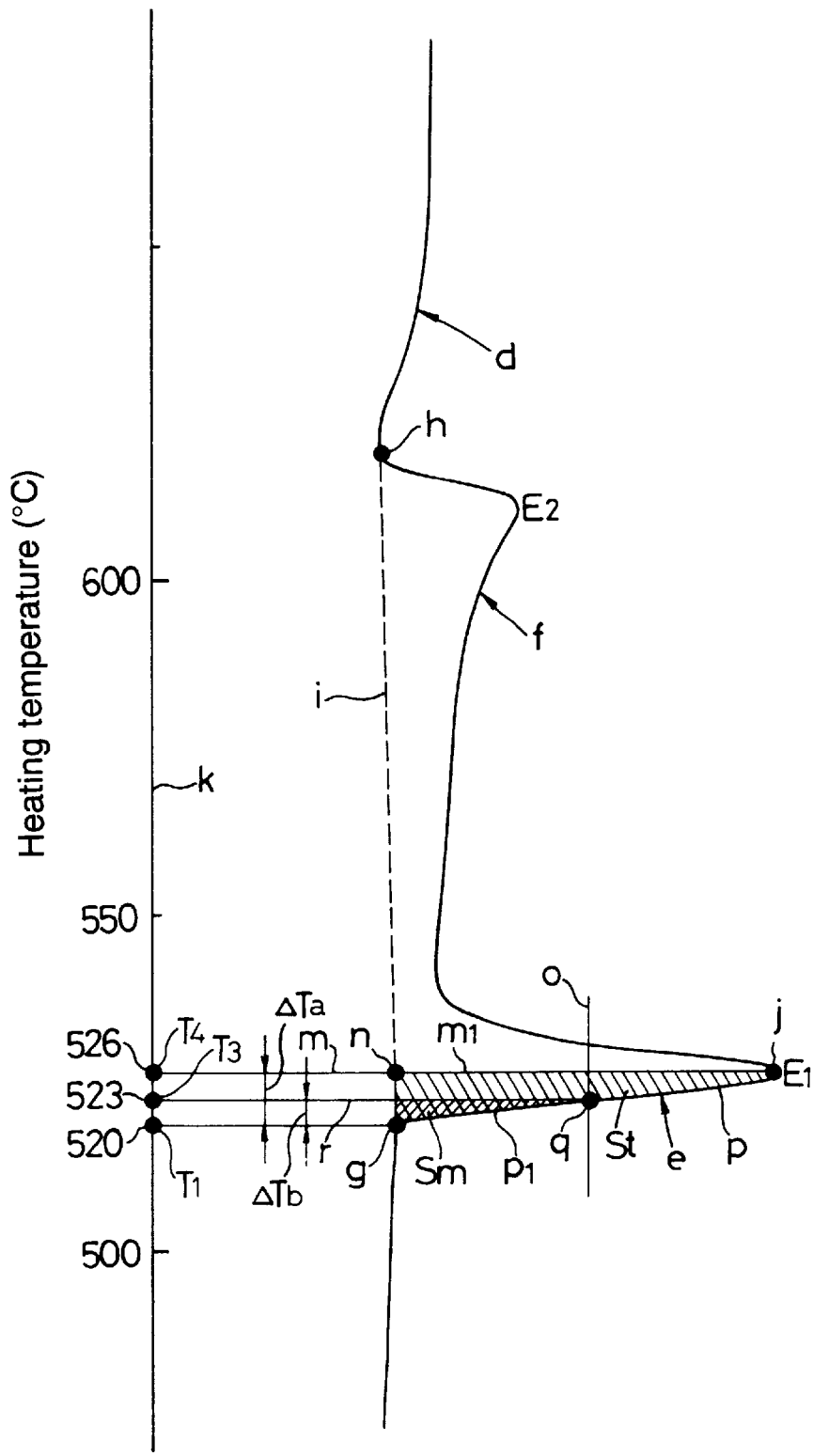
FIG. 29 is an enlarged diagram of an essential portion shown in FIG. 28.
Figure 30:
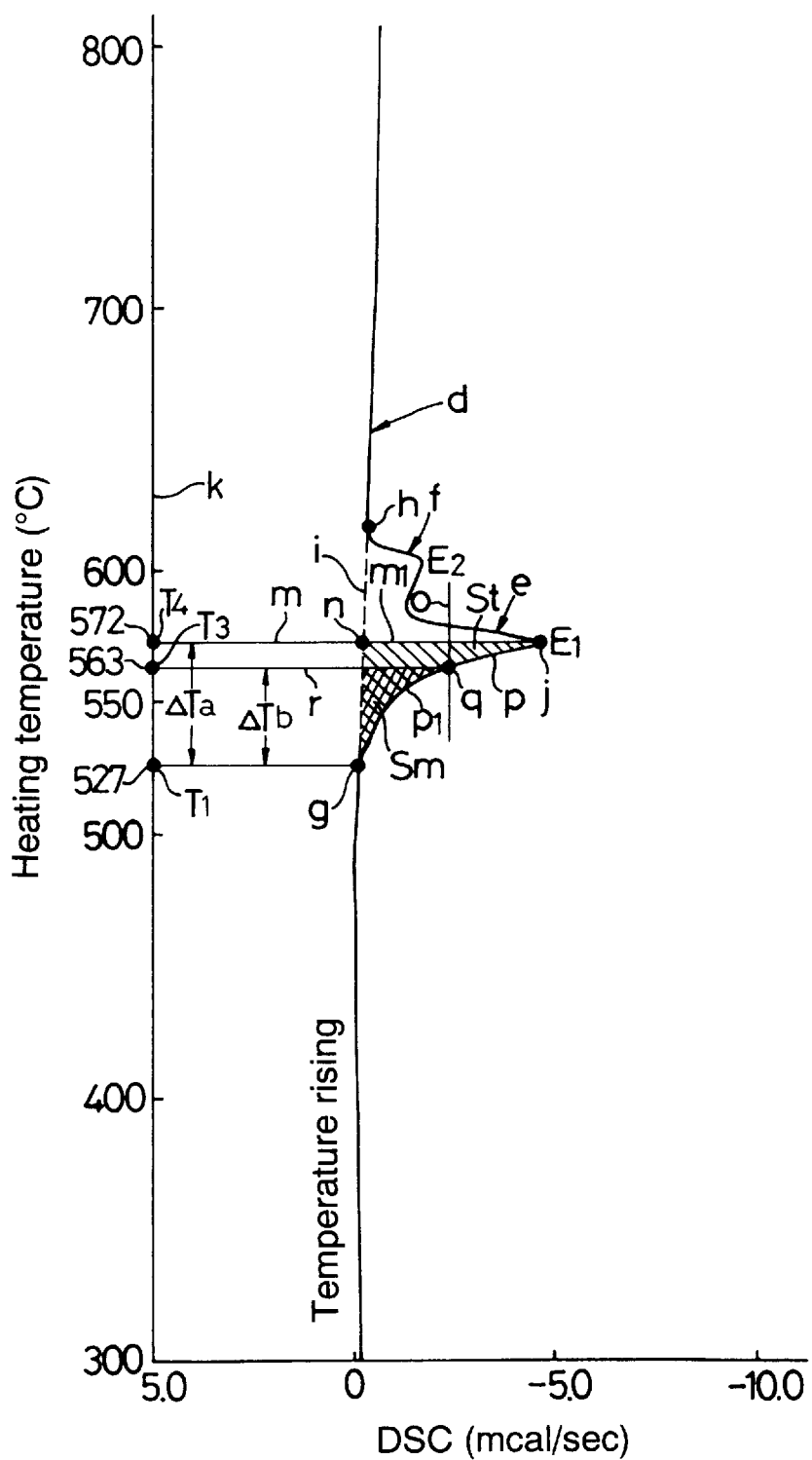
FIG. 30 is a differential thermal analysis thermograph for a comparative example $a_1$.
Figure 31:
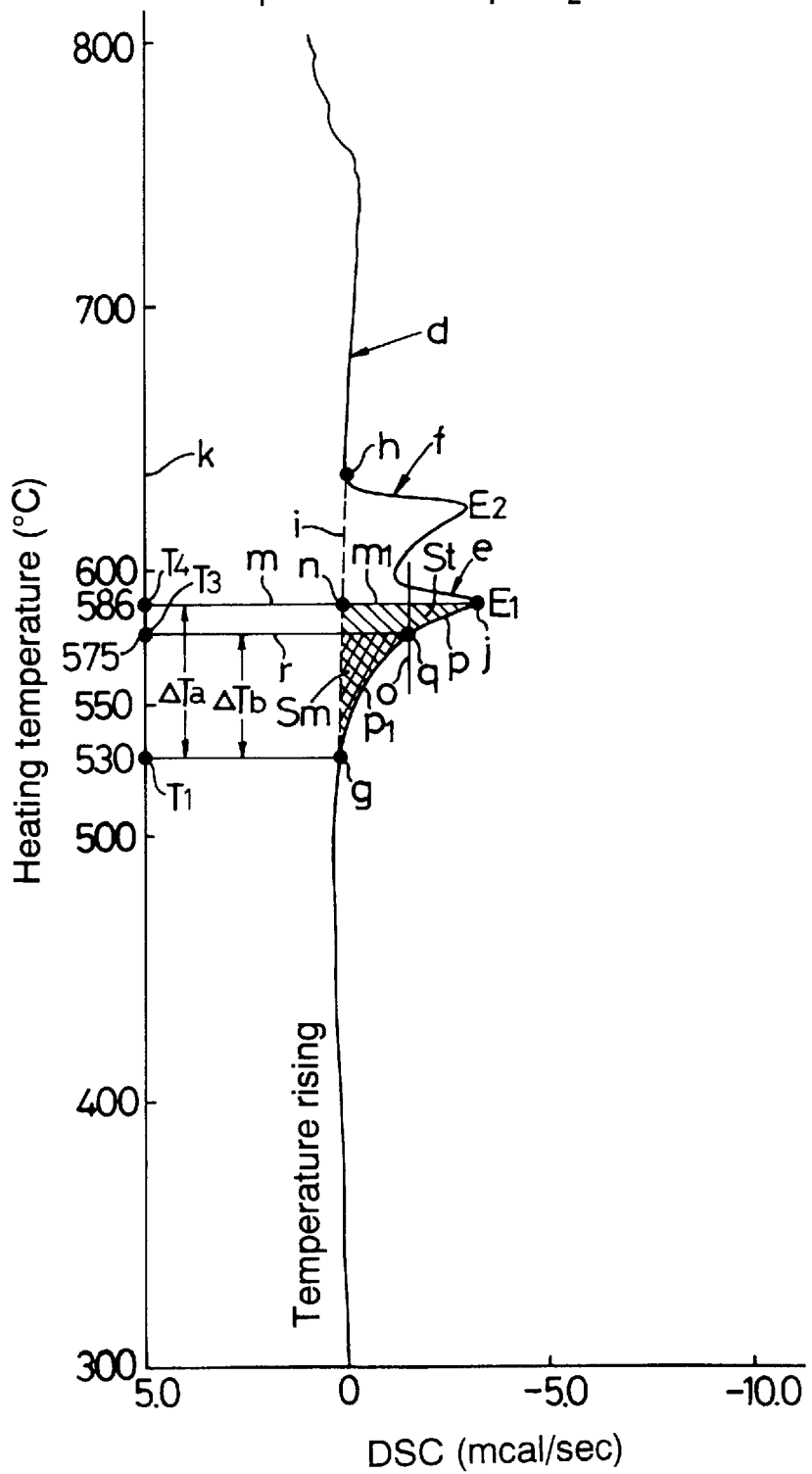
FIG. 31 is a differential thermal analysis thermograph for a comparative example $a_2$.

For the results of DSC shown in FIGS. 27 to 31, FIG. 27 corresponds to an example $A_2$, and FIGS. 28 and 29 correspond to an example $A_3$, while FIG. 30 corresponds to a comparative example $a_1$ and FIG. 31 corresponds to a comparative example $a_2$.

Using these examples $A_2$ and $A_3$ and comparative examples $a_1$ and $a_2$, four aluminum alloy castings were produced in the same casting process as those described above.

Table 9 shows the peak values $E_1$ and $E_2$, the ratio $E_1/E_2$, the temperature drop ranges $\Delta Ta$ and $\Delta Tb$, the ratio $\Delta Tb/\Delta Ta$, the ratio Sm/St of the areas St and Sm for the examples $A_1$ to $A_3$ and the comparative examples $a_1$ and $a_2$, and the presence or absence of defects in the produced aluminum alloy castings produced from the examples $A_1$ to $A_3$ and the comparative examples $a_1$ and $a_2$.

$\Delta Tb/\Delta Ta$ is set in the range of $\Delta Tb/\Delta Ta \leq 0.68$, the temperature range required for the gelled phase to be solidified is narrowed, and on the other hand, the temperature range required for the gelled phase to be produced from the liquid phase is widened. Thus, it is possible to improve the feedability of the liquid phase around the solid phase in the thicker portion 14c of the aluminum alloy casting 14 to prevent the generation of voids on the order of a micron.

Since the area St represents the released latent heat amount required for the liquid phase to be solidified, and the area Sm represents the released latent heat amount required for the gelled phase produced from the liquid phase to be solidified, if the ratio Sm/St is set in the range of $Sm/St \leq 0.365$, the released latent heat amount required for the gelled phase to be solidified is decreased and on the other hand, the released latent heat amount permitting the gelled phase to be produced from the liquid phase is increased. Thus, it is possible to improve the feedability of the liquid phase around the solid phase in the thicker portion 14c of the

TABLE 9

| Al alloy material | Peak value (mcal/sec) | | Temperature drop ranges (°C.) | | Ratio | Ratio | Presence or |
| --- | --- | --- | --- | --- | --- | --- | --- |
| | $E_1$ | $E_2$ | $\Delta Ta$ | $\Delta Tb$ | $\Delta Tb/\Delta Ta$ | Sm/St | absence of defects |
| Example $A_1$ | 2.7 | 2.6 | 9 | 5 | 0.55 | 0.138 | absence |
| Example $A_2$ | 4.9 | 4.2 | 35 | 24 | 0.68 | 0.364 | absence |
| Example $A_3$ | 3.7 | 1.3 | 6 | 3 | 0.50 | 0.365 | absence |
| Comparative example $a_1$ | 4.4 | 1.4 | 45 | 36 | 0.80 | 0.438 | presence |
| Comparative example $a_2$ | 3.2 | 2.9 | 56 | 45 | 0.80 | 0.709 | presence |

Figure 32:
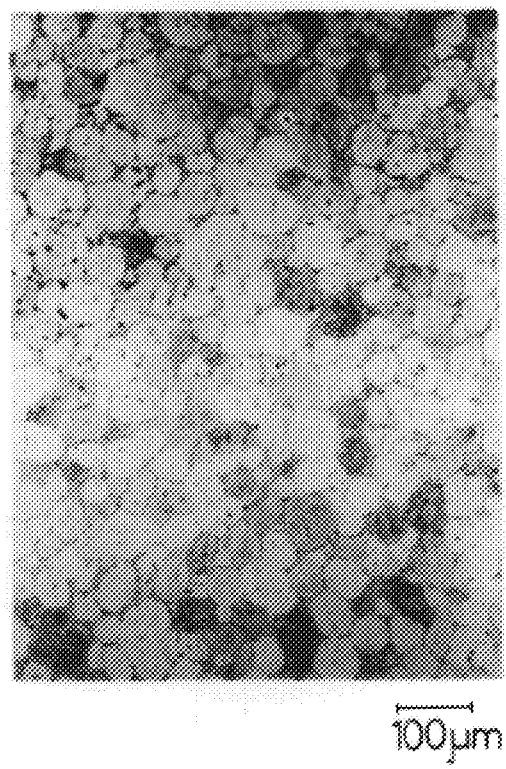
FIG. 32 is a photomicrograph showing the metallographic structure of an aluminum alloy casting produced using the example $A_1$.
Figure 33:
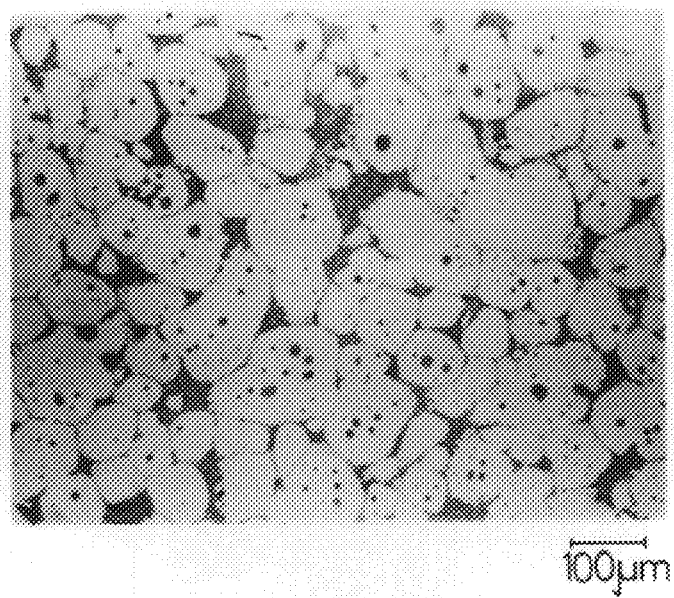
FIG. 33 is a photomicrograph showing the metallographic structure of an aluminum alloy casting produced using the example $A_2$.

FIGS. 32 to 34B are photomicrographs each showing the metallographic structure of the thicker portion 14c of the aluminum alloy casting 14. FIG. 32 corresponds to the case where the example $A_1$ is used; FIG. 33 corresponds to the case where the example $A_2$ is used; and FIGS. 34A and 34B correspond to the case where the comparative example $a_1$ is used.

As can be seen from FIGS. 32 and 33, in the case of the aluminum alloy castings produced using the examples $A_1$ and $A_2$, there is no defect such as voids on the order of a micron generated in the thicker portion 14c of the aluminum alloy casting 14, because the relationship $E_1 > E_2$ is established between the peak values $E_1$ and $E_2$, and the relationship $\Delta Tb/\Delta Ta \leq 0.68$ is established between the temperature drop ranges $\Delta Tb$ and $\Delta Ta$. In these cases, the relationship, $Sm/St \leq 0.365$ is also established between the areas St and Sm.

If the latent heat of the liquid phase is decreased to ½ of the maximum released latent heat, namely, to $E_1/2$ in the course of the solidification of the semi-molten alloy material, the liquid phase is thereafter gelled, so that the viscosity is gradually increased. This causes a particularly degraded feedability of the liquid phase around the solid phase in the thicker portion 14c of the aluminum alloy casting and hence, voids on the order of a micron are liable to be generated in the thicker portion 14c. This tendency is doubled, because the thinner portion forming zone 4b is located short of the thicker portion forming zone 4c, as shown in FIG. 24.

Since $\Delta Ta$ represents the temperature drop range required for the liquid phase to be solidified, and $\Delta Tb$ represents the temperature drop range required for the gelled phase produced from the liquid phase to be solidified, if the ratio aluminum alloy casting 14 to prevent the generation of voids on the order of a micron.

Figure 34A:
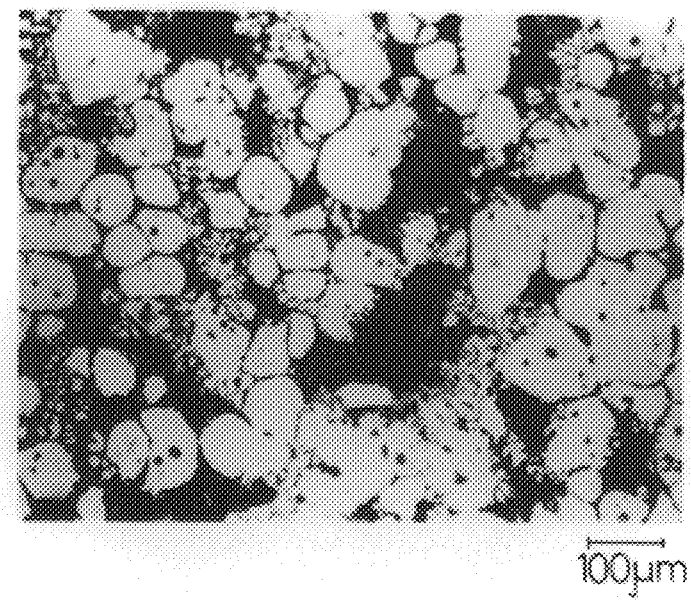
FIG. 34A is a photomicrograph showing the metallographic structure of an aluminum alloy casting produced using the comparative example $a_1$.
Figure 34B:
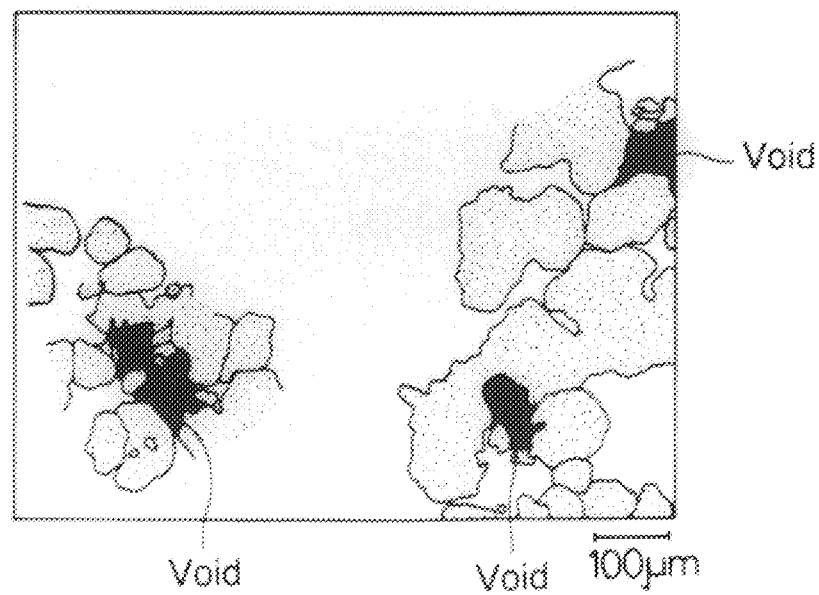
FIG. 34B is an essential portion of the photomicrograph shown in FIG. 34A.

In the case of the aluminum alloy casting 14 produced using the comparative example $a_1$ shown in FIGS. 34A and 34B, the relationship $E_1 > E_2$ is established, but the relationship $\Delta Tb/\Delta Ta \leq 0.68$ and/or the relationship $Sm/St \leq 0.365$ are not established and hence, the thicker portion 14c has voids on the order of a micron generated therein.

In any of the aluminum alloy castings, the thinner portion 14b has no defects generated therein.

Figure 35:
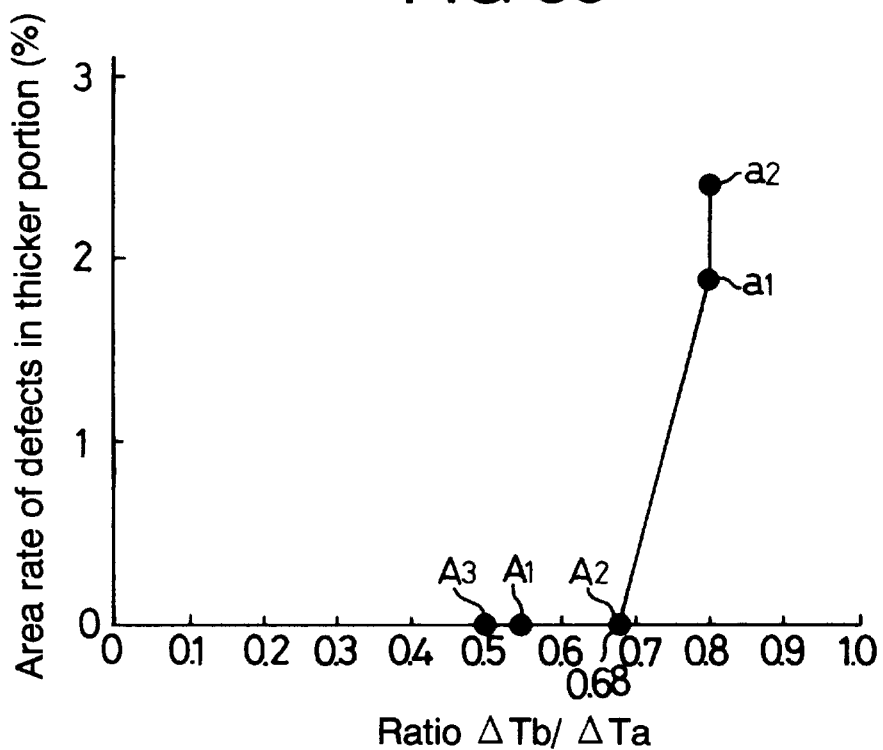
FIG. 35 is a graph illustrating the relationship between the ratio $\Delta Tb/\Delta Ta$ and the area proportion of defects in a thicker portion.

FIG. 35 shows the relationship between the ratio $\Delta Tb/\Delta Ta$ and the defect area proportion in the thicker portion 14c. It can be seen from FIG. 35 that defects are generated when $\Delta Tb/\Delta Ta > 0.68$.

Figure 36:
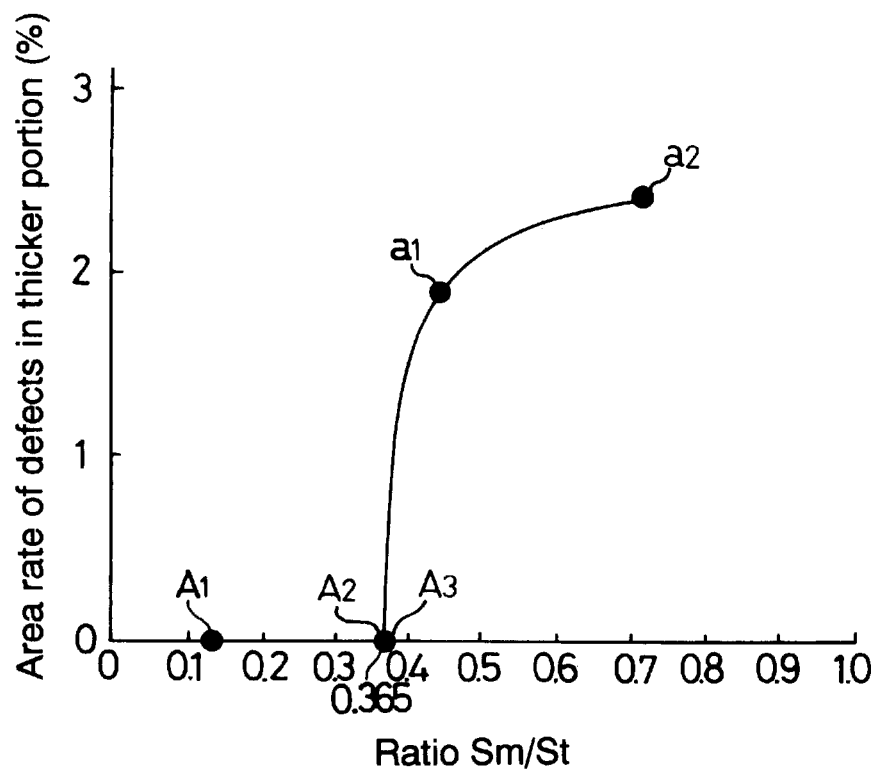
FIG. 36 is a graph illustrating the relationship between the ratio Sm/St and the area proportion of defects in a thicker portion.

FIG. 36 shows the relationship between the ratio Sm/St and the defect area proportion in the thicker portion 14c. It can be seen from FIG. 36 that defects are generated when $Sm/St > 0.365$.

The defect area proportion in the thicker portion was measured using an image resolving device.

Embodiment IV

Table 10 shows compositions of examples $A_1$ to $A_7$ and comparative examples $a_1$ and $a_2$. The example $A_1$ is an Al-Si-CU based alloy; the examples $A_2$ to $A_4$ are Al-Si-Mg based alloys; the examples $A_5$ to $A_7$ and the comparative example $a_1$ are Al-Cu based alloys; and the comparative example $a_2$ is an Al-Zn-Mg based alloy. Each of the examples and comparative examples was cut off from a high quality long continuous casting produced in a continuous casting process. In producing the casting, a spheroidizing treatment of a primary crystal α-Al was performed. Each of the examples and the comparative examples has a diameter of 50 mm and a length of 65 mm.

TABLE 10

| Al alloy material | Chemical constituents (% by weight) | | | | | | | | | |
|---|---|---|---|---|---|---|---|---|---|---|
| | Si | Cu | Mg | Fe | Zr | Zn | Mn | V | Ti | balance |
| Example $A_1$ | 6.8 | 3.9 | 0.1 | 0.1 | — | 0.1 | 0.2 | — | 0.15 | Al |
| Example $A_2$ | 7 | <0.2 | 0.35 | <0.2 | — | <0.1 | <0.1 | — | <0.2 | Al |
| Example $A_3$ | 7 | <0.2 | 0.55 | <0.2 | — | <0.1 | <0.1 | — | 0.12 | Al |
| Example $A_4$ | 5 | 3 | 0.32 | <0.2 | — | <0.2 | <0.1 | — | 0.13 | Al |
| Example $A_5$ | 0.15 | 12.2 | — | 0.18 | 0.15 | — | 0.3 | 0.1 | 0.05 | Al |
| Example $A_6$ | 0.18 | 8.2 | — | 0.18 | 0.2 | — | 0.25 | 0.1 | 0.05 | Al |
| Example $A_7$ | 0.17 | 10.3 | — | 0.18 | 0.18 | — | 0.27 | 0.1 | 0.05 | Al |
| Comparative example $a_1$ | 0.11 | 1.9 | 1.4 | 1.3 | — | — | 1.3 | — | 0.1 | Al |
| Comparative example $a_2$ | 0.4 | <0.1 | 7.8 | <0.3 | — | 28.8 | 0.3 | — | 0.2 | Al |

Figure 37:
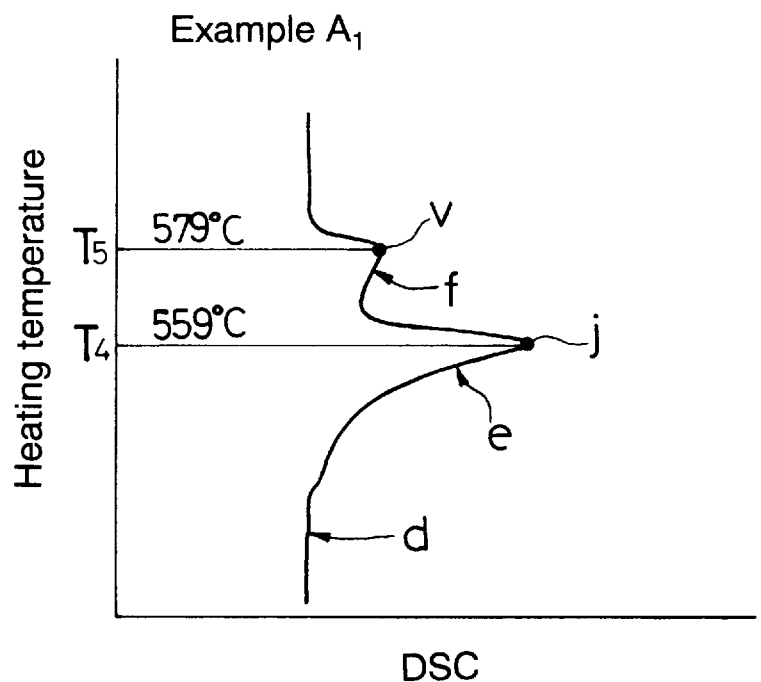
FIG. 37 illustrates an essential portion of a differential thermal analysis thermograph for an example $A_i$.
Figure 38:
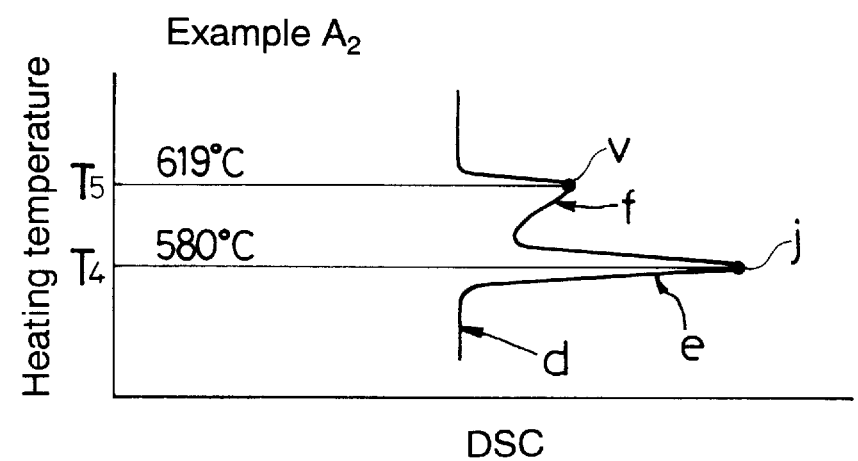
FIG. 38 illustrates an essential portion of a differential thermal analysis thermograph for an example $A_2$.
Figure 39:
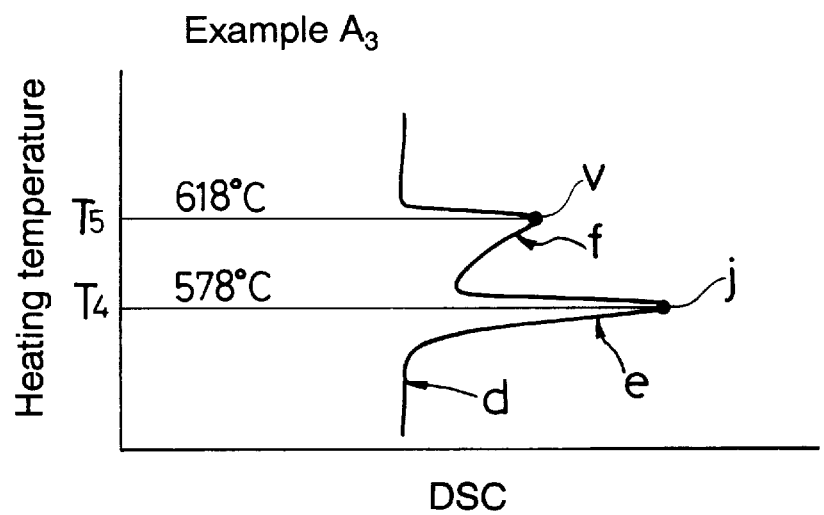
FIG. 39 illustrates an essential portion of a differential thermal analysis thermograph for an example $A_3$.
Figure 40:
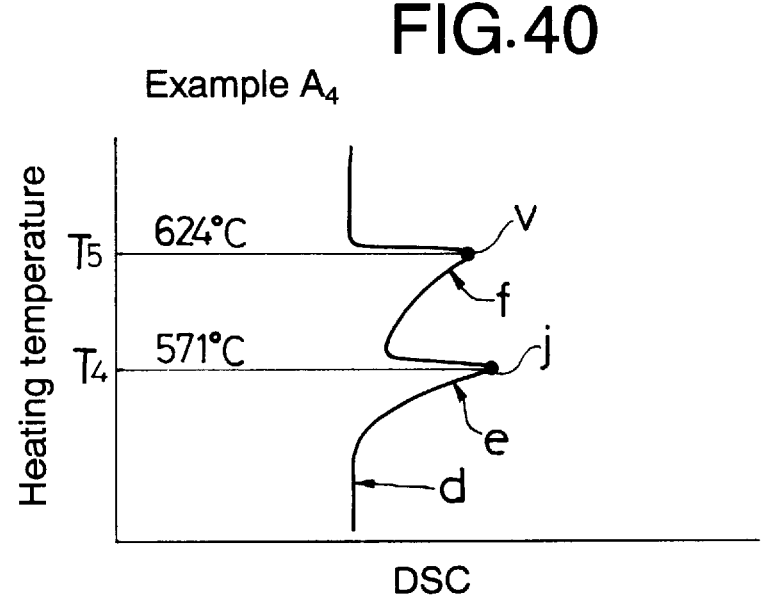
FIG. 40 illustrates an essential portion of a differential thermal analysis thermograph for an example $A_4$.
Figure 41:
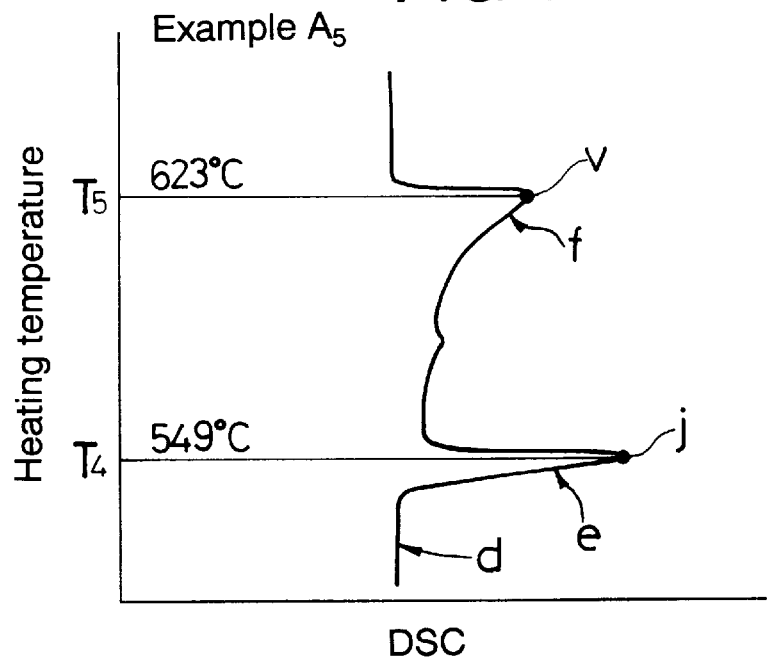
FIG. 41 illustrates an essential portion of a differential thermal analysis thermograph for an example $A_5$.
Figure 42:
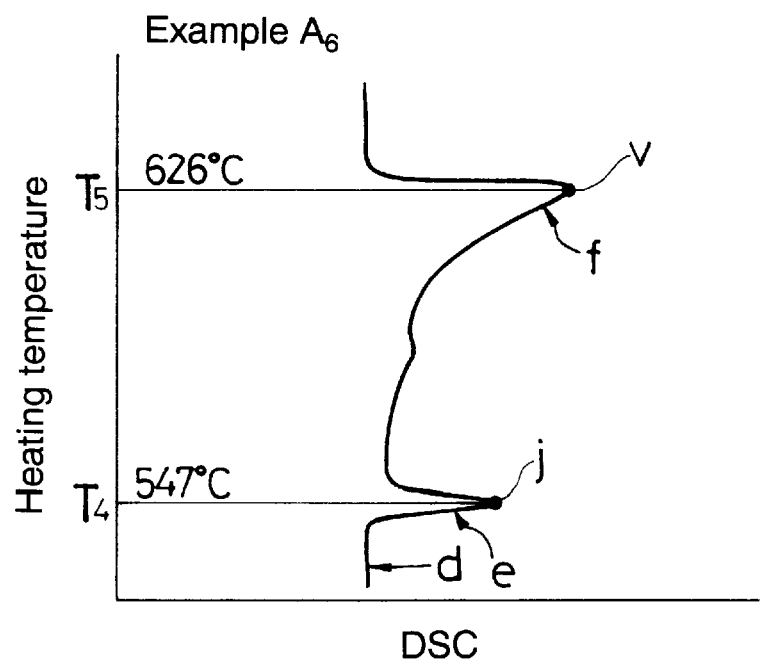
FIG. 42 illustrates an essential portion of a differential thermal analysis thermograph for an example $A_6$.
Figure 43:
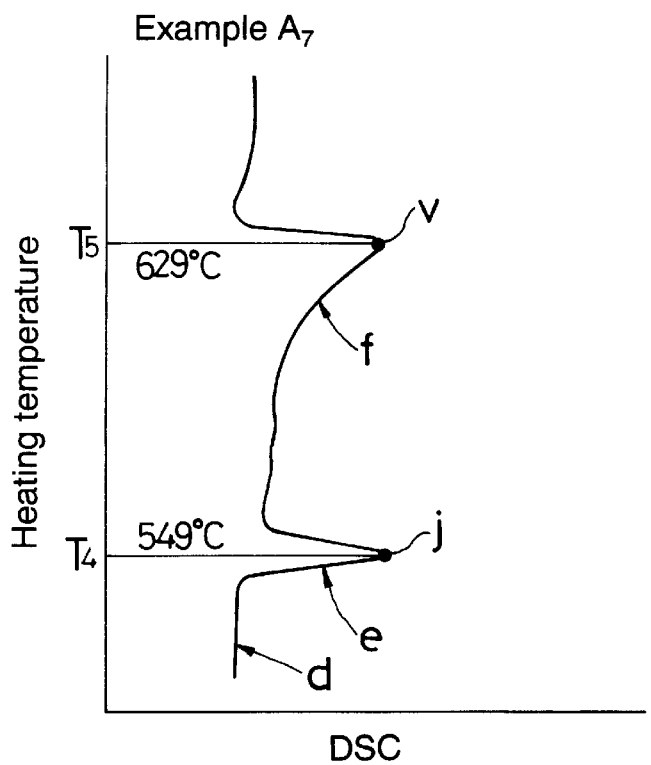
FIG. 43 illustrates an essential portion of a differential thermal analysis thermograph for an example $A_7$.
Figure 44:
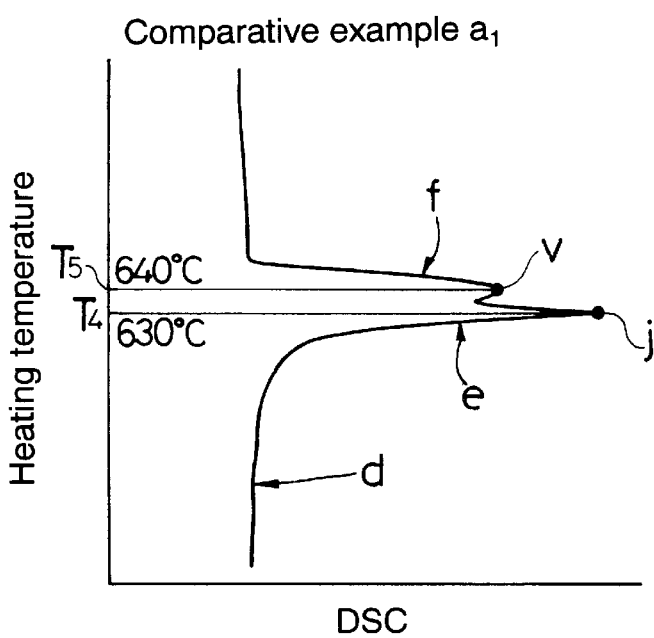
FIG. 44 illustrates an essential portion of a differential thermal analysis thermograph for a comparative example $a_1$.
Figure 45:
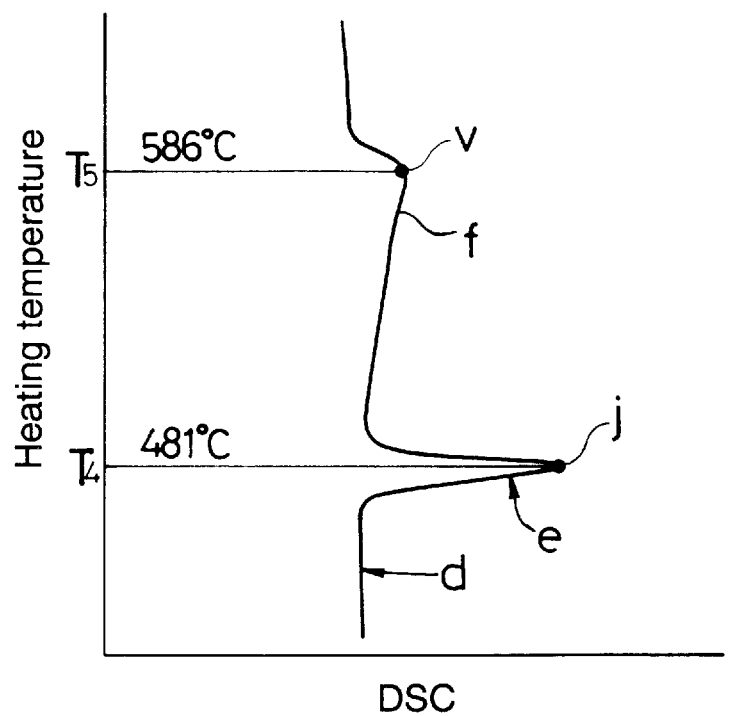
FIG. 45 illustrates an essential portion of a differential thermal analysis thermograph for a comparative example $a_2$.

The example $A_1$ was subjected to a differential scanning calorimetry (DSC) to provide the result shown in FIG. 37. In the differential thermal analysis thermograph d shown in FIG. 37, there are a first angled endothermic section e due to an eutectic melting, and a second angled endothermic section f due to a melting of a segment having a melting point higher than an eutectic point. In this case, the temperature $T_4$ at a peak j of the first angled endothermic section e is equal to 559° C., and the temperature at a peak of the second angled endothermic section f is equal to 579° C. Therefore, it is found that the difference $T_5-T_4$ between the temperatures $T_4$ and $T_5$ is equal to 20° C.

Then, the example $A_1$ was placed into a heating coil in an induction heating device and then heated under conditions of a frequency of 1 kHz, a maximum output power of 30 kW and a heating time of 7 minutes to prepare a semi-molten example $A_1$ having solid and liquid phases coexisting therein. In this case, the solid phase proportion was set in a range of 40% (inclusive) to 60% (inclusive).

Thereafter, the semi-molten example $A_1$ (indicated by character 5) was placed into the chamber 6 and passed through the gate 7 and charged into the cavity 4, while being pressurized under conditions of a moving velocity of the pressurizing plunger 9 of 0.2 m/sec and a mold temperature of 250° C. A pressurizing force is applied to the example $A_1$ fill in the cavity 4 by retaining the pressurizing plunger 9 at the terminate end of the stroke, and the example $A_1$ was solidified under the pressurization to provide an aluminum alloy casting $A_1$.

Each of the examples $A_2$ to $A_7$ and the comparative examples $a_1$ and $a_2$ was also subjected to DSC. Further, eight aluminum alloy castings $A_2$ to $A_7$, $a_1$ and $a_2$ were produced in the same casting process using the examples $A_2$ to $A_7$ and the comparative examples $a_1$ and $a_2$. In this case, the heating time was 7 minutes as described above. For comparison, an aluminum alloy casting $a_3$ was produced for a heating time set at 20 minutes in an electric resistance furnace.

Then, each of the aluminum alloy castings $A_1$ to $A_7$ and $a_1$ to $a_3$ was subjected to a T6 treatment under conditions shown in Table 11.

TABLE 11

| | T6 treatment | | | | |
|---|---|---|---|---|---|
| | Solution treatment | | | Aging treatment | |
| Al alloy casting | Temperature (°C.) | Time (hr) | Cooling type | Temperature (°C.) | Time (hr) |
| $A_1$ | 500 | 5 | water cooling | 160 | 5 |
| $A_2$ | 540 | | | 170 | |
| $A_3$ | | | | | |
| $A_4$ | 515 | | | | 10 |
| $A_5$ | 525 | | | 190 | 18 |
| $A_6$ | | | | | |
| $A_7$ | | | | | |
| $a_1$ | 525 | 8 | water cooling | 160 | 9 |
| $a_2$ | | | | | |
| $a_3$ | 465 | | | 125 | 28 |

For the purpose of carrying out a fatigue test, eight test pieces each including a parallel portion having a diameter of 4 mm and a length 20 mm were fabricated from each of the aluminum alloy castings $A_1$ to $A_7$ and $a_1$ to $a_3$ resulting from the T6 treatment. Each of the test pieces was subjected to a test with different stress amplitudes at room temperature using an electric hydraulic fatigue tester to determine the number of repetitions up to the fracture. From this data, the fatigue strength $S_1$ at $10^7$ repetitions was determined. Table 7 shows the results.

FIGS. 38 to 43, 44 and 45 show differential thermal analysis thermographs for the examples $A_2$ to $A_7$ and the comparative examples $a_1$ and $a_2$.

Table 12 shows the temperatures at the peaks j of the first and second angled endothermic sections e and f, the difference $T_5-T_4$ between the temperatures $T_4$ and $T_5$, the heating time and the casting temperature for the examples $A_1$ to $A_7$ and the comparative examples $a_1$ and $a_2$, as well as the presence or absence of voids, the presence or absence of the coalescence of the primary crystal α-Al and the fatigue strength $S_1$ for the aluminum alloy castings $A_1$ to $A_7$ and $a_1$ to $a_3$.

TABLE 12

| Al alloy material | Temperature at peaks T$_4$ (°C.) | T$_5$ (°C.) | Difference T$_5$–T$_4$ ( ) | Heating time (minute) | Casting temperature (°C.) | Presence or absence of voids | Presence or absence of coalescence of primary crystal α-Al | Fatigue strength S$_1$ (MPa) |
|---|---|---|---|---|---|---|---|---|
| A$_1$ | 559 | 579 | 20 | 7 | 572 | absence | absence | 120 |
| A$_2$ | 580 | 619 | 39 | | 590 | | | 120 |
| A$_3$ | 578 | 618 | 40 | | 588 | | | 120 |
| A$_4$ | 571 | 624 | 53 | | 594 | | | 140 |
| A$_5$ | 549 | 623 | 74 | | 595 | | | 130 |
| A$_6$ | 547 | 626 | 79 | | 612 | | | 130 |
| A$_7$ | 549 | 629 | 80 | | 605 | | | 130 |
| a$_1$ | 630 | 640 | 10 | 7 | 586 | presence | absence | 80 |
| a$_3$ | 630 | 640 | 10 | 20 | 586 | absence | presence | 90 |
| a$_2$ | 481 | 586 | 105 | 7 | 573 | presence | absence | 60 |

Figure 46:
FIG. 46 is a photomicrograph showing the metallographic structure of an aluminum alloy casting $A_7$.
Figure 47A:
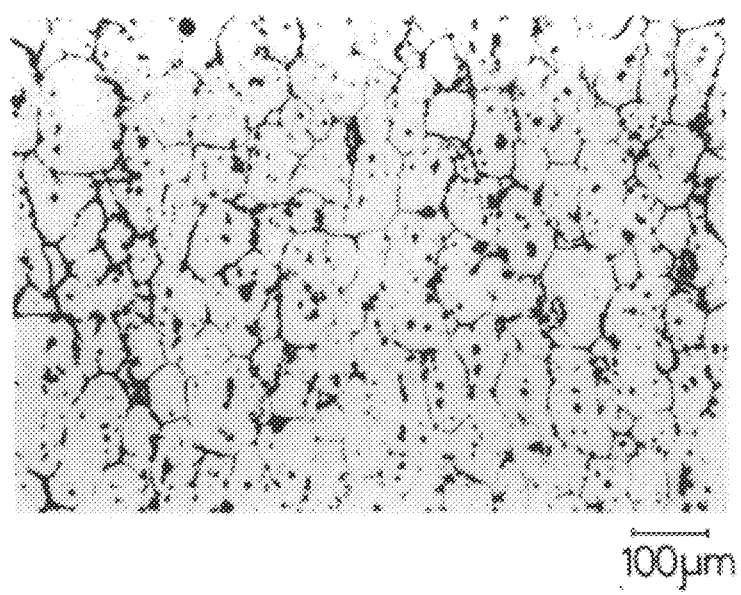
FIG. 47A is a photomicrograph showing the metallographic structure of an aluminum alloy casting $a_1$.
Figure 48:
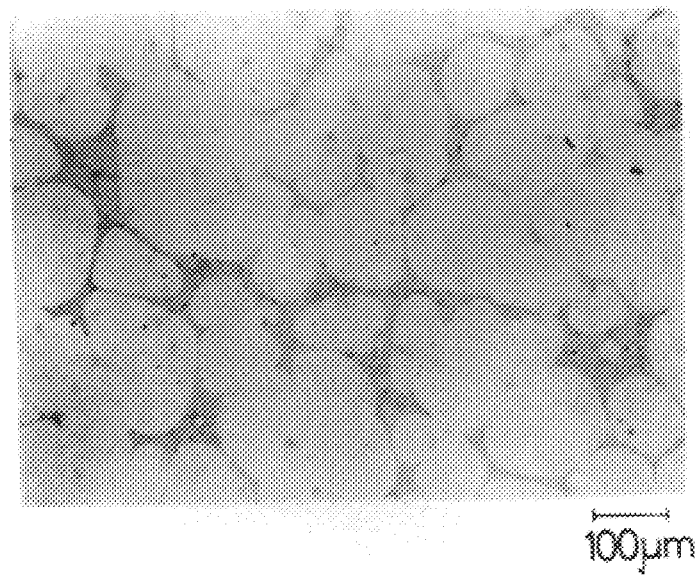
FIG. 48 is a photomicrograph showing the metallographic structure of an aluminum alloy casting $a_3$.
Figure 49:
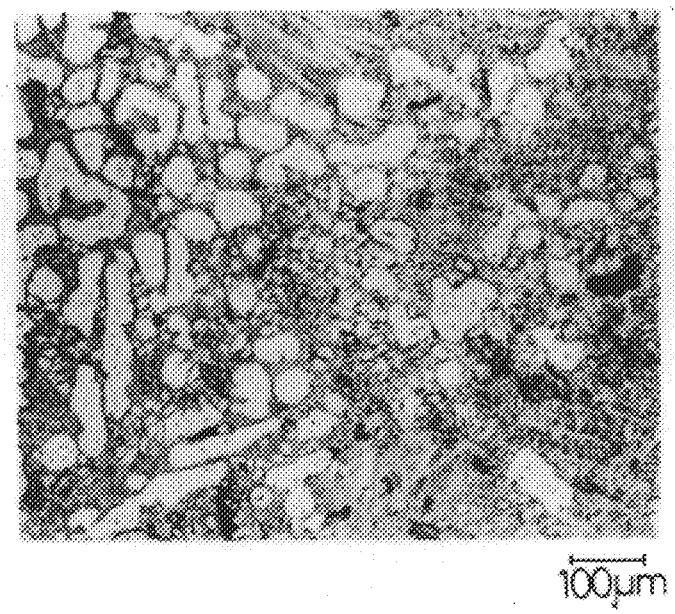
FIG. 49 is a photomicrograph showing the metallographic structure of an aluminum alloy casting $a_2$.

FIG. 46 is a photomicrograph showing the metallographic structure of the aluminum alloy casting A$_7$. FIGS. 47A, 48 and 49 are photomicrographs showing the metallographic structures of the aluminum alloy castings a$_1$, a$_3$ and a$_2$, respectively.

As can be seen from FIGS. 37 to 43 and 46 and Table 12, the aluminum alloy castings A$_1$ to A$_7$ were produced from the examples A$_1$ to A$_7$ with the difference T$_5$–T$_4$ between the temperatures set in a range of 20° C.$\leq$T$_5$–T$_4$$\leq$80° C., and the variation in solid phase proportion relative to the variation in heating temperature was blunted. Thus, it is possible to increase the temperature rising rate and heat the examples A$_1$ to A$_7$ to the casting temperature within a short time of 7 minutes, thereby preventing the coalescence of the primary crystal α-Al.

In addition, the diffusion of the primary crystal α-Al is actively effected as a result of widening of the temperature range permitting the solid and liquid phases to coexist, and therefore, the fine spheroidization and the uniform dispersion of the primary crystal α-Al are promoted, and the generation of shrinkage cavities is also avoided.

From this fact, each of the aluminum alloy castings A$_1$ to A$_7$ has a sound casting quality and an excellent fatigue strength.

Figure 47B:
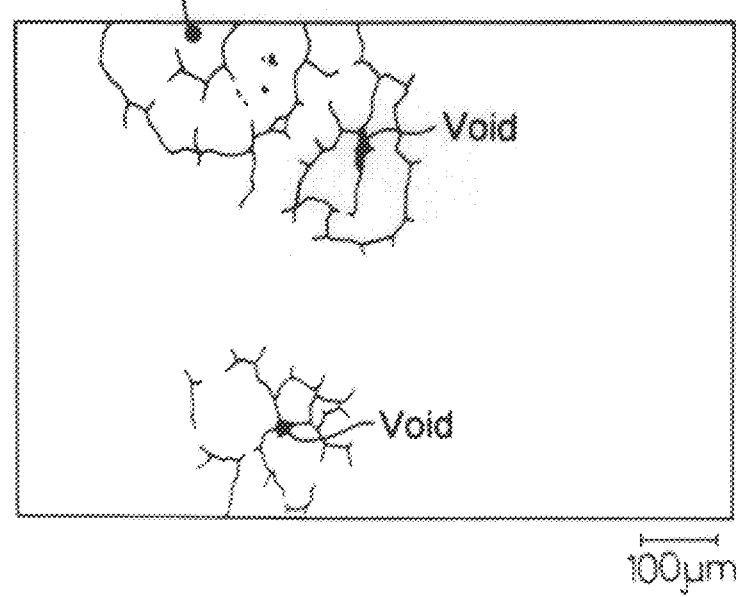
FIG. 47B illustrates an essential portion of the photomicrograph shown in FIG. 47A.

In the case of the aluminum alloy casting a$_1$ shown in FIGS. 47A and 47B, voids were generated due to the inclusion of air occurring during pouring of the material, because the difference T$_5$–T$_4$ between the temperatures in the comparative example a$_1$ was lower than 20° C., and the heating time was as short as 7 minutes.

In the case of the aluminum alloy casting a$_3$ shown in FIG. 48, the primary crystal α-Al (massive portion) was coalesced, because the heating time for the comparative example a$_3$ was as long as 20 minutes.

In the case of the aluminum alloy casting a$_2$ shown in FIG. 49, shrinkage cavities and thus, voids (black portions), were generated during solidification, because the difference T$_5$–T$_4$ between the temperatures in the comparative example a$_3$ was higher than 80° C.

For comparison, using the examples A$_1$ to A$_7$ and the comparative examples a$_1$ and a$_2$, aluminum alloy extrusions A$_1$ to A$_7$, a$_1$ and a$_2$ were produced by an extruding process under conditions of an extruding temperature of 350° to 420° C., a container temperature of 300° C., a die temperature of 250° C., a die bore diameter of 35 mm and an extrusion ratio of 4.7.

Each of the aluminum alloy extrusions A$_1$ to A$_7$, a$_1$ and a$_2$ was subjected to a T6 treatment under the same conditions as for the aluminum alloy castings A$_1$ to A$_7$, a$_1$ and a$_2$ (see Table 11). Then, test pieces similar to those described above were fabricated from the aluminum alloy extrusions A$_1$ to A$_7$, a$_1$ and a$_2$ and subjected to a fatigue test similar to that described above to determine the fatigue strength S$_2$ at 10$^7$ repetitions.

Table 13 shows the strength ratio S$_1$/S$_2$ of the fatigue strength S$_1$ of each of the aluminum alloy castings A$_1$ to A$_7$, a$_1$, a$_3$ and a$_2$ to the fatigue strength S$_2$ of each of the aluminum alloy extrusions A$_1$ to A$_7$, a$_1$, a$_3$ and a$_2$. In Table 13, the aluminum alloy extrusion a$_3$ is the same as the aluminum alloy extrusion a$_1$.

TABLE 13

| Al alloy extrudate | Fatigue strength S$_2$ (MPa) | Strength ratio S$_1$/S$_2$ |
|---|---|---|
| A$_1$ | 120 | 1.0 |
| A$_2$ | 120 | 1.0 |
| A$_3$ | 120 | 1.0 |
| A$_4$ | 140 | 1.0 |
| A$_5$ | 130 | 1.0 |
| A$_6$ | 130 | 1.0 |
| A$_7$ | 130 | 1.0 |
| a$_1$ | 100 | 0.8 |
| a$_3$ | 100 | 0.9 |
| a$_2$ | 110 | 0.5 |

Figure 50:
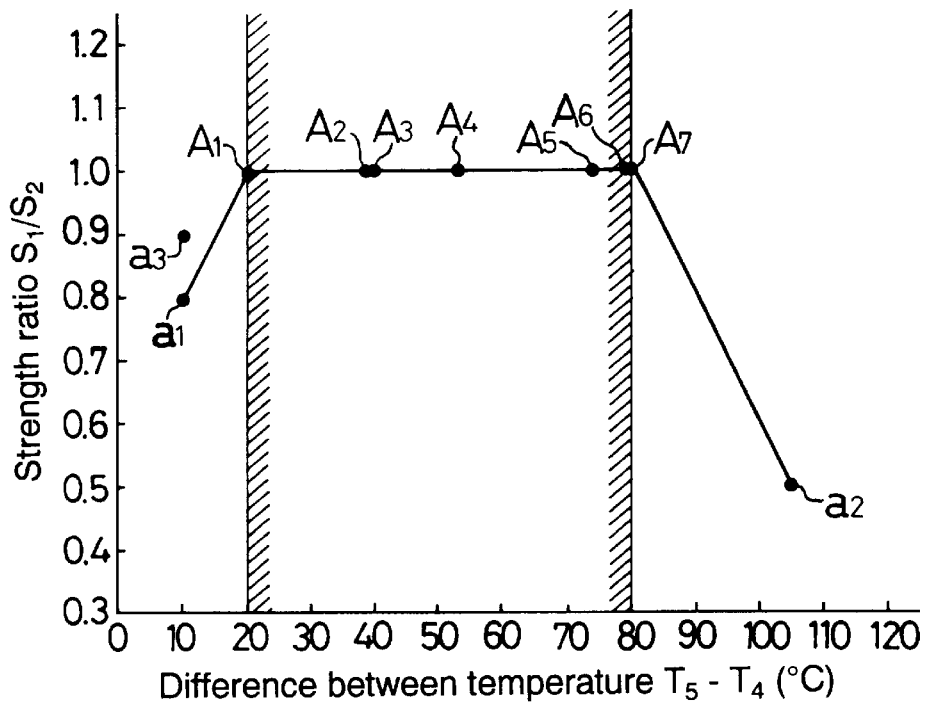
FIG. 50 is a graph illustrating the relationship between the temperature difference $T_5-T_4$ and the strength ratio $S_1/S_2$.

FIG. 50 is a graph illustrating the relationship between the difference T$_5$–T$_4$ between the temperatures and the strength ratio S$_1$/S$_2$ for the examples A$_1$ to A$_7$ and the comparative examples a$_1$ and a$_2$. In FIG. 50, points A$_1$ to A$_7$, a$_1$ and a$_2$ correspond to the cases where the examples A$_1$ to A$_7$ and the comparative examples a$_1$ and a$_2$ were used, respectively. Point a$_3$ corresponds to the case where the heating time for the comparative example a$_3$ was 20 minutes.

As can be seen from FIG. 50 and Table 13, if the examples A$_1$ to A$_7$ are used, the aluminum alloy castings A$_1$ to A$_7$ having a fatigue strength equivalent to those of the aluminum alloy extrusions A$_1$ to A$_7$ can be produced. From this, it can be also seen that the difference T$_5$–T$_4$ between the temperatures may be set in the range of 20° C.$\leq$T$_5$–T$_4$$\leq$80° C.

Embodiment V

Table 14 shows the compositions of examples A$_1$ to A$_4$ and comparative examples a$_1$ to a$_3$ of aluminum alloy materials. Each of the examples and the comparative examples was cut off from a high quality long continuous casting produced in a continuous casting process. In producing the casting, a spheroidizing treatment of a primary crystal α-Al was performed. Each of the examples and the comparative examples has a diameter of 50 mm and a length of 65 mm.

TABLE 14

| Al alloy material | Chemical constituents (% by weight) | | | | | | | | | |
|---|---|---|---|---|---|---|---|---|---|---|
| | Si | Cu | Mg | Fe | Zr | Zn | Mn | V | Ti | Balance |
| Example $A_1$ | 0.15 | 12.2 | — | 0.18 | 0.15 | — | 0.3 | 0.1 | 0.05 | Al |
| Example $A_2$ | 0.17 | 10.3 | — | 0.18 | 0.18 | — | 0.27 | 0.1 | 0.05 | Al |
| Example $A_3$ | 0.18 | 8.2 | — | 0.18 | 0.2 | — | 0.25 | 0.1 | 0.05 | Al |
| Example $A_4$ | 0.1 | 18 | — | 0.18 | 0.15 | — | 0.3 | 0.1 | 0.05 | Al |
| Comparative example $a_1$ | 7 | <0.2 | 0.55 | <0.2 | — | <0.1 | <0.1 | — | 0.12 | Al |
| Comparative example $a_2$ | 5 | 3 | 0.33 | <0.2 | — | <0.2 | <0.1 | — | 0.13 | Al |
| Comparative example $a_3$ | 7 | <0.2 | 0.35 | <0.2 | — | <0.1 | <0.1 | — | <0.2 | Al |

Figure 51:
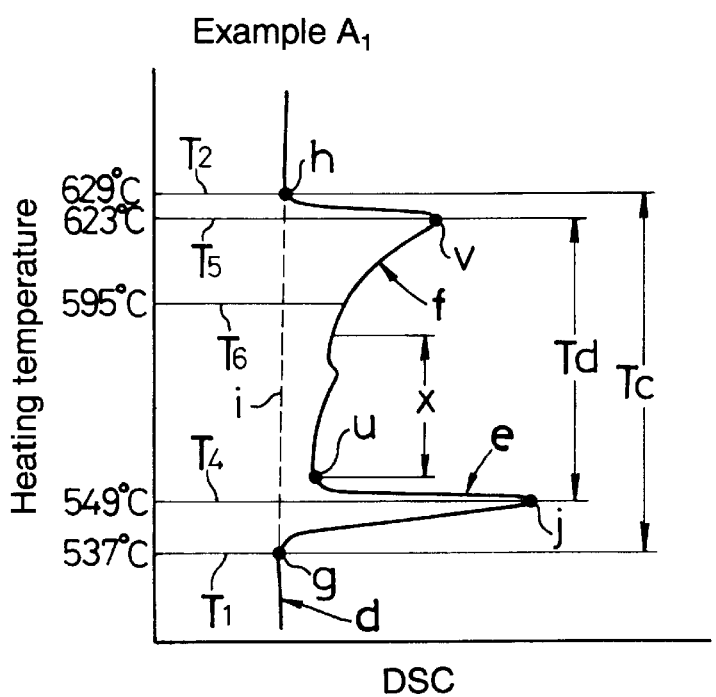
FIG. 51 illustrates an essential portion of a differential thermal analysis thermograph for an example $A_1$.

The example $A_1$ was subjected to a differential scanning calorimetry (DSC) to provide the result shown in FIG. 51. In a differential thermal analysis thermograph d shown in FIG. 51, there are a first angled endothermic section e due to an eutectic melting, and a second angled endothermic section f due to a melting of a segment having a melting point higher than an eutectic point. The second angled endothermic section f has, between a peak v thereof and a dropping end point u of the first angled endothermic section e, a gentle-sloping portion x extending along a basic line i which interconnects a rising start point g of the first angled endothermic section e and a dropping end point h of the second angled endothermic section f.

The temperature $T_1$ at the rising start point g in the first angled endothermic section e is equal to 537° C., and the temperature $T_4$ at the peak j is equal to 549° C. The temperature $T_5$ at the peak v in the second angled endothermic section f is equal to 623° C., and the temperature $T_2$ at the dropping end point h is equal to 629° C. Therefore, a solid/liquid phase-coexisting temperature range Tc (=$T_2-T_1$) between the rising start point g of the first angled endothermic section e and the dropping end point h of the second angled endothermic section f is equal to 92° C., and a peak-peak temperature range Td (=$T_5-T_4$) between the peaks j and v of the first and second angled endothermic sections e and f respectively, is equal to 74° C. In this case, the proportion Rt (Td/Tc)×100 of the peak-peak temperature range Td in the solid/liquid phase-coexisting temperature range Tc is 80%.

Then, the example $A_1$ was placed into the heating coil in the induction heating device and then rapidly heated for 4 minutes up to a casting temperature $T_6$ (=595° C.) under conditions of a frequency of 1 kHz and a maximum output power of 25 kW to prepare a semi-molten example $A_1$ having solid and liquid phases coexisting therein. In this case, the solid phase proportion was set in a range of 40% (inclusive) to 60% (inclusive).

Thereafter, the semi-molten example $A_1$ (indicated by character 5) was placed into the chamber 6 and passed through the gate 7 and charged into the cavity 4, while being pressurized under conditions of the casting temperature of 595° C., a moving velocity of the pressurizing plunger 9 of 0.2 m/sec and a mold temperature of 250° C. A pressurizing force is applied to the example $A_1$ fill in the cavity 4 by retaining the pressurizing plunger 9 at the terminate end of the stroke, and the example $A_1$ was solidified under the pressurization to provide an aluminum alloy casting $A_1$.

The examples $A_2$ to $A_4$ and the comparative examples $a_1$ to $a_3$ were also subjected to DSC, and further, using these examples and comparative examples, six aluminum alloy castings $A_2$ to $A_4$ and $a_1$ to $a_3$ were produced in the same casting process.

Figure 52:
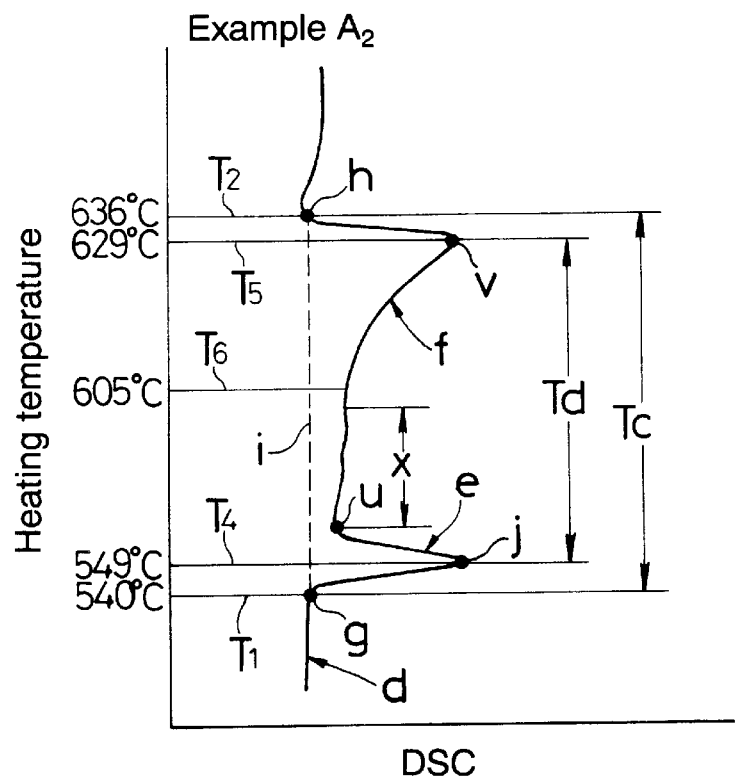
FIG. 52 illustrates an essential portion of a differential thermal analysis thermograph for an example $A_2$.
Figure 53:
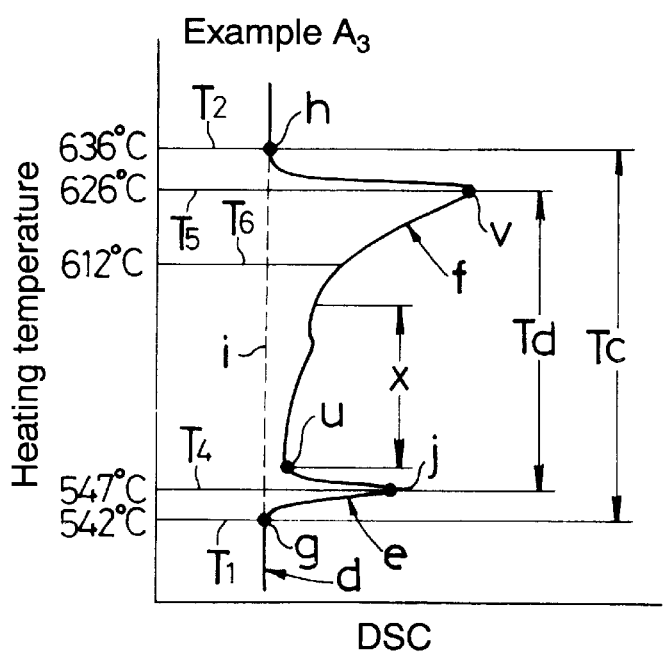
FIG. 53 illustrates an essential portion of a differential thermal analysis thermograph for an example $A_3$.
Figure 54:
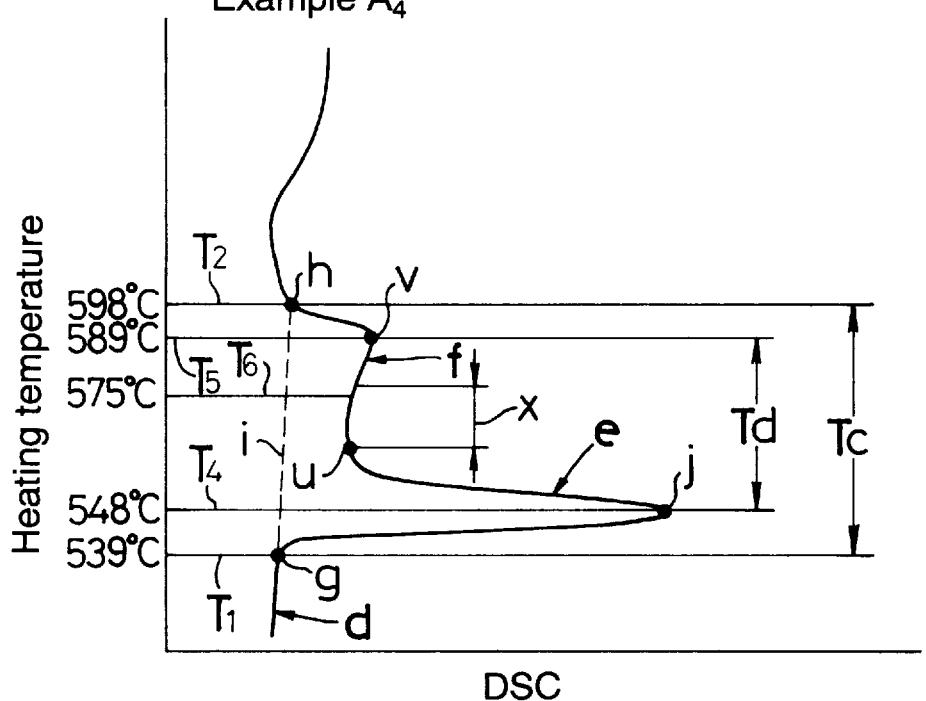
FIG. 54 illustrates an essential portion of a differential thermal analysis thermograph for an example $A_4$.
Figure 55:
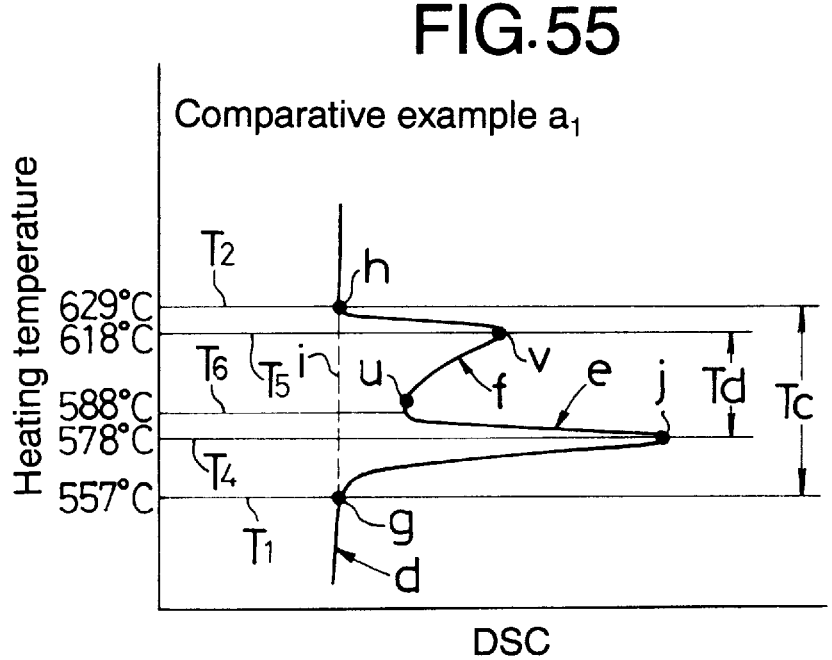
FIG. 55 illustrates an essential portion of a differential thermal analysis thermograph for a comparative example $a_1$.
Figure 56:
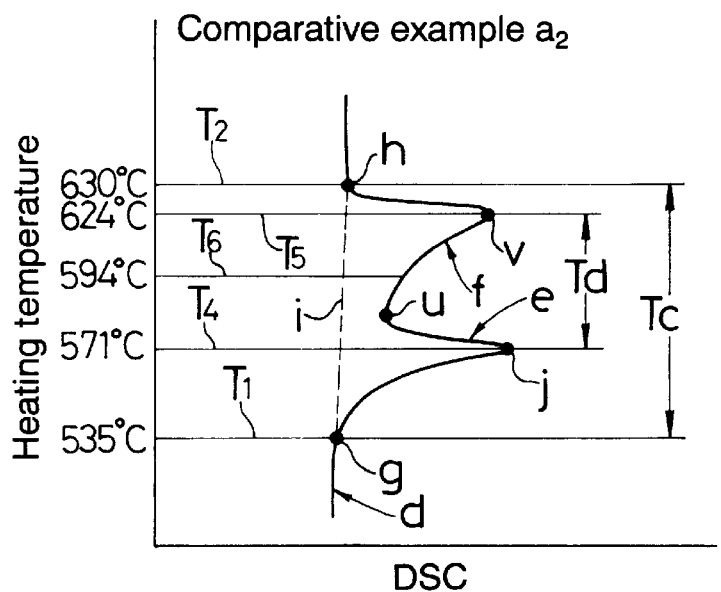
FIG. 56 illustrates an essential portion of a differential thermal analysis thermograph for a comparative example $a_2$.
Figure 57:
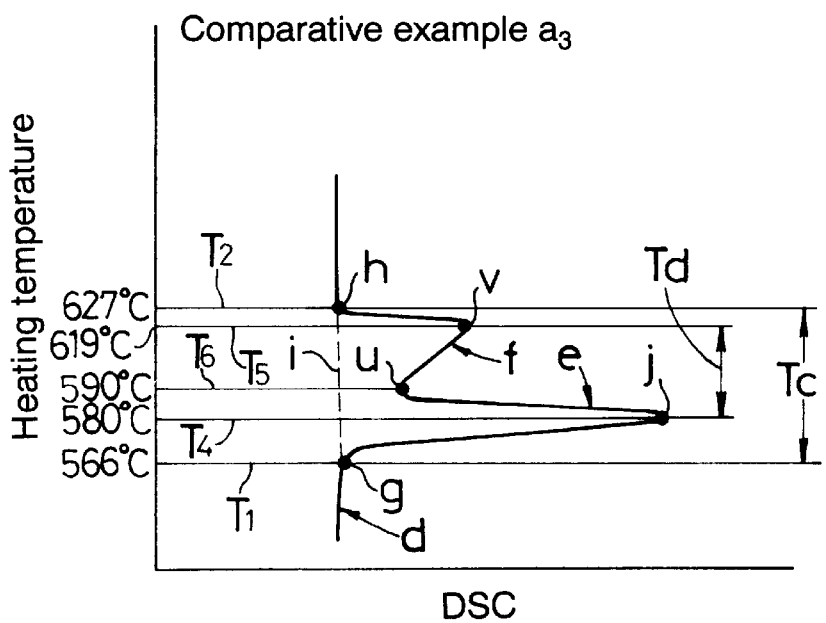
FIG. 57 illustrates an essential portion of a differential thermal analysis thermograph for a comparative example $a_3$.

FIGS. 52 to 54 show differential thermal analysis thermographs d for the examples $A_2$ to $A_4$, and FIGS. 55 to 57 show differential thermal analysis thermographs d for the comparative examples $a_1$ to $a_3$. It can be seen by the comparison of FIGS. 52 to 54 with FIGS. 55 to 57 that for each of the examples $A_2$ to $A_4$ shown in FIGS. 52 to 54, a gentle-sloping portion x exists, but for each of the comparative examples $a_1$ to $a_3$ shown in FIGS. 55 to 57, no gentle-sloping portion x exists.

Table 15 shows the solid/liquid-coexisting temperature Tc, the peak-peak temperature range Td, and the proportion Rt of the peak-peak temperature range Td in the solid/liquid phase-coexisting temperature range Tc for the examples $A_1$ to $A_4$ and the comparative examples $a_1$ to $a_3$, and the metallographic structure of the corresponding aluminum alloy castings $A_1$ to $A_4$ and $a_1$ to $a_3$.

TABLE 15

| Al alloy material | Solid/liquid phase-coexisting temperature range Tc (°C.) | Peak–peak temperature range Td (°C.) | Proportion Rt (%) |
|---|---|---|---|
| Example $A_1$ (casting $A_1$) | 92 | 74 | 80 |
| Example $A_2$ (casting $A_2$) | 96 | 80 | 83 |
| Example $A_3$ (casting $A_3$) | 94 | 79 | 84 |
| Example $A_4$ (casting $A_4$) | 59 | 41 | 69 |
| Comparative example $a_1$ (casting $a_1$) | 72 | 40 | 56 |
| Comparative example $a_2$ (casting $a_2$) | 95 | 53 | 56 |
| Comparative example $a_3$ (casting $a_3$) | 61 | 39 | 64 |

Figure 58:
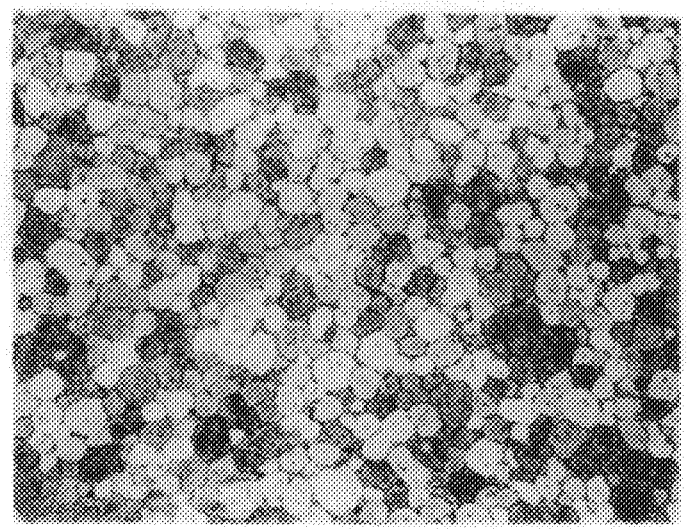
FIG. 58 is a photomicrograph showing the metallographic structure of an aluminum alloy casting $A_1$.
Figure 59:
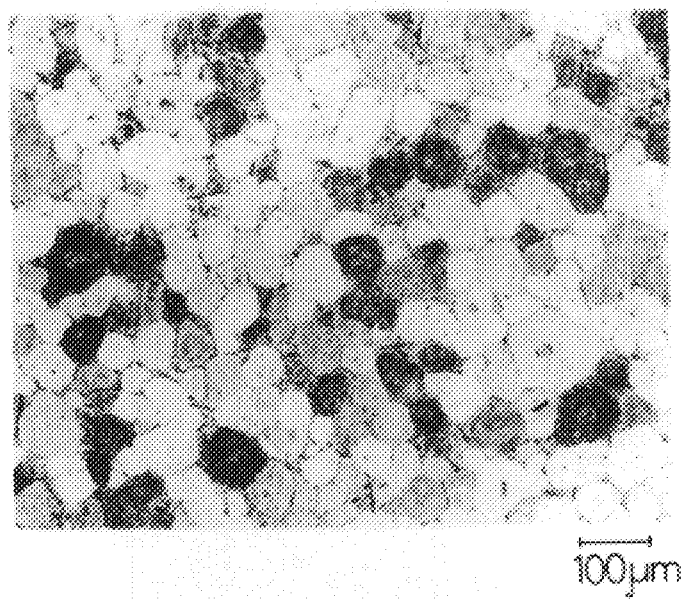
FIG. 59 is a photomicrograph showing the metallographic structure of an aluminum alloy casting $A_2$.

FIG. 58 is a photomicrograph showing the metallographic structure of the aluminum alloy casting $A_1$, and FIG. 59 is a photomicrograph showing the metallographic structure of the aluminum alloy casting $A_2$. It can be seen from FIGS. 58 and 59 that each of the examples $A_1$ and $A_2$ has an extremely uniform metallographic structure, notwithstanding it was produced by rapidly heating each of the examples $A_1$ and $A_2$.

Figure 60:
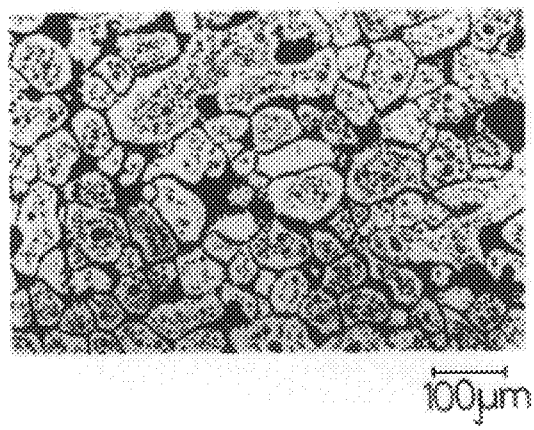
FIG. 60 is a photomicrograph showing the metallographic structure of an aluminum alloy casting $A_4$.

FIG. 60 is a photomicrograph showing the metallographic structure of the aluminum alloy casting $A_4$. As apparent from FIG. 60, a somewhat larger α-Al solidified phase is observed in the aluminum alloy casting $A_4$, but the metallographic structure of the aluminum alloy casting $A_4$ is substantially uniform.

Figure 61:
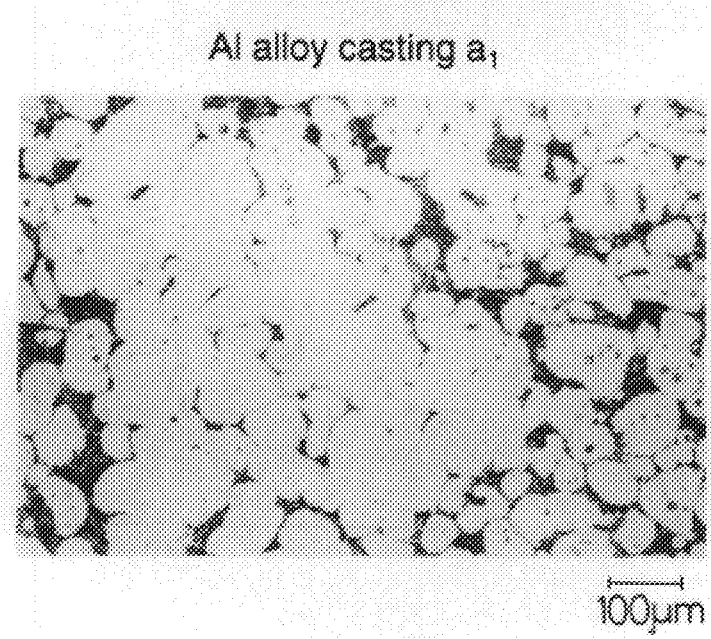
FIG. 61 is a photomicrograph showing the metallographic structure of an aluminum alloy casting $a_1$.

FIG. 61 is a photomicrograph showing the metallographic structure of the aluminum alloy casting $a_1$. As apparent from FIG. 61, the distribution of the liquid phase in the aluminum alloy casting $a_1$ was not uniformized due to the rapid heating of the comparative example $a_1$ and as a result, the α-Al solidified phases were agglomerated to provide the non-uniform metallographic structure. The same is true for the aluminum alloy castings $a_2$ and $a_3$.

The following can be seen from the above results. In order to produce an aluminum alloy casting having a uniform metallographic structure, it is required that the second angled endothermic section f have a gentle-sloping portion x in the differential thermal analysis thermograph d, as described above, and the proportion Rt of the peak-peak temperature range Td in the solid/liquid coexisting temperature Tc be in the range of Rt≧69%, as in the examples $A_1$ to $A_4$.

In the examples $A_1$ to $A_4$ having such a thermal characteristic, the temperature range between the dropping end point of the first angled endothermic section e and the peak v of the second angled endothermic section f is wide and therefore, the gellation of the outer periphery of the solid phase is promoted. This improves the compatibility between the solid and liquid phases and hence, it is possible to avoid a disadvantage of the generation of voids on the order of a micron at a boundary between the solid and liquid phases.

For comparison, using the examples $A_1$ to $A_4$ and the comparative examples $a_1$ to $a_3$, seven aluminum alloy castings $B_1$ to $B_4$ and $b_1$ to $b_3$ corresponding to the examples $A_1$ to $A_4$ and the comparative examples $a_1$ to $a_3$, respectively were produced in the same casting process under the same conditions, except that the examples $A_1$ to $A_4$ and the comparative examples $a_1$ to $a_3$ were heated (in a normally heating manner) up to the casting temperature $T_6$ under conditions of a frequency of 1 kHz, a maximum power output of 12 kW and a heating time of 7 minutes.

The metallographic structure of each of the aluminum alloy castings $B_1$ to $B_4$ and $b_1$ to $b_3$ was observed by a microscope, and the result showed that the metallographic structure was uniform.

Then, each of the aluminum alloy castings $A_1$ to $A_4$, $B_1$ to $B_4$, $a_1$ to $a_3$ and $b_1$ to $b_3$ was subjected to a T6 treatment under conditions shown in Table 16.

TABLE 16

| Al alloy casting | T6 treatment | | | | |
|---|---|---|---|---|---|
| | Solution treatment | | | Aging treatment | |
| | Temperature (°C.) | Time (hr) | Cooling type | Temperature (°C.) | Time (hr) |
| $A_1$, $B_1$ $A_2$, $B_2$ $A_3$, $B_3$ $A_4$, $B_4$ | 525 | 5 | Water cooling | 190 | 18 |
| $a_1$, $b_1$ $a_2$, $b_2$ $a_3$, $b_3$ | 540 515 540 | 5 | Water cooling | 170 | 5 10 5 |

For the purpose of carrying out a fatigue test, ten test pieces each including a parallel portion having a diameter of 4 mm and a length of 20 mm were fabricated from each of the aluminum alloy castings $A_1$ to $A_4$, $B_1$ to $B_4$, $a_1$ to $a_3$ and $b_1$ to $b_3$ resulting from the T6 treatment. These test pieces were subjected to a test with different stress amplitudes using, an electric hydraulic fatigue tester to determine the number of repetitions up to the fracture. From this data, the fatigue strength at the number of $10^7$ repetitions was determined. Table 17 shows the results. In the strength ratio heading shown in Table 17, "rapid heating/normal heating" means that the fatigue strength value, for example, for the aluminum alloy $A_1$ produced through the rapid heating, is divided by the fatigue strength value for the aluminum alloy $B_1$ produced through the normal heating.

TABLE 17

| Al alloy casting | Fatigue strength (Mpa) | | Fatigue strength ratio of rapid heating/normal heating |
|---|---|---|---|
| | Rapid heating | Normal heating | |
| $A_1$ | 130 | — | 1.0 |
| $B_1$ | — | 130 | |
| $A_2$ | 130 | — | 1.0 |
| $B_2$ | — | 130 | |
| $A_3$ | 130 | — | 1.0 |
| $B_3$ | — | 130 | |
| $A_4$ | 100 | — | 0.95 |
| $B_4$ | — | 105 | |
| $a_1$ | 100 | — | 0.8 |
| $b_1$ | — | 120 | |
| $a_2$ | 110 | — | 0.8 |
| $b_2$ | — | 140 | |
| $a_3$ | 100 | — | 0.8 |
| $b_3$ | — | 120 | |

Figure 62:
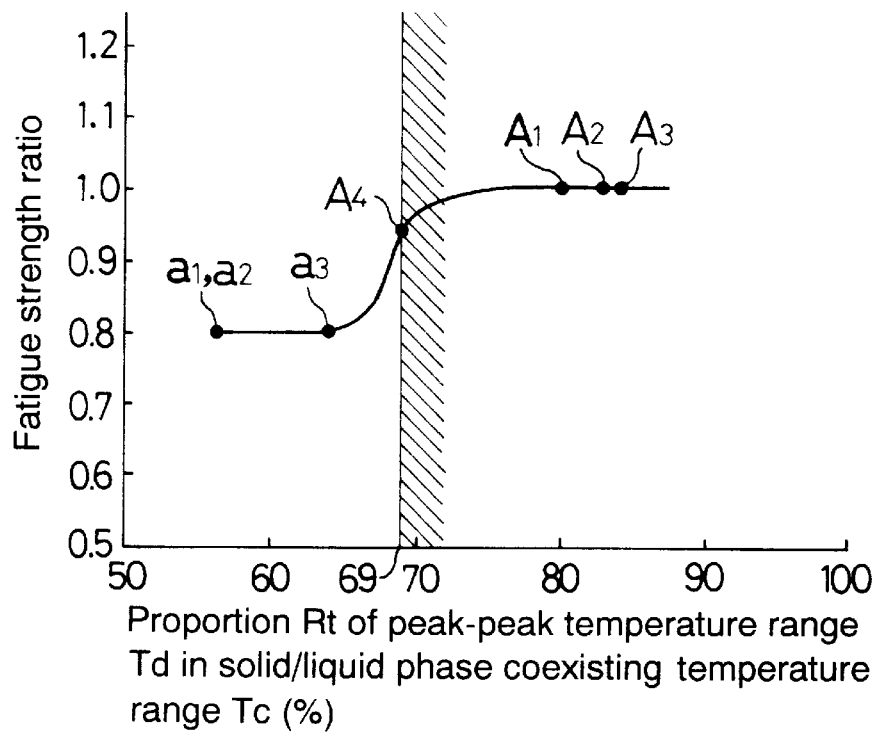
FIG. 62 is a graph illustrating the relationship between the proportion Rt of a peak-peak temperature range Td in a solid-liquid phase coexisting temperature range Tc and the fatigue strength ratio.

FIG. 62 is a graph illustrating the relationship between the proportion Rt of the peak-peak temperature range Td in the solid/liquid-coexisting temperature Tc and the fatigue strength ratio for the aluminum alloy castings $A_1$ and $B_2$ and the like shown in Tables 15 and 17. In FIG. 62, points $A_1$ to $A_4$ correspond to the cases where the examples $A_1$ to $A_4$ were used, and points $a_1$ to $a_3$ correspond to the cases where the comparative examples $a_1$ to $a_3$ were used.

As apparent from Tables 15 and 17 and FIG. 62, each of the aluminum alloy castings $A_1$ to $A_4$ produced using the examples $A_1$ to $A_4$ through the rapid heating has a fatigue strength equivalent to those of the aluminum alloy castings $B_1$ to $B_4$ produced through the normal heating. This is because each of the aluminum alloy castings $A_1$ to $A_4$ has a uniform metallographic structure, as do the aluminum alloy castings $B_1$ to $B_4$. The uniformization of the metallographic structure is due to the fact that the proportion Rt in the examples $A_1$ and the like is equal to or greater than 69% (Rt≧69%).

On the other hand, each of the aluminum alloy castings $a_1$ to $a_3$ produced using the comparative examples $a_1$ to $a_3$ through the rapid heating has a low fatigue strength, as compared with the aluminum alloy castings $b_1$ to $b_3$ produced through the normal heating. This is because the metallographic structure of the aluminum alloy castings $a_1$ to $a_3$ is non-uniform. The non-uniformization of the metallographic structure is due to the fact that the proportion Rt in the comparative examples $a_1$ and the like is smaller than 69% (Rt<69%).

Embodiment VI

Table 18 shows the compositions of aluminum alloy materials $A_1$ to $A_5$. Each of the examples $A_1$ to $A_5$ was cut off from a high quality long continuous casting produced in a continuous casting process. In producing the casting, a spheroidizing treatment of a primary crystal α-Al was performed. Each of the examples $A_1$ to $A_5$ has a diameter of 50 mm and a length of 65 mm.

TABLE 18

| Al alloy material | Chemical constituents (% by weight) | | | | | |
|---|---|---|---|---|---|---|
| | Si | Cu | Mg | Fe | Ti | balance |
| $A_1$ | 0.15 | 12.2 | — | 0.18 | 0.15 | Al |
| $A_2$ | 5.3 | 2.9 | 0.3 | 0.12 | 0.01 | Al |
| $A_3$ | 7 | <0.2 | 0.45 | <0.2 | <0.2 | Al |
| $A_4$ | 0.12 | 10.3 | — | 0.1 | 0.05 | Al |
| $A_5$ | 0.18 | 8.2 | — | 0.18 | 0.05 | Al |

Figure 63:
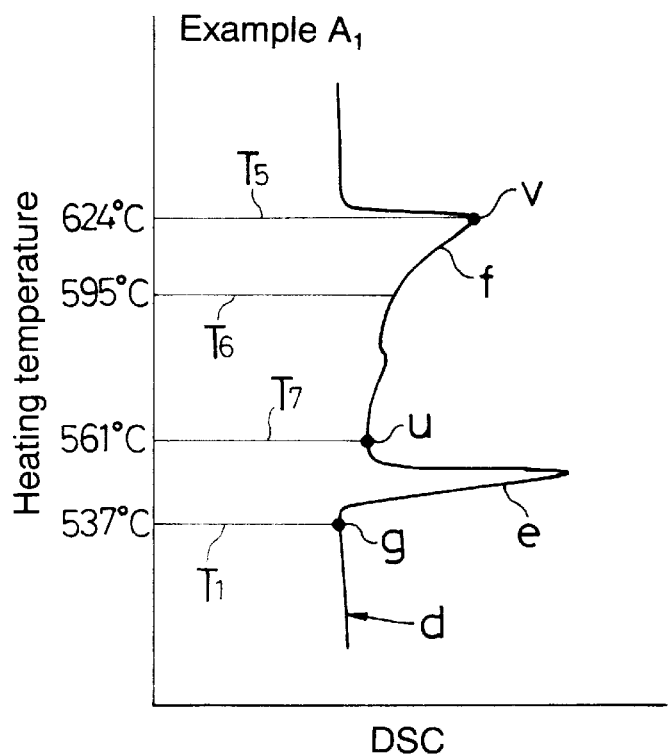
FIG. 63 illustrates an essential portion of a differential thermal analysis thermograph for an example $A_1$.

The example $A_1$ was subjected to a differential scanning calorimetry (DSC) to provide the result shown in FIG. 63. In the differential thermal analysis thermograph d of FIG. 63, there are a first angled endothermic section e due to an eutectic melting, and a second angled endothermic section f due to a melting of a segment having a melting point higher than an eutectic point. The temperature $T_1$ at a rising start point g in the first angled endothermic section e is equal to 537° C., and the temperature $T_7$ at a dropping end point u is equal to 561° C. The temperature $T_5$ in a peak v in the second angled endothermic section f is equal to 624° C.

Figure 64:
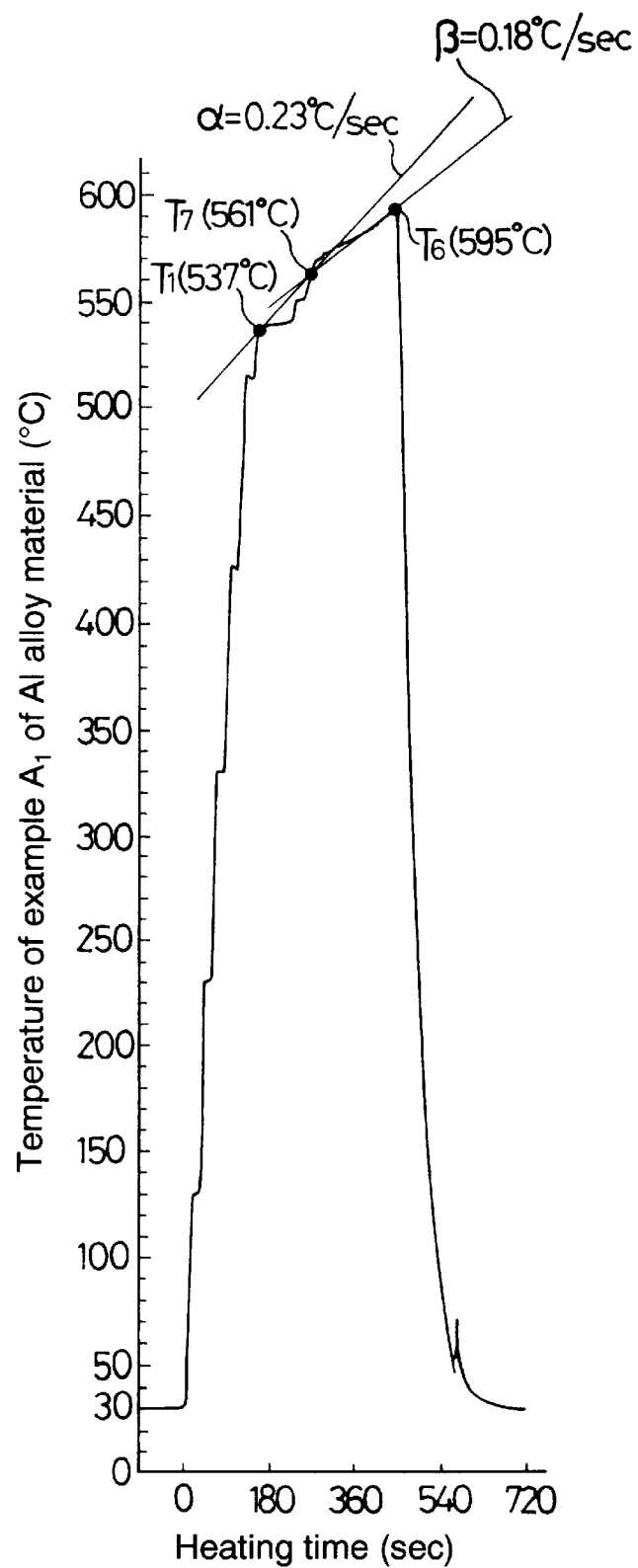
FIG. 64 is a graph illustrating the relationship between the heating time and the temperature of the example $A_1$ of an aluminum alloy material.
Figure 65:
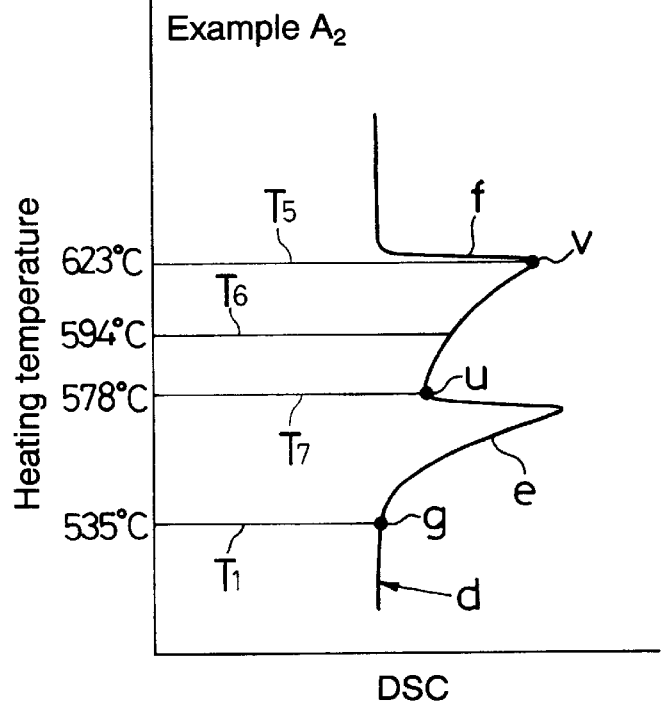
FIG. 65 illustrates an essential portion of a differential thermal analysis thermograph for an example $A_2$.
Figure 66:
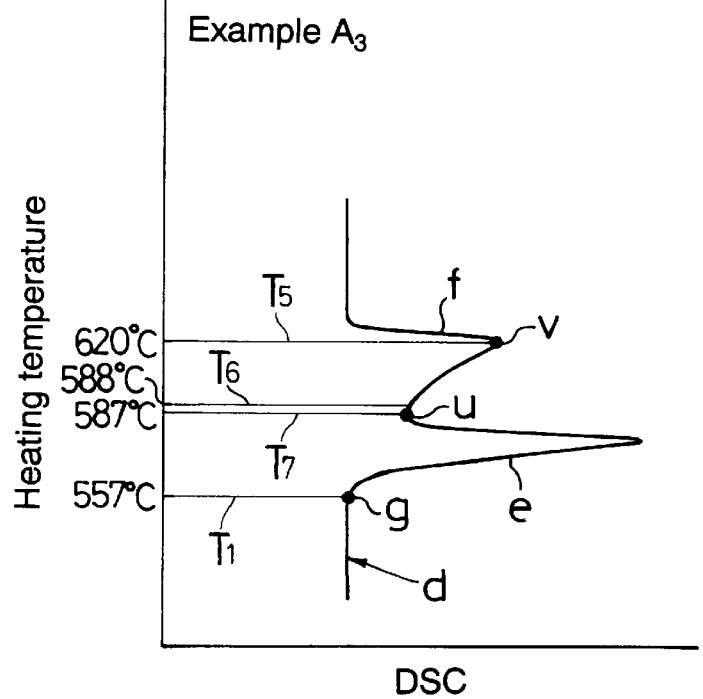
FIG. 66 illustrates an essential portion of a differential thermal analysis thermograph for an example $A_3$.
Figure 67:
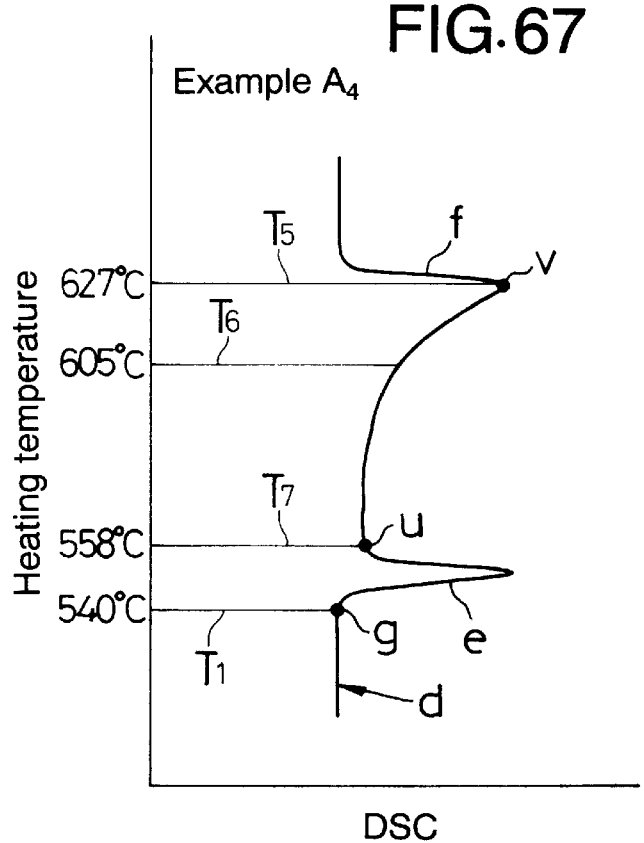
FIG. 67 illustrates an essential portion of a differential thermal analysis thermograph for an example $A_4$.
Figure 68:
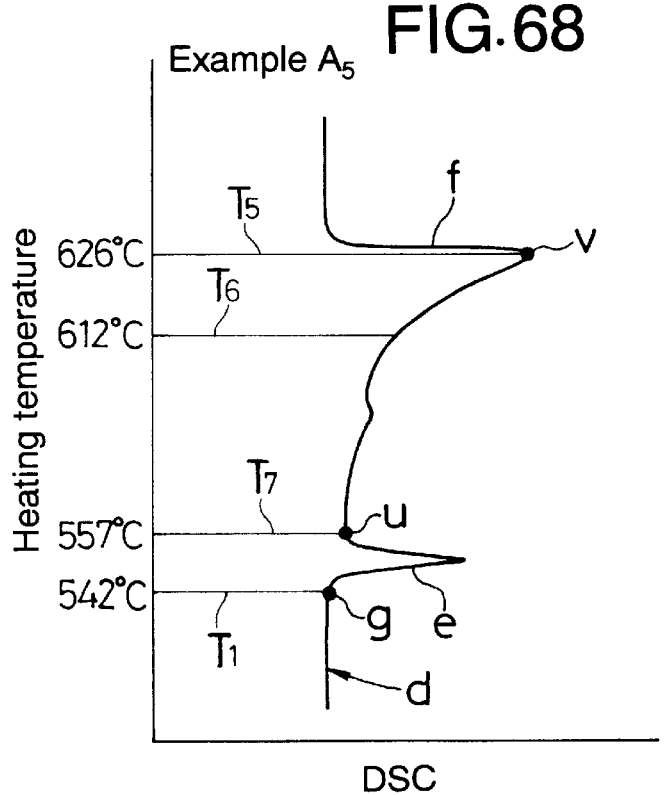
FIG. 68 illustrates an essential portion of a differential thermal analysis thermograph for an example $A_5$.

Then, the example $A_1$ was placed in a upstanding fashion into the heating coil in the induction heating device and then heated up to a casting temperature $T_6$ of 595° C. under conditions shown in FIG. 64 to prepare a semi-molten example $A_1$ having solid and liquid phases coexisting therein. When the temperature of the example $A_1$ was in a range of 30° C. to the temperature $T_1$ of 537° C. at the rising start point, the frequency was set at 1 kHz, and the power output was set at 20 kW. When the temperature of the example $A_1$ was in a range of the temperature $T_1$ of 537° C. at the rising start point g to the temperature $T_7$ of 561° C. at the dropping end point u, the frequency was set at 1 kHz, and the power output was set at 15 kW. Further, when the temperature of the example $A_1$ was in a range of the temperature $T_7$ of 561° C. at the dropping end point u to the casting temperature $T_6$, the frequency was set at 1 kHz, and the power output was set at 3 kW. Thus, the average temperature rising rate $\alpha$ for the example $A_1$ between the rising start point g and the dropping end point u was controlled to 0.23° C./sec, while the average temperature rising rate $\beta$ for the example $A_1$ between the dropping end point u and the casting temperature $T_6$ was controlled to 0.18° C./sec. In this case, the solid phase proportion in the example $A_1$ was in a range of 40% (inclusive) to 60% (inclusive). The measurement of the temperature of the example $A_1$ was performed by inserting a thermocouple into a measuring hole opened at the center of the lower surface of the example $A_1$.

Thereafter, the semi-molten example $A_1$ (indicated by character 5) was placed into the chamber 6 and passed through the gate 7 and charged into the cavity 4, while being pressurized under conditions of a casting temperature $T_6$ of 595° C., a moving velocity of the pressurizing plunger 9 of 0.2 m/sec and a mold temperature of 250° C. A pressurizing force is applied to the example $A_1$ fill in the cavity 4 by retaining the pressurizing plunger 9 at the terminate end of the stroke, and the example $A_1$ was solidified under the pressurization to provide an aluminum alloy casting $A_{11}$.

Using the example $A_1$, an aluminum alloy casting $A_{12}$ was also produced in a similar casting manner, except that the average temperature rising rates $\alpha$ and $\beta$ were changed.

The examples $A_2$ to $A_5$ were also subjected to DSC, and further, using these examples $A_2$ to $A_5$, eight aluminum alloy castings $A_{21}$, $A_{31}$, $A_{41}$, $A_{51}$, $A_{22}$, $A_{32}$, $A_{42}$ and $A_{52}$ were produced by the same casting process. FIGS. 65 to 68 show differential thermal analysis thermographs d for the examples $A_2$ to $A_5$, respectively.

Each of the aluminum alloy castings $A_{11}$ to $A_{51}$ and $A_{12}$ to $A_{52}$ was observed by a microscope to determine the presence or absence of on the order of a micron and the size of α-Al.

Figure 69A:
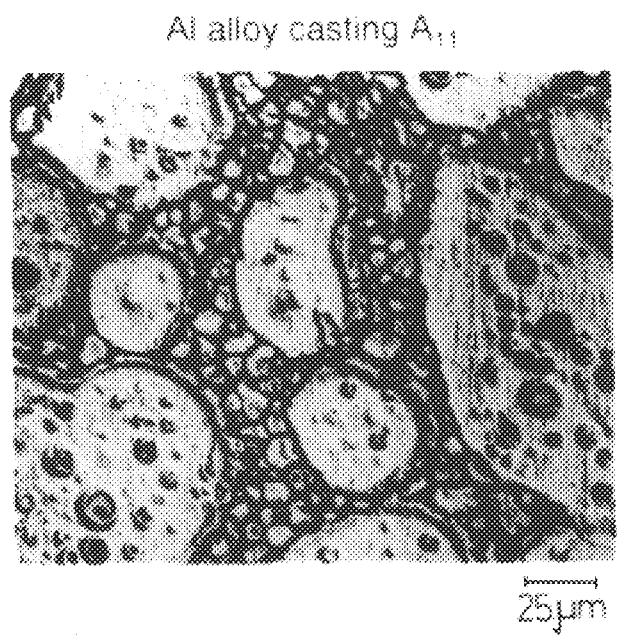
FIG. 69A is a photomicrograph showing the metallographic structure of an aluminum alloy casting $A_{11}$.

FIG. 69A is a photomicrograph showing the metallographic structure of the aluminum alloy casting $A_{11}$, in which a relatively large granular portion is α-Al. It can be seen from FIG. 69A that voids as described were not generated in the aluminum alloy casting $A_{11}$.

Figure 69B:
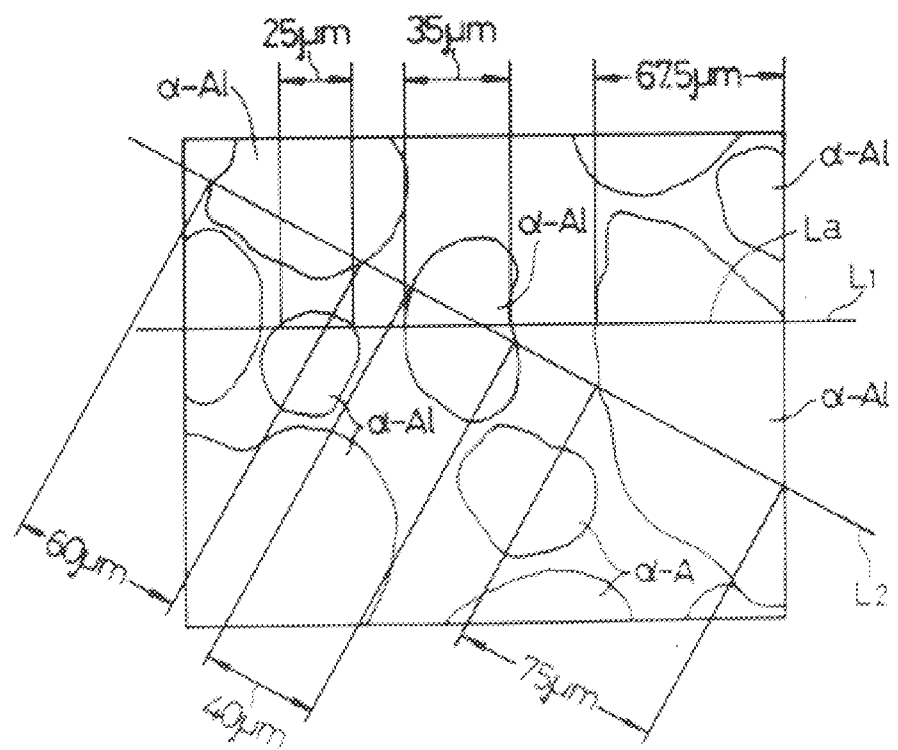
FIG. 69B is a diagram for explaining how to measure the size of $\alpha$-Al.

FIG. 69B shows how to measure the size of an α-Al phase. In measuring the size of the α-Al phase, two straight lines $L_1$ and $L_2$ intersecting each other are first drawn so as to traverse a plurality of α-Al phases and then, the length of a line segment La of each of the straight lines $L_1$ and $L_2$ in each of the α-Al phases is measured, whereby an average value of the lengths is determined. Thus, the average value of the lengths of all the line segments La of one the straight line $L_1$ is (25 μm+35 μm+67.5 μm)/3=42.5 μm, and the average value of the lengths of all the line segments La of the other straight line $L_2$ is (60 μm+40 μm+75 μm)/3≅58.3 μm. Thereafter, an average value of such average values is further determined and defined as the size of the α-Al phase. Thus, the size of the α-Al phase is (42.5 μm+58.3 μm)/2≅50 μm.

Figure 70A:
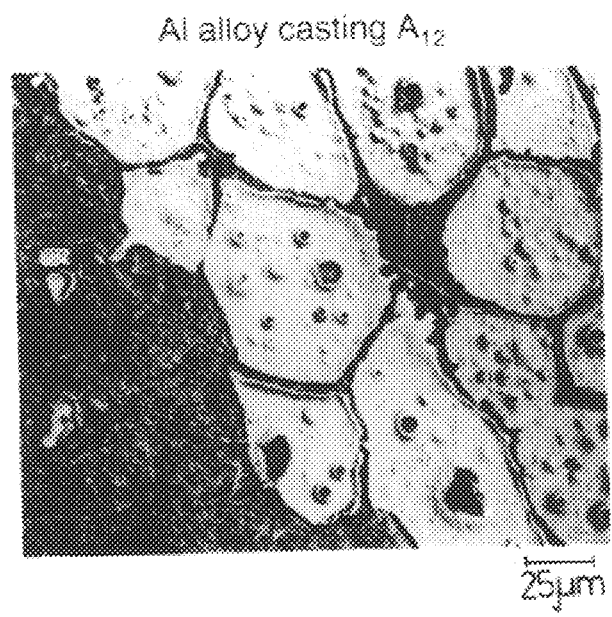
FIG. 70A is a photomicrograph showing the metallographic structure of an aluminum alloy casting $A_{12}$.
Figure 70B:
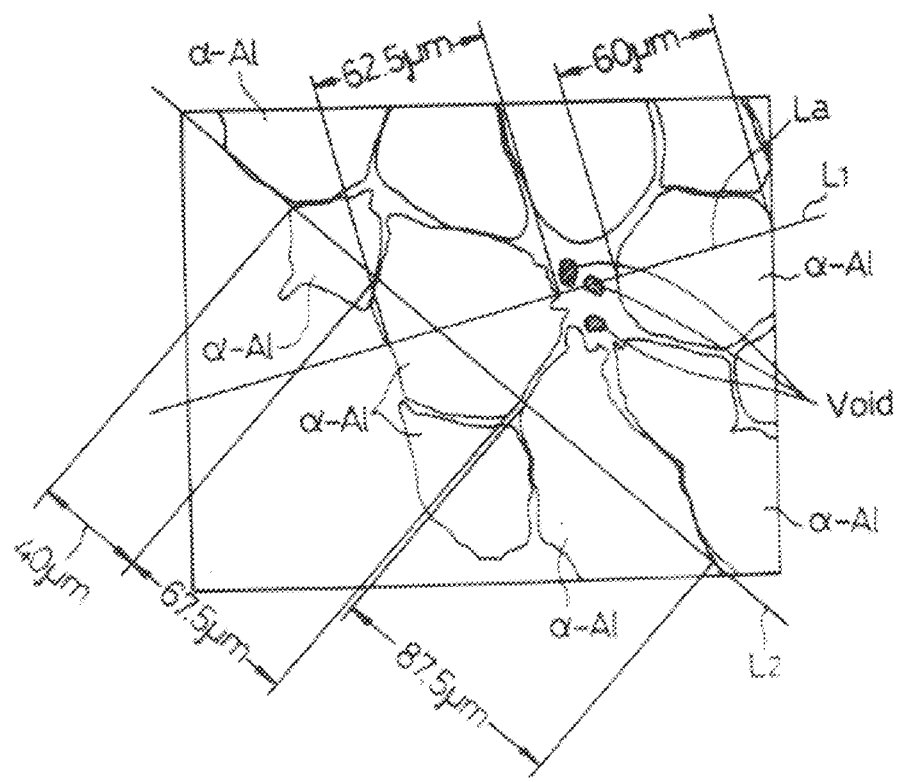
FIG. 70B is a diagram for explaining how to measure the size of $\alpha$-Al.

FIG. 70 is a photomicrograph showing the metallographic structure of the aluminum alloy casting $A_{12}$, in which a relatively large portion is an α-Al phase. It can be seen that voids as described above were generated in the aluminum alloy casting $A_{12}$, as also shown in FIG. 70B. In this case, an average value of the lengths of all the line segments La of the straight line $L_1$ is (62.5 μm+60 μm)/2=61.25 μm, and an average value of the lengths of all the line segments La of the other straight line $L_2$ is (40 μm+67.5 μm+87.5 μm)/3≅65 m. Therefore, the size of the α-Al phase is (61.25 μm+65 μm)/2≅63 μm.

Each of the aluminum alloy castings $A_{11}$ to $A_5$ and $A_{12}$ to $A_{52}$ was subjected to a T6 treatment. Then, for the purpose of carrying out a fatigue test, ten test pieces each including a parallel portion having a diameter of 4 mm and a length 20 mm were fabricated from each of the aluminum alloy castings $A_{11}$ to $A_{51}$ and $A_{12}$ to $A_{52}$ resulting from the T6 treatment. Each of the test pieces was subjected to a test with different stress amplitudes using an electric hydraulic fatigue tester to determine the number of repetitions up to the fracture. From this data, the fatigue strength at $10^7$ repetitions was determined.

Table 19 shows the average temperature rising rates $\alpha$ and $\beta$, the ratio $\alpha/\beta$, the size of the α-Al phase, the presence or absence of voids and the fatigue strength for the aluminum alloy castings $A_{11}$ to $A_{51}$ and $A_{12}$ to $A_{52}$.

TABLE 19

| Al alloy casting | Average temperature rising rate α (°C./sec) | Average temperature rising rate β (°C./sec) | Ratio α/β | Size of α-Al (μm) | Presence and absence of voids | Fatigue strength (MPa) |
|---|---|---|---|---|---|---|
| $A_{11}$ | 0.23 | 0.18 | 1.3 | 50 | absence | 130 |
| $A_{12}$ | 0.18 | 0.20 | 0.9 | 63 | presence | 90 |
| $A_{21}$ | 0.31 | 0.29 | 1.1 | 150 | absence | 140 |
| $A_{22}$ | 0.30 | 0.32 | 0.9 | 150 | presence | 100 |
| $A_{31}$ | 0.34 | 0.12 | 2.8 | 110 | absence | 110 |
| $A_{32}$ | 0.14 | 0.18 | 0.8 | 129 | presence | 90 |
| $A_{41}$ | 1.40 | 0.26 | 5.4 | 120 | absence | 130 |
| $A_{42}$ | 0.26 | 0.32 | 0.8 | 140 | presence | 90 |
| $A_{51}$ | 0.58 | 0.19 | 3.1 | 140 | absence | 130 |
| $A_{52}$ | 0.30 | 0.36 | 0.8 | 150 | presence | 90 |

Figure 71:
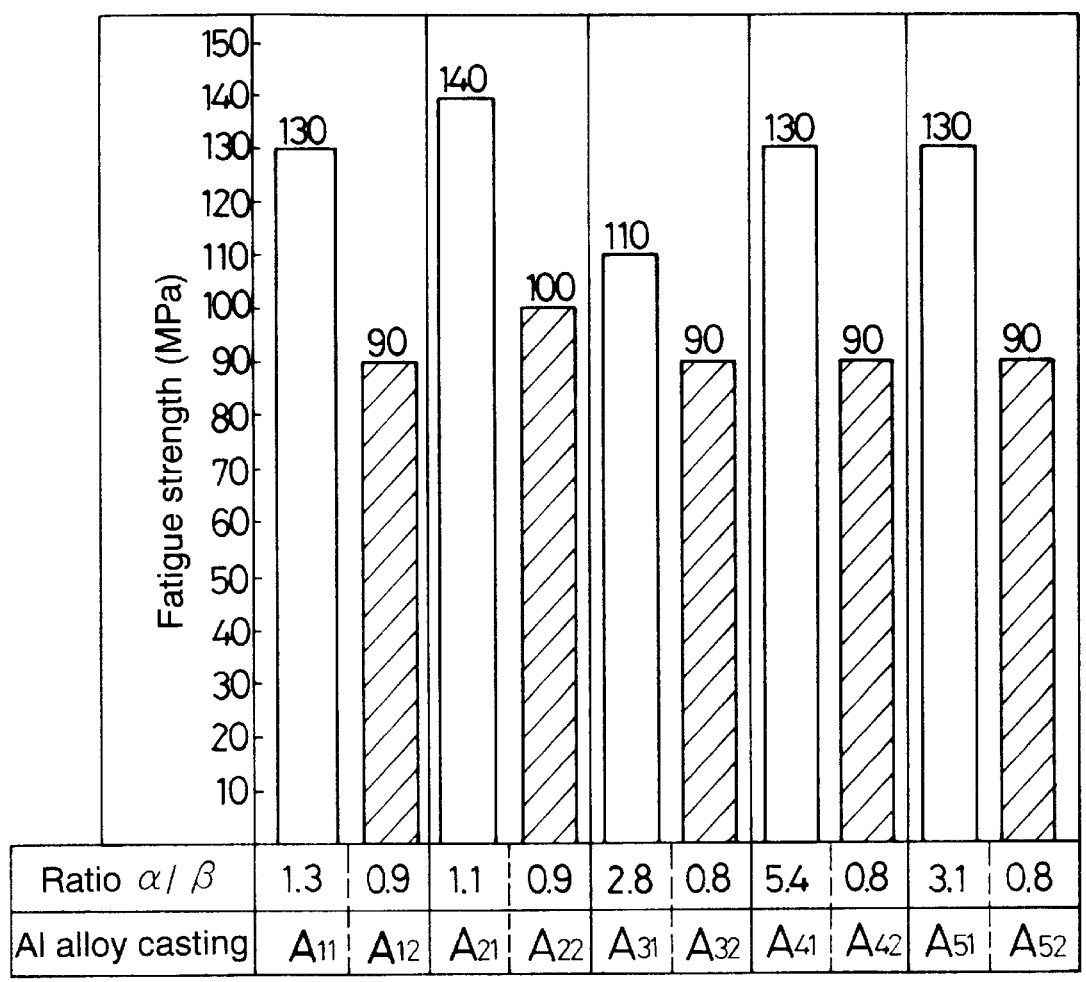
FIG. 71 is a graph illustrating fatigue strengths of various aluminum alloy castings.

FIG. 71 is a graph illustrating the relationship between the ratio α/β and the fatigue strength for the aluminum alloy castings $A_{11}$ to $A_{51}$ and $A_{12}$ to $A_{52}$ as taken from Table 19.

As apparent from Table 19 and FIG. 71, each of the aluminum alloy castings $A_{11}$ to $A_{51}$ produced with the ratio α/β between the temperature rising rates α and β set in a range of α/β>1, has an enhanced fatigue strength, as compared with the corresponding aluminum alloy castings $A_{12}$ to $A_{52}$.

As can be seen by comparing of the aluminum alloy castings $A_{11}$ and $A_{12}$; $A_{31}$ and $A_{32}$; $A_{41}$ and $A_{42}$; $A_{51}$ and $A_{52}$ with each other, the size of the α-Al phase can be maintained smaller, when the average temperature rate α is higher. The aluminum alloy castings $A_{21}$ and $A_{22}$ have the same size of the α-Al phase, because of the substantially equal average temperature rising rate.

As can be also seen by comparing the aluminum alloy castings $A_{11}$ and $A_{12}$; $A_{31}$ and $A_{32}$; $A_{41}$ and $A_{42}$; $A_{51}$ and $A_{52}$ with each other, it is possible to prevent the generation of voids on the order of a micron by setting the average temperature rising rates α and β, so that the average temperature rising rate α is lower than the average temperature rising rate β. This is attributable to the fact that the profile of temperature of the liquid phase was uniformized, and that the outer periphery of the solid phase was gelled to provide an improved compatibility between the solid and liquid phases.

Embodiment VII

Table 20 shows the composition of an A357 material which is an aluminum alloy material. The aluminum alloy material was cut off from a high quality long continuous casting produced in a continuous casting process. In producing the casting, the spheroidizing treatment of a primary crystal α-Al was performed. The aluminum alloy material has a diameter of 50 mm and a length of 65 mm.

TABLE 20

| Al alloy material | Chemical constituents (% by weight) | | | | |
|---|---|---|---|---|---|
| | Si | Mg | Fe | Sr | balance |
| | 7.9 | 0.57 | 0.1 | 0.034 | Al |

Figure 72:
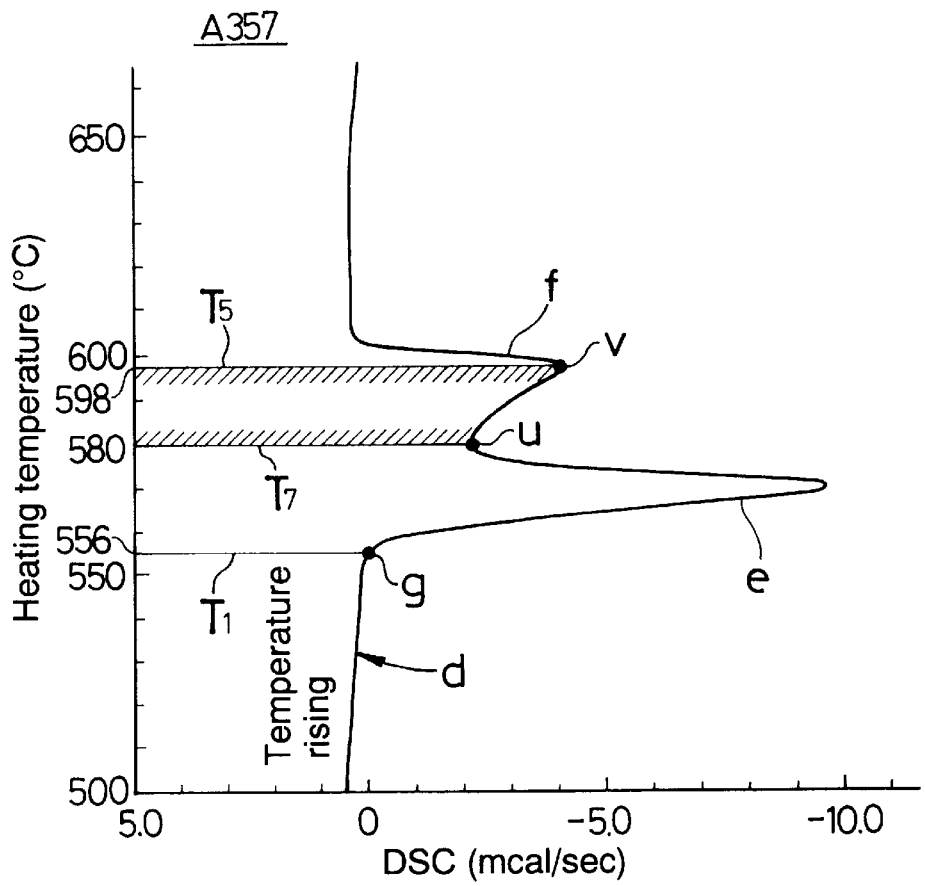
FIG. 72 is a differential thermal analysis thermograph for an aluminum alloy material.

The aluminum alloy material was subjected to a differential scanning calorimetry (DSC) to provide a result shown in FIG. 72. In the differential thermal analysis thermograph d of FIG. 72, there are a first angled endothermic section e due to an eutectic melting, and a second angled endothermic section f due to a melting of a segment having a melting point higher than an eutectic point. The temperature $T_1$ at a rising start point g in the first angled endothermic section e is equal to 556° C., and the temperature $T_7$ at a dropping end point u is equal to 580° C. The temperature $T_5$ at a peak v in the second angled endothermic section f is equal to 598° C.

Then, the example $A_1$ was placed into the heating coil in the induction heating device and then heated under conditions of a frequency of 1 kHz and a maximum power output of 30 kW to prepare a semi-molten example $A_1$ having solid and liquid phases coexisting therein. In this case, the solid phase proportion was set in a range of 40% (inclusive) to 60% (inclusive).

Thereafter, the semi-molten example 5 was placed into the chamber 6 and passed through the gate 7 and charged into the cavity 4, while being pressurized under conditions of the casting temperature of 595° C., a moving velocity of the pressurizing plunger 9 of 0.2 m/sec and a mold temperature of 250° C. A pressurizing force is applied to the semi-molten aluminum alloy material 5 fill in the cavity 4 by retaining the pressurizing plunger 9 at the terminate end of the stroke, and the semi-molten aluminum alloy material 5 was solidified under the pressurization to provide an aluminum alloy casting $A_1$.

Five aluminum alloy castings $A_2$ to $A_7$ were also produced in the casting process under the same conditions as those described above, except that the casting temperature $T_6$ was varied.

Each of the aluminum alloy castings $A_1$ to $A_7$ was subjected to a T6 treatment which comprises heating for 5 hours at 540° C. followed by water cooling, and heating for 5 hours at 170° C. following by water cooling. A tensile test piece including a parallel portion having a diameter of 4 mm and a length of 20 mm and a JIS No. 3 Charpy impact test piece were fabricated from each of the aluminum alloy castings $A_1$ to $A_7$ and subjected to a tensile test and a Charpy impact test.

Table 21 shows the casting temperature $T_6$, the test results and the like for the aluminum alloy castings $A_1$ to $A_7$.

TABLE 21

| Al alloy casting | Casting temperature $T_6$ (°C.) | Cooling velocity during eutectic reaction (°C./sec) | Presence or absence of primary crystal Si | Tensile strength (MPa) | 0.2% proof strength (MPa) | Breaking extension (%) | Charpy impact value (J/cm²) |
|---|---|---|---|---|---|---|---|
| $A_1$ | 595 | 77 | absence | 325 | 265 | 12 | 6 |
| $A_2$ | 590 | 79 | absence | 320 | 260 | 12 | 6.2 |
| $A_3$ | 585 | 81 | absence | 319 | 254 | 11 | 5.8 |
| $A_4$ | 580 | 83 | absence | 315 | 250 | 9 | 5.1 |
| $A_5$ | 577 | 85 | presence | 342 | 311 | 7 | 3.9 |
| $A_6$ | 575 | 85 | presence | 345 | 320 | 6 | 3.5 |
| $A_7$ | 570 | 86 | presence | 350 | 325 | 5 | 3 |

Figure 73:
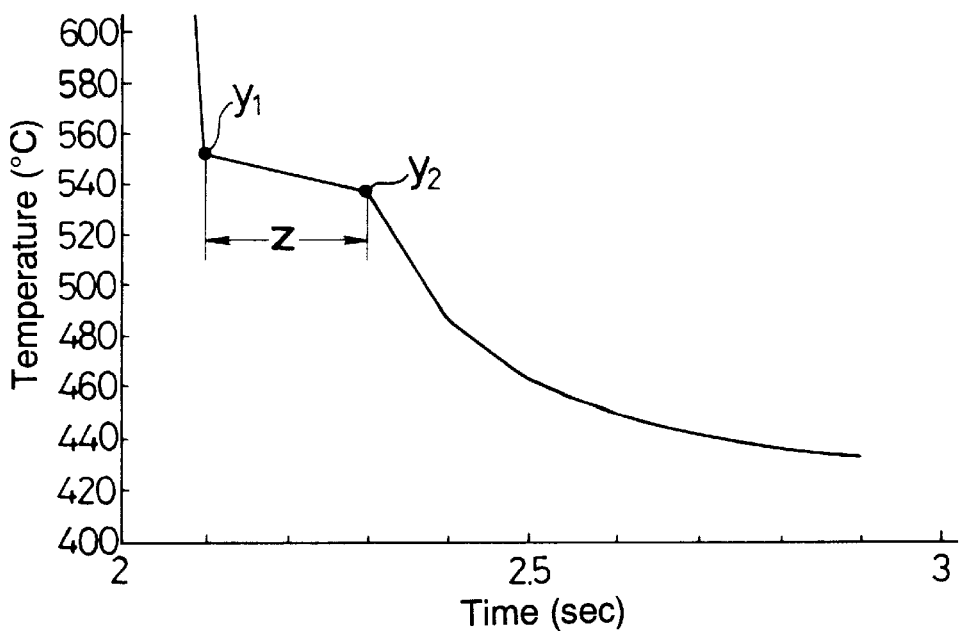
FIG. 73 illustrates an essential portion of a cooling curve for the aluminum alloy material.

FIG. 73 shows an essential portion of a cooling curve for the aluminum alloy material in the course of production of the aluminum alloy casting $A_3$. The temperature at a start point $y_1$ in an eutectic reaction is 552° C.; the temperature at an end point $y_2$ is 535.8° C.; and an eutectic reaction time z between the start point $y_1$ and the end point $y_2$ is 0.2 seconds. Therefore, the reaction rate during the eutectic reaction is 81° C./sec.

Figure 74:
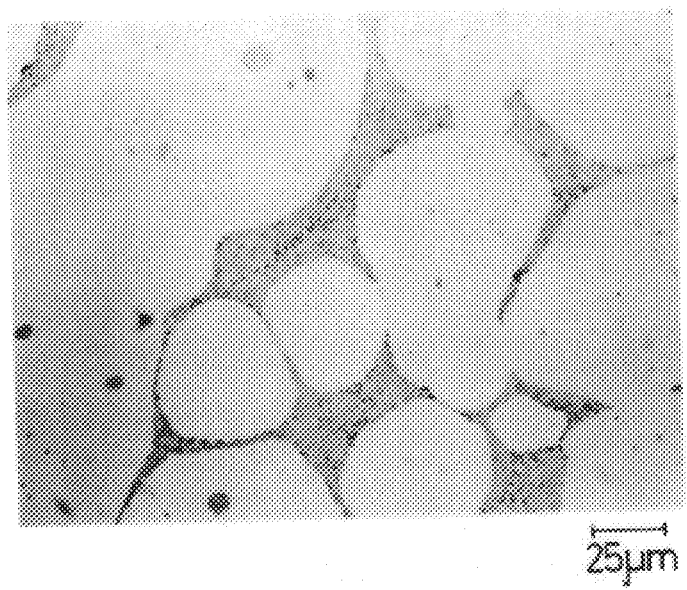
FIG. 74 is a photomicrograph showing the metallographic structure of an aluminum alloy casting $A_1$.

FIG. 74 is a photomicrograph showing the metallographic structure of the aluminum alloy casting $A_1$. It can be seen from FIG. 74 that the metallographic structure of the aluminum alloy casting $A_1$ is formed of light-color primary crystals α-Al, and dark color eutectic-structure portions filled between the primary crystals α-Al, and includes no primary crystal Si (an alloy element) precipitated therein.

Figure 75:
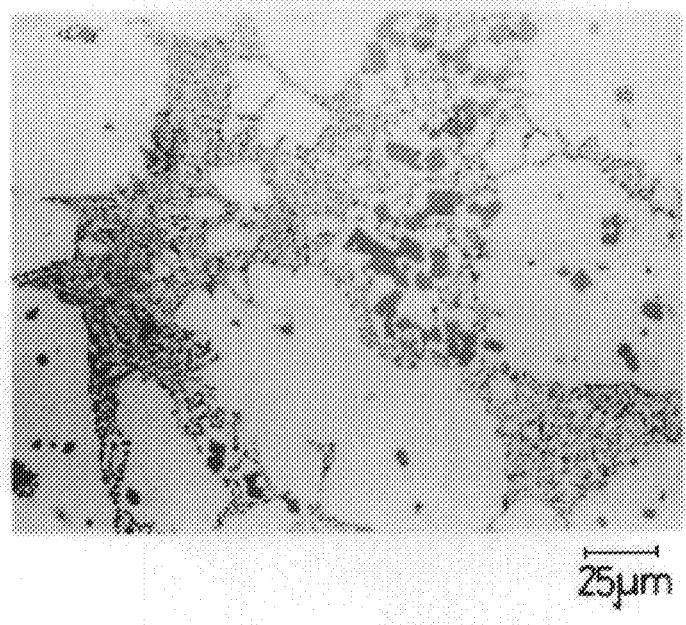
FIG. 75 is a photomicrograph showing the metallographic structure of an aluminum alloy casting $A_5$.

FIG. 75 is a photomicrograph showing the metallographic structure of the aluminum alloy casting $A_5$. It can be seen from FIG. 75 that a large number of black and angular primary crystals Si were precipitated in the eutectic structure and the primary crystal α-Al.

Figure 76:
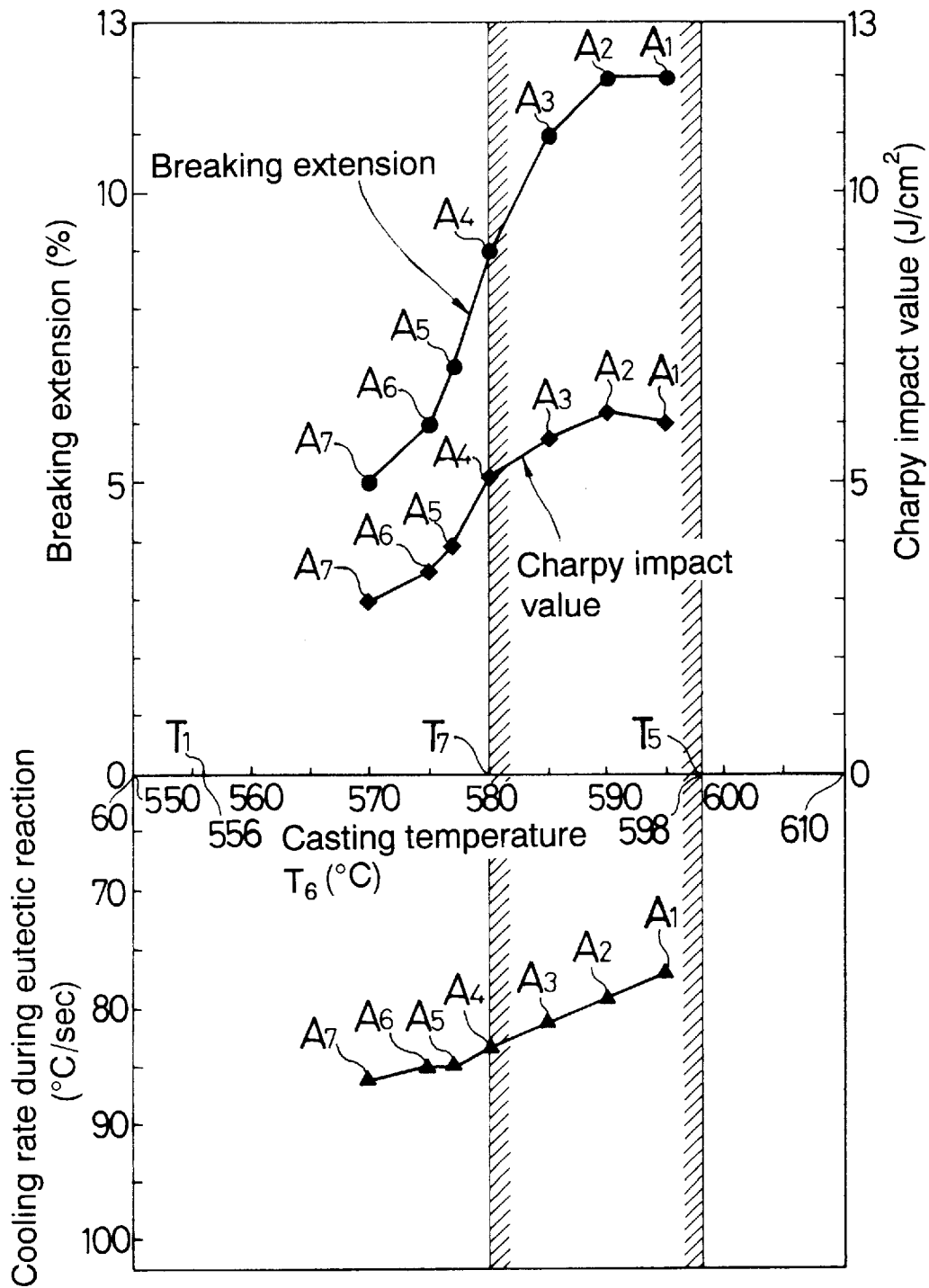
FIG. 76 is a graph illustrating the relationship between the casting temperature $T_6$, the cooling rate during an eutectic reaction, the breaking extension and the Charpy impact value.

FIG. 76 is a graph illustrating the relationship between the casting temperature $T_6$, the cooling rate during the eutectic reaction, the breaking extension, and the Charpy impact value as taken from Table 21. In FIG. 76, points $A_1$ to $A_7$ correspond to the aluminum alloy castings $A_1$ to $A_7$, respectively.

For the aluminum alloy castings $A_1$ to $A_7$ shown in FIG. 76, if the casting temperature $T_6$ for the aluminum alloy material is set in a range of $T_7$ (580° C.)$\leq T_6 \leq T_5$ (598° C.), the aluminum alloy material is brought into a semi-molten state and moreover, the solid phase proportion in the semi-molten aluminum alloy material is relatively lowered, i.e., the amount of the liquid phase is increased.

As a result, in the eutectic reaction of the semi-molten aluminum alloy material, the relatively large amount of liquid phase has a relatively large latent heat and hence, the cooling rate for the liquid phase is reduced. Thus, it is possible to avoid the precipitation of the primary crystal Si.

Consequently, each of the aluminum alloy castings $A_1$ to $A_4$ has a high ductility and a high toughness, as compared to the aluminum alloy castings $A_5$ to $A_7$ and thus with those produced with the casting temperature $T_6$ set at a level lower than $T_7$ and having a primary crystal Si precipitated therein.

The alloy material in each of the embodiments is not limited to the aluminum alloy material.

What is claimed is:

1. A thixocasting process comprising the steps of:
   heating an aluminum alloy material which includes a eutectic segment and a non-eutectic segment having a melting point higher than the eutectic temperature for said alloy material to a casting temperature $T_6$ to prepare a semi-molten alloy material having solid and liquid phases coexisting therein;
   subjecting said semi-molten alloy material to a pressure molding to thereby fill in the cavity of a casting mold with said semi-molten alloy material; and
   solidifying said semi-molten alloy material under said pressure; and wherein
   said alloy material has a characteristic that in a differential thermal analysis thermograph, a peak value $E_1$ of a first angled endothermic section generated by eutectic melting of said eutectic segment is larger than a peak value $E_2$ of a second angled endothermic section generated by melting of said non-eutectic segment; and
   said casting temperature $T_6$ of said alloy material is set in a range of $T_7 \leq T_6 \leq T_5$, wherein $T_7$ represents a temperature at a dropping endpoint in said first angled endothermic section, and $T_5$ represents a temperature at said peak value $E_2$ of said second angled endothermic section.

2. A thixocasting process according to claim 1, wherein in said differential thermal analysis thermograph, a dropping line segment of said first angled endothermic section and a rising line segment of said second angled endothermic section are connected to each other in an area of endotherm higher than a basic line which interconnects a rising start point of said first angled endothermic section and a dropping end point of said second angled endothermic section.

3. A thixocasting process according to claim 2, wherein in said differential thermal analysis thermograph, the gradient of said rising line segment of said second angled endothermic section is more moderate than the gradient of said dropping line segment of said first angled endothermic section.

4. A thixocasting process comprising the steps of:
   heating an aluminum alloy material which includes a eutectic segment and a non-eutectic segment having a melting point higher than the eutectic temperature for said alloy material to a casting temperature $T_6$ to prepare a semi-molten alloy material having solid and liquid phases coexisting therein;
   subjecting said semi-molten alloy material to a pressure molding to thereby fill in the cavity of a casting mold with said semi-molten alloy material; and
   solidifying said semi-molten alloy material under said pressure; and wherein
   said alloy material has a characteristic that in a differential thermal analysis thermograph, a ratio $E_1/E_2$ of a peak value $E_1$ of a first angled endothermic section generated by eutectic melting of said eutectic segment to a peak value $E_2$ of a second angled endothermic section generated by melting of said non-eutectic segment is in a range of $1<E_1/E_2<2.5$;

a difference $T_2-T_1$ between a temperature $T_1$ at a rising start point in said first angled endothermic section, and a temperature $T_2$ at a dropping end point in said second angled endothermic section, is in a range of $10°\ C.<T_2-T_1<120°\ C.$; and said casting temperature $T_6$ of said alloy material is set in a range of $T_7 \leq T_6 \leq T_5$, wherein $T_7$ represents a temperature at a dropping endpoint in said first angled endothermic section, and $T_5$ represents a temperature at said peak value $E_2$ of said second angled endothermic section.

5. A thixocasting process comprising the steps of:

heating an aluminum alloy material which includes a eutectic segment and a non-eutectic segment having a melting point higher than the eutectic temperature for said alloy material to a casting temperature $T_6$ to prepare a semi-molten alloy material having solid and liquid phases coexisting therein;

subjecting said semi-molten alloy material to a pressure molding to thereby fill in the cavity of a casting mold with said semi-molten alloy material; and solidifying said semi-molten alloy material under said pressure; and wherein said alloy material has a characteristic that in a differential thermal analysis thermograph, a relationship of $E_1>E_2$ is established between a peak value $E_1$ of a first angled endothermic section generated by eutectic melting of said eutectic segment and a peak value $E_2$ of a second angled endothermic section generated by melting of said non-eutectic segment;

said casting temperature $T_6$ of said alloy material is set in a range of $T_7 \leq T_6 \leq T_5$, wherein $T_7$ represents a temperature at a dropping endpoint in said first angled endothermic section, and $T_5$ represents a temperature at said peak value $E_2$ of said second angled endothermic section; and when a temperature straight line interconnecting said peak value $E_1$ of said first angled endothermic section and a temperature graduation corresponding to said peak value $E_1$ on an axis of heating temperature intersects, at a first intersection, a basic line which interconnects a rising start point in said first angled endothermic section and a dropping end point in said second angled endothermic section, and when a dividing line bisecting the segment of said temperature straight line lying between said peak value $E_1$ of said first angled endothermic section and said first intersection intersects, at a second intersection, a rising line segment of said first angled endothermic section lying between said rising start point and said peak value $E_1$, a relationship of $\Delta Tb/\Delta Ta \leq 0.68$ is established between $\Delta Ta$ $(=T_4-T_1)$ and $\Delta Tb$ $(=T_3-T_1)$, wherein $T_1$ represents a temperature at said rising start point, $T_3$ represents a temperature at said second intersection, and $T_4$ represents a temperature at said peak value $E_1$ of said first angled endothermic section.

6. A thixocasting process according to claim 5, wherein a relationship of $Sm/St \leq 0.365$ is established between (1) an area St of a region surrounded by said basic line, a first temperature straight line corresponding to said temperature straight line, and said rising line segment, and (2) an area Sm of a region surrounded by said basic line, a second temperature straight line which interconnects said second intersection and a temperature graduation corresponding to said second intersection on said axis of heating temperature, and the portion of said rising line segment lying between said rising start point and said second intersection.

7. A thixocasting process comprising the steps of:

heating an aluminum alloy material which includes a eutectic segment and a non-eutectic segment having a melting point higher than the eutectic segment to a casting temperature $T_6$ to prepare a semi-molten alloy material having solid and liquid phases coexisting therein;

subjecting said semi-molten alloy material to a pressure molding to thereby fill in the cavity of a casting mold with said semi-molten alloy material; and solidifying said semi-molten alloy material under said pressure; and wherein said alloy material has a characteristic that in a differential thermal analysis thermograph, a relationship of $E_1>E_2$ is established between a peak value $E_1$ of a first angled endothermic section generated by eutectic melting of said eutectic segment and a peak value $E_2$ of a second angled endothermic section generated by melting of said non-eutectic segment;

a relationship of $Sm/St \leq 0.365$ is established between (1) an area St of a region surrounded by (i) a basic line which interconnects a rising start point of said first angled endothermic section and a dropping end point of said second angled endothermic section, (ii) a first temperature straight line which interconnects said peak value $E_1$ of said first angled endothermic section and a temperature graduation corresponding to said peak value $E_1$ on an axis of heating temperature, and (iii) a rising line segment of said first angled endothermic section lying between said rising start point and said peak value $E_1$, and (2) an area Sm of a region surrounded by (i) a second temperature straight line that interconnects (a) a second intersection of said rising line segment with a dividing line which bisects a segment of said first temperature straight line lying between a first intersection of said first temperature straight line with said basic line and said peak value $E_1$ of said first angled endothermic section and (b) a temperature graduation corresponding to said second intersection on said axis of heating temperature, (ii) a portion of said rising line segment lying between said rising start point of said first angled endothermic section and said second intersection, and (iii) said basic line; and said casting temperature $T_6$ of said alloy material is set in a range of $T_7 \leq T_6 \leq T_5$, wherein $T_7$ represents a temperature at a dropping endpoint in said first angled endothermic section, and $T_5$ represents a temperature at said peak value $E_2$ of said second angled endothermic section.

8. A thixocasting process comprising the steps of:

heating an aluminum alloy material which includes a eutectic segment and a non-eutectic segment having a melting point higher than the eutectic temperature for said alloy material to a casting temperature $T_6$ to prepare a semi-molten alloy material having solid and liquid phases coexisting therein;

subjecting said semi-molten alloy material to a pressure molding to thereby fill in the cavity of a casting mold with said semi-molten alloy material; and solidifying said semi-molten alloy material under said pressure; and wherein said alloy material has a characteristic that in a differential thermal analysis thermograph, there exist a first angled endothermic section generated by a eutectic melting of said eutectic segment and a second angled endothermic section generated by melting of said non-eutectic segment;

a difference $T_5-T_4$ is in a range of $20°\,C.\leq T_5-T_4\leq 80°\,C.$, wherein $T_4$ represents a temperature at the peak of said first angled endothermic section and $T_5$ represents a temperature at the peak of said second angled endothermic section; and said casting temperature $T_6$ of said alloy material is set in a range of $T_7\leq T_6\leq T_5$, wherein $T_7$ represents a temperature at a dropping endpoint in said first angled endothermic section.

9. A thixocasting process comprising the steps of:

heating an aluminum alloy material which includes a eutectic segment and a non-eutectic segment having a melting point higher than the eutectic temperature of said alloy material to a casting temperature $T_6$ to prepare a semi-molten alloy material having solid and liquid phases coexisting therein;

subjecting said semi-molten alloy material to a pressure molding to thereby fill in the cavity of a casting mold with said semi-molten alloy material; and solidifying said semi-molten alloy material under said pressure; and wherein said alloy material has a characteristic that in a differential thermal analysis thermograph, there exist a first angled endothermic section generated by eutectic melting of said eutectic segment and a second angled endothermic section generated by melting of said non-eutectic segment, said second angled endothermic section having a sloping portion between a peak of said second angled endothermic section and a dropping end point in said second angled endothermic section, said sloping portion extending along a straight line interconnecting a rising start point in said first angled endothermic section and said dropping end point in said second angled endothermic section;

a proportion Rt (Td/Tc×100) of a temperature range Td between the peaks of said first and second angled endothermic sections and a solid-liquid phase-coexisting temperature range Tc between said rising start point in said first angled endothermic section and said dropping end point in said second angled endothermic section is in a range of $Rt\geq 69\%$; and said casting temperature $T_6$ of said alloy material is set in a range of $T_7\leq T_6\leq T_5$, wherein $T_7$ represents a temperature at a dropping endpoint in said first angled endothermic section, and $T_5$ represents a temperature at said peak of said second angled endothermic section.

10. A thixocasting process comprising the steps of:

heating an aluminum alloy material including a eutectic segment and a non-eutectic segment having a melting point higher than the eutectic temperature for said alloy material to a casting temperature $T_6$ to prepare a semi-molten material having solid and liquid phases co-existing therein;

subjecting said semi-molten alloy material to a pressure molding to thereby fill in the cavity of a casting mold with said semi-molten alloy material; and solidifying said semi-molten alloy material under said pressure; and wherein said alloy material has a characteristic that in a differential thermal analysis thermograph, there exists a first angled endothermic section generated by melting of said eutectic segment and a second angled endothermic section generated by melting of said non-eutectic segment;

said casting temperature $T_6$ of said alloy material is set in a range of $T_7\leq T_6\leq T_5$, wherein $T_7$ represents a temperature at a dropping endpoint in said first angled endothermic section, and $T_5$ represents a temperature at a peak of said second angled endothermic section; and a ratio $\alpha/\beta$ between the following two average temperature rising rates $\alpha$ and $\beta$ is set in a range of $\alpha/\beta>1$, wherein $\alpha$ is the average temperature rising rate for the alloy material between a rising start point and said dropping end point in said first angled endothermic section, and $\beta$ is the average temperature rising rate for the alloy material between said dropping end point and said casting temperature $T_6$.

11. A thixocasting process comprising the steps of:

heating an aluminum alloy material which includes a eutectic segment and a non-eutectic segment having a melting point higher than the eutectic temperature of said alloy material to a casting temperature $T_6$ to prepare a semi-molten alloy material having solid and liquid phases coexisting therein;

subjecting said semi-molten alloy material to a pressure molding to thereby fill in the cavity of a casting mold with said semi-molten alloy material; and solidifying said semi-molten alloy material under said pressure; and wherein said alloy material has a characteristic that in a differential thermal analysis thermograph, a peak value $E_1$ of a first angled endothermic section generated by eutectic melting of said eutectic segment, and a peak value $E_2$ of a second angled endothermic section generated by melting of said non-eutectic segment, are in a relationship of $1<E_1/E_2<2.5$; and said casting temperature $T_6$ of said alloy material is set in a range of $T_7\leq T_6\leq T_5$, wherein $T_7$ represents a temperature at a dropping endpoint in said first angled endothermic section, and $T_5$ represents a temperature at said peak value $E_2$ of said second angled endothermic section.

12. A thixocasting process according to claim 11, wherein in said differential thermal analysis thermograph, a dropping line segment of said first angled endothermic section and a rising line segment of said second angled endothermic section are connected to each other in an area of endotherm higher than a basic line which interconnects a rising start point of said first angled endothermic section and a dropping end point of said second angled endothermic section.

13. A thixocasting process according to claim 12, wherein in said differential thermal analysis thermograph, the gradient of said rising line segment of said second angled endothermic section is more moderate than the gradient of said dropping line segment of said first angled endothermic section.

14. A thixocasting process according to claim 1 or 11, wherein in said differential thermal analysis thermography, the gradient of a rising line segment of said second angled endothermic section is more moderate than the gradient of a dropping line segment of said first angled endothermic section.

* * * * *

UNITED STATES PATENT AND TRADEMARK OFFICE
CERTIFICATE OF CORRECTION

PATENT NO. : 5,849,115  
DATED : December 15, 1998  
INVENTOR(S) : Shiina et al.

Page 1 of 1

It is certified that error appears in the above-identified patent and that said Letters Patent is hereby corrected as shown below:

<u>Column 42,</u>
Line 61, before "analysis" delete "thermography" and insert -- thermograph --

Signed and Sealed this

Seventh Day of May, 2002

Attest:

Attesting Officer

JAMES E. ROGAN
Director of the United States Patent and Trademark Office